United States Patent
Merla et al.

(10) Patent No.: US 7,608,619 B2
(45) Date of Patent: Oct. 27, 2009

(54) SUBSTITUTED OXAZOLE COMPOUNDS WITH ANALGESIC ACTIVITY

(75) Inventors: Beatrix Merla, Aachen (DE); Stefan Oberboersch, Aachen (DE); Bernd Sundermann, Aachen (DE); Werner Englberger, Stolberg (DE); Hagen-Heinrich Hennies, Simmerath (DE); Heinz Graubaum, Erkner (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/143,519

(22) Filed: Jun. 20, 2008

(65) Prior Publication Data
US 2009/0069330 A1   Mar. 12, 2009

Related U.S. Application Data

(63) Continuation of application No. PCT/EP2006/012222, filed on Dec. 19, 2006.

(30) Foreign Application Priority Data
Dec. 22, 2005   (DE) .................. 10 2005 061 429

(51) Int. Cl.
| | |
|---|---|
| A61K 31/5377 | (2006.01) |
| A61K 31/421 | (2006.01) |
| A61K 31/454 | (2006.01) |
| C07D 413/02 | (2006.01) |
| C07D 413/14 | (2006.01) |
| C07D 263/48 | (2006.01) |

(52) U.S. Cl. ................ 514/236.8; 514/326; 514/377; 544/137; 546/209; 548/233
(58) Field of Classification Search ................ None
See application file for complete search history.

(56) References Cited

FOREIGN PATENT DOCUMENTS

| WO | WO 99/09829 A1 | 3/1999 |
|---|---|---|
| WO | WO 99/09979 A1 | 3/1999 |

OTHER PUBLICATIONS

International Search Report dated May 8, 2007 (two (2) pages).

*Primary Examiner*—Kamal A Saeed
(74) *Attorney, Agent, or Firm*—Crowell & Moring LLP

(57) ABSTRACT

Substituted oxazole derivatives corresponding to formula I:

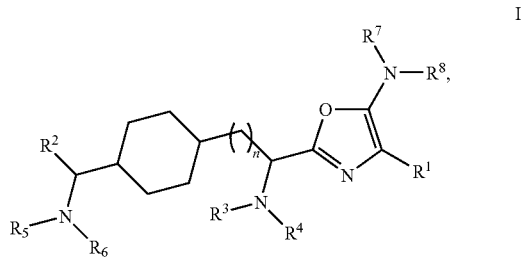

a method for producing such compounds, pharmaceutical compositions containing such compounds, and the use of such compounds to treat pain, depression, urinary incontinence, diarrhoea, pruritus, alcohol and drug misuse, drug dependency, lethargy and/or anxiety.

20 Claims, No Drawings

US 7,608,619 B2

SUBSTITUTED OXAZOLE COMPOUNDS WITH ANALGESIC ACTIVITY

CROSS REFERENCE TO RELATED APPLICATIONS

This application is a continuation of international patent application no. PCT/EP2006/012222, filed Dec. 19, 2006, designating the United States of America, and published in German on Jul. 19, 2007 as WO 2007/079928, the entire disclosure of which is incorporated herein by reference. Priority is claimed based on Federal Republic of Germany patent application no. DE 10 2005 061.429.9, filed Dec. 22, 2005.

BACKGROUND OF THE INVENTION

The present invention relates to substituted oxazole derivatives, processes for their preparation, medicaments containing these compounds, and the use of substituted oxazole derivatives for the preparation of medicaments.

The treatment of chronic and non-chronic pain states is extremely important in medicine. There is therefore a widespread need for highly effective pain treatments. The urgent need for a patient-friendly and targeted treatment of chronic and non-chronic pain states, which from the patient's point of view is hereinafter understood to mean the successful and satisfactory handling and treatment of pain, is well documented in the large number of scientific papers and articles that have appeared in recent years in the field of applied analgesics and in basic research on nociception.

Conventional opioids such as morphine are highly effective in the treatment of severe to extremely severe pain. Their use is however limited by their known side effects, for example respiratory depression, nausea, vomiting, sedation, constipation and development of tolerance. Also, they are less effective in neuropathic or incidental pain, including in particular tumour patients.

In Org. Lett 2001, 3, 877-880 oxazole derivatives are disclosed, which are likewise substituted in the 5-position with a secondary amine. These oxazole derivatives are however not substituted in the 2-position by a substituted alkyl chain with an aminomethyl-substituted cyclohexyl radical.

SUMMARY OF THE INVENTION

A basic object of the invention was to provide new analgesically effective substances that are suitable for treating pain, in particular also chronic and neuropathic pain.

The invention accordingly provides substituted oxazole derivatives of the general Formula I,

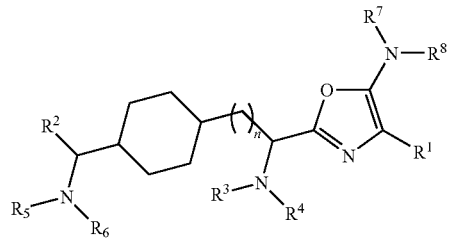

wherein
n is 0, 1 or 2;
R$^1$ denotes an aryl or heteroaryl radical bonded via a C$_{1-3}$-alkylene chain, in each case unsubstituted or monosubstituted or polysubstituted;
R$^2$ denotes aryl or heteroaryl, in each case unsubstituted or monosubstituted or polysubstituted; an aryl radical bonded via a C$_{1-3}$-alkylene chain, in each case unsubstituted or monosubstituted or polysubstituted;
R$^3$ and R$^4$ independently of one another denote C$_{1-6}$-alkyl, saturated or unsaturated, branched or unbranched, unsubstituted or monosubstituted or polysubstituted; aryl, unsubstituted or monosubstituted or polysubstituted; an aryl radical bonded via a C$_{1-3}$-alkylene chain, in each case unsubstituted or monosubstituted or polysubstituted; or
R$^3$ and R$^4$ together form a 5-, 6- or 7-membered ring, which can be saturated or unsaturated but not aromatic, which optionally contains a further heteroatom from the group S, O or N and in each case is unsubstituted or monosubstituted or polysubstituted, wherein the ring is optionally condensed to an aromatic ring;
R$^5$ and R$^6$ independently of one another denote H; C$_{1-6}$-alkyl, in each case saturated or unsaturated, branched or unbranched, wherein R$^5$ and R$^6$ do not simultaneously denote H; or
R$^5$ and R$^6$ together denote CH$_2$CH$_2$OCH$_2$CH$_2$, or (CH$_2$)$_{3-6}$,
R$^7$ and R$^8$ independently of one another denote C$_{1-6}$-alkyl, saturated or unsaturated, branched or unbranched, unsubstituted or monosubstituted or polysubstituted; an aryl or heteroaryl radical bonded via a C$_{1-3}$-alkylene chain, in each case unsubstituted or monosubstituted or polysubstituted; or
R$^7$ and R$^8$ together form a 5-, 6- or 7-membered ring, which can be saturated or unsaturated, but not aromatic, which optionally contains a further heteroatom from the group S, O or N and is in each case unsubstituted or monosubstituted or polysubstituted, wherein the ring is optionally condensed to an aromatic ring, in the form of the racemate; in the form of the enantiomers, diastereomers, mixtures of the enantiomers or diastereomers, or of an individual enantiomer or diastereomer; in the form of the bases and/or salts of physiologically compatible acids. The compounds have an affinity for the μ-opioid receptor.

The expressions "C$_{1-3}$-alkyl", "C$_{1-4}$-alkyl" and "C$_{1-6}$-alkyl" include in the context of the present invention acyclic saturated or unsaturated hydrocarbon radicals, which can be branched or straight-chain, as well as unsubstituted or monosubstituted or polysubstituted, with 1 to 3 C atoms or 1 to 4 C atoms or 1 to 6 C atoms, i.e. C$_{1-3}$-alkanyls, C$_{2-3}$-alkenyls and C$_{2-3}$-alkinyls, or C$_{1-4}$-alkanyls, C$_{2-4}$-alkenyls and C$_{2-4}$-alkinyls, or C$_{1-6}$-alkanyls, C$_{2-6}$-alkenyls and C$_{2-6}$-alkinyls. In this connection alkenyls have at least one C—C double bond and alkinyls have at least one C—C triple bond. Advantageously alkyl is selected from the group comprising methyl, ethyl, n-propyl, 2-propyl, n-butyl, iso-butyl, sec.-butyl, tert.-butyl, n-pentyl, iso-pentyl, neo-pentyl, n-hexyl, 2-hexyl, ethylenyl (vinyl), ethinyl, propenyl (—CH$_2$CH=CH$_2$, —CH=CH—CH$_3$, —C(=CH$_2$)—CH$_3$), propinyl (—CH—C≡CH, —C≡C—CH$_3$), butenyl, butinyl, pentenyl, pentinyl, hexenyl and hexinyl. Particularly preferred are methyl, ethyl, n-propyl, n-butyl, sec-butyl, iso-butyl.

If two substituents of a N atom "together form a 5-, 6- or 7-membered ring, which can be saturated or unsaturated but not aromatic, which optionally contains a further heteroatom from the group S, O or N", this means in the context of the present invention that the two substituents form a ring that includes the N atom. Rings from the following group are advantageous: pyrrolidine, piperidine, azepan, piperazine, diazepan, imidazolidine, morpholine, thiomorpholine, oxazepan, thiazepan, oxazolidine or thiazolidine. Piperidine, piperazine, morpholine and thiomorpholine are particularly preferred.

The expression "aryl" denotes within the meaning of the present invention aromatic hydrocarbons, inter alia phenyls and naphthyls. The aryl radicals can also be condensed with further saturated, (partially) unsaturated or aromatic ring systems. Each aryl radical can be unsubstituted or monosubstituted or polysubstituted, wherein the aryl substituents can be identical or different and can be in any arbitrary and possible position of the aryl radical. Advantageously aryl is selected from the group containing phenyl, 1-naphthyl, 2-naphthyl, which can in each case be unsubstituted or monosubstituted or polysubstituted. The phenyl radical is particularly advantageous.

The expression "heteroaryl" denotes a 5-, 6- or 7-membered cyclic aromatic radical that contains at least 1, possibly also 2, 3, 4 or 5 heteroatoms, in which the heteroatoms are identical or different and the heterocycle can be unsubstituted or monosubstituted or polysubstituted; in the case of the substitution on the heterocycle, the substituents can be identical or different and can be in any arbitrary and possible position of the heteroaryl. The heterocycle can also be part of a bicyclic or polycyclic system. Preferred heteroatoms are nitrogen, oxygen and sulfur. It is preferred that the heteroaryl radical is selected from the group containing pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazoyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bonding to the compounds of the general structure I can take place via any arbitrary and possible ring member of the heteroaryl radical. Pyridyl, furyl, thienyl and indolyl are particularly preferred.

The expression "aryl or heteroaryl bonded via $C_{1-3}$-alkylene" means, for the purposes of the present invention, that $C_{1-3}$-alkyl and aryl or heteroaryl have the meanings defined above and that the aryl or heteroaryl radical is bonded via a $C_{1-3}$-alkylene group to the compound of the general structure 1. Within the context of the present invention benzyl is particularly advantageous.

In connection with "alkyl" or a "5-, 6- or 7-membered ring, which can be saturated or unsaturated but not aromatic", the term "substituted" is understood within the context of the present invention to denote the substitution of a hydrogen atom by F, Cl, Br, I, —CN, $NH_2$, NH—$C_{1-6}$-alkyl, NH—$C_{1-6}$-alkyl-OH, $C_{1-6}$-alkyl, $N(C_{1-6}$-alkyl$)_2$, $N(C_{1-6}$-alkyl-OH$)_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, wherein polysubstituted radicals are understood to be those radicals that are polysubstituted, for example disubstituted or trisubstituted, either on different atoms or on the same atoms, for example trisubstituted on the same C atom as in the case of $CF_3$ or —$CH_2CF_3$, or at different sites as in the case of —CH(OH)—CH=CH—$CHCl_2$. The polysubstitution can take place with the same or with different substituents. For the purposes of the present invention "monosubstituted or polysubstituted" in connection with alkyl or a saturated or unsaturated ring, which cannot be aromatic, particularly preferably denotes benzyl or methyl.

With regard to "aryl" and "heteroaryl", within the context of the present invention "monosubstituted or polysubstituted" denotes monosubstitution or polysubstitution, for example disubstitution, trisubstitution or tetrasubstitution, of one or more hydrogen atoms of the ring system by F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl, on one or possibly different atoms (in which connection a substituent can optionally for its part be substituted). The polysubstitution can in this connection be carried out with the same or with different substituents. For "aryl" and "heteroaryl" preferred substituents in this case are F, —Cl, —$CF_3$, —O—$CH_3$, methyl, ethyl, n-propyl, nitro, tert.-butyl and —CN. Particularly preferred are —F and —Cl.

The expression "salt formed with a physiologically compatible acid" is understood within the context of the present invention to mean salts of the respective active substance with inorganic or organic acids which are physiologically compatible, especially when used in humans and/or mammals. The hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro$1\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Hydrochloric acid is particularly preferred.

The groups $(CH_2)_{3-6}$ and $(CH_2)_{4-5}$ are understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, and —$CH_2$—$CH_2$—$CH_2$—$CH_2$— and —$CH_2$—$CH_2$—$CH_2$—$CH_2$—$CH_2$—$CH_2$.

Preferred within the meaning of the present invention are oxazole derivatives in which $R^1$ denotes an aryl or heteroaryl radical bonded via a $C_{1-3}$-alkylene chain, in each case unsubstituted or monosubstituted or polysubstituted with F, Cl, Br, I, CN, $NH_2$, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $C_{1-6}$-alkyl.

Preferably $R^1$ denotes a phenyl radical bonded via a $C_{1-3}$-alkylene chain, unsubstituted or monosubstituted or polysubstituted with F, Cl, CN, $NO_2$, SH, S—$C_{1-6}$-alkyl, OH, O—$C_{1-6}$ -alkyl, $CO_2H$, $CO_2$—$C_{1-6}$-alkyl, $CF_3$, $C_{1-6}$-alkyl. Particularly preferred are oxazole derivatives in which $R^1$ denotes benzyl.

Preferred in the context of the present invention are also substituted oxazole derivatives, in which $R^2$ denotes phenyl, thienyl or pyridyl, in each case unsubstituted or monosubstituted or polysubstituted with F, Cl, CN, NH—$C_{1-6}$-alkyl, NH—$C_{1-6}$-alkyl-OH, $N(C_{1-6}$-alkyl$)_2$, $N(C_{1-6}$-alkyl-OH$)_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl; an aryl radical bonded via a $C_{1-3}$-alkylene chain, in each case unsubstituted or monosubstituted or polysubstituted with F, Cl, CN, NH—$C_{1-6}$-alkyl, NH—$C_{1-6}$-alkyl —OH, $N(C_{1-6}$-alkyl$)_2$, $N(C_{1-6}$-alkyl-OH$)_2$, $NO_2$, SH, S—$C_{1-6}$ -alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl.

Preferably $R^2$ denotes phenyl or thienyl, in each case unsubstituted or monosubstituted or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl; a phenyl radical bonded via a $C_{1-3}$-alkylene chain, in each case unsubstituted or monosubstituted or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, $C_{1-6}$-alkyl.

In particular, $R^2$ denotes phenyl, unsubstituted or monosubstituted or polysubstituted with F, Cl, OH, $OCH_3$, $CF_3$ or $CH_3$; thienyl; or a phenyl radical bonded via a $C_{1-3}$-alkylene chain, unsubstituted or monosubstituted or polysubstituted with F, Cl, CN, OH, $OCH_3$, $CF_3$ or $CH_3$.

Most particularly preferred are oxazole derivatives in which $R^2$ denotes phenyl, unsubstituted or monosubstituted with Cl or F, or thienyl.

Also preferred in the context of the present invention are substituted oxazole derivatives, in which $R^3$ and $R^4$ independently of one another denote $C_{1-6}$-alkyl, saturated or unsaturated, branched or unbranched, unsubstituted or monosubstituted or polysubstituted with F, Cl, Br, I, —CN, $NH_2$, NH—$C_{1-6}$-alkyl, NH—$C_{1-6}$-alkyl-OH, $C_{1-6}$-alkyl, $N(C_{1-6}\text{-alkyl})_2$, $N(C_{1-6}\text{-alkyl-OH})_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl; aryl, unsubstituted or monosubstituted or polysubstituted with F, Cl, Br, I, CN, $NH_2$, NH—$C_{1-6}$-alkyl, NH—$C_{1-6}$-alkyl-OH, $N(C_{1-6}\text{-alkyl})_2$, $N(C_{1-6}\text{-alkyl-OH})_2$, $NO_2$, SH, S—$C_{1-6}$-alkyl, OH, O—$C_{1-6}$-alkyl, O—$C_{1-6}$-alkyl-OH, C(=O)$C_{1-16}$-alkyl, $CO_2H$, $CO_2$—$C_{1-6}$-alkyl, $CF_3$, $C_{1-6}$-alkyl; an aryl radical bonded via a $C_{1-3}$-alkylene chain, in each case unsubstituted or monosubstituted or polysubstituted with F, Cl, Br, I, CN, $NH_2$, NH—$C_{1-6}$-alkyl, NH—$C_{1-6}$-alkyl-OH, $N(C_{1-6}\text{alkyl})_2$, $N(C_{1-6}\text{-alkyl-OH})_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl.

Other preferred compounds are those in which $R^3$ and $R^4$ together form a 5-, 6- or 7-membered ring, which can be saturated or unsaturated, but not aromatic, which optionally contains a further heteroatom from the group S, O or N and is in each case unsubstituted or can be monosubstituted or polysubstituted with F, Cl, Br, I, —CN, $NH_2$, NH—$C_{1-6}$-alkyl, NH—$C_{1-6}$-alkyl-OH, $C_{1-6}$-alkyl, $N(C_{1-6}\text{-alkyl})_2$, $N(C_{1-6}\text{-alkyl-OH})_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, wherein the ring is optionally condensed with an aromatic ring.

Preferably $R^3$ and $R^4$ independently of one another denote $C_{1-6}$-alkyl, unsubstituted or monosubstituted or polysubstituted with F, Cl, —CN, SH, S—$C_{1-6}$-alkyl, benzyl, OH, O-benzyl, O—$C_{1-6}$-alkyl, $CO_2H$, $CO_2$—$C_{1-6}$-alkyl; or phenyl, unsubstituted or monosubstituted or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$ or $C_{1-6}$-alkyl; or $R^3$ and $R^4$ together denote —$CH_2CH_2OCH_2CH_2$—, —$CH_2CH_2NR^9CH_2CH_2$—, —$(CH_2)_{4-5}$— or

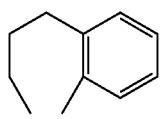

wherein $R^9$ denotes a phenyl group bonded via a $C_{1-3}$-alkylene chain, in each case unsubstituted or monosubstituted or polysubstituted with F, Cl, Br, I, CN, $NH_2$, NH—$C_{1-6}$-alkyl, NH—$C_{1-6}$-alkyl-OH, $N(C_{1-6}\text{-alkyl})_2$, $N(C_{1-6}\text{-alkyl-OH})_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, $C_{1-6}$-alkyl; or denotes $C_{1-6}$-alkyl.

Most particularly preferred are oxazole derivatives in which $R^3$ and $R^4$ independently of one another denote phenyl, ethyl or methyl, or the radicals $R^3$ and $R^4$ together denote $CH_2CH_2OCH_2CH_2$, $CH_2CH_2NR^9CH_2CH_2$, $(CH_2)_{4-5}$ or

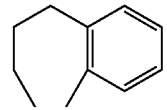

wherein $R^9$ denotes benzyl, 4-F-phenyl or 4-methoxyphenyl.

Also preferred in the context of the present invention are oxazole derivatives in which $R^5$ and $R^6$ independently of one another denote H or $C_{1-6}$-alkyl, wherein $R^5$ and $R^6$ do not simultaneously denote H, or $R^5$ and $R^6$ together denote —$CH_2CH_2OCH_2CH_2$— or —$(CH_2)_{4-5}$—.

Particularly preferred are oxazole derivatives in which $R^5$ and $R^6$ denote $CH_3$.

Also preferred are oxazole derivatives in which $R^7$ and $R^8$ independently of one another denote $C_{1-6}$-alkyl, saturated or unsaturated, branched or unbranched, unsubstituted or monosubstituted or polysubstituted with F, Cl, Br, I, —CN, $NH_2$, NH—$C_{1-6}$-alkyl, NH—$C_{1-6}$-alkyl-OH, $C_{1-6}$-alkyl, $N(C_{1-6}\text{-alkyl})_2$, $N(C_{1-6}\text{-alkyl-OH})_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl; an aryl radical bonded via a $C_{1-3}$-alkylene chain, in each case unsubstituted or monosubstituted or polysubstituted with F, Cl, Br, I, CN, $NH_2$, NH—$C_{1-6}$-alkyl, NH—$C_{1-6}$-alkyl-OH, $N(C_{1-6}\text{-alkyl})_2$, $N(C_{1-6}\text{-alkyl-OH})_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CO_2$—$C_{1-6}$-alkyl, $CF_3$, $C_{1-6}$-alkyl.

Alternative preferred compounds are those in which $R^7$ and $R^8$ together form a 5-, 6- or 7-membered ring, which can be saturated or unsaturated but not aromatic, which optionally contains a further heteroatom from the group S, O or N and in each case can be unsubstituted or monosubstituted or polysubstituted with F, Cl, Br, I, —CN, $NH_2$, NH—$C_{1-6}$-alkyl, NH—$C_{1-6}$-alkyl-OH, $C_{1-6}$-alkyl, $N(C_{1-6}\text{-alkyl})_2$, $N(C_{1-6}\text{-alkyl-OH})_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, wherein the ring is optionally condensed with an aromatic ring.

In particular, $R^7$ and $R^8$ independently of one another preferably denote benzyl or phenethyl, in each case unsubstituted or monosubstituted or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$ or $C_{1-6}$-alkyl; or $R^7$ and $R^8$ together denote —$CH_2CH_2SCH_2CH_2$—, —$CH_2CH_2OCH_2CH_2$—, —$(CH_2)_4$—, —$(CH_2)_5$—, —$CH_2CH_2NR^{10}CH_2CH_2$—, wherein individual H atoms can be replaced by $C_{1-4}$-alkyl, branched or unbranched, unsubstituted or monosubstituted or polysubstituted with OH, $OCH_3$, CN, F, Cl, SH, $SCH_3$, $CF_3$ or benzyl; wherein $R^{10}$ denotes phenyl, benzyl or phenethyl, unsubstituted or monosubstituted or polysubstituted with $CH_3$, $OCH_3$, OH, F, Cl, CN, SH, $SCH_3$ or $CF_3$.

Most particularly preferred are oxazole derivatives in which $R^7$ and $R^8$ independently of one another denote methyl, ethyl, benzyl or phenethyl; or $R^7$ and $R^8$ denote —$CH_2CH_2SCH_2CH_2$—, —$CH_2CH_2OCH_2CH_2$—, —$(CH_2)_4$— or —$(CH_2)_5$—, —$CH_2CH_2NR^{10}CH_2CH_2$—, wherein individual H atoms can be replaced by methyl or benzyl, and R$^{10}$ denotes phenyl, 4-methoxyphenyl or benzyl;

It is also preferred that n is 0 or 1.

Most particularly preferred are substituted oxazole derivatives selected from the group consisting of:

17. [{4-[(4-benzyl-5-pyrrolidin-1-yl-oxazol-2-yl)-piperidin-1-yl-methyl]-cyclohexyl}-(4-fluorophenyl)-methyl]-dimethylamine
18. ((4-benzyl-5-morpholin-4-yl-oxazol-2-yl)-{4-[dimethylamino-(4-fluorophenyl)-methyl]-cyclohexyl}-methyl)-methylphenylamine
19. ([4-benzyl-5-(4-methylpiperidin-1-yl)-oxazol-2-yl]-{4-[dimethylamino-(4-fluorophenyl)-methyl]-cyclohexyl}-methyl)-methylphenylamine
20. ([4-benzyl-5-(4-methylpiperidin-1-yl)-oxazol-2-yl]-{4-[(4-chlorophenyl)-dimethylaminomethyl]-cyclohexyl}-methyl)-diethylamine
21. benzyl-[4-benzyl-2-({[(4-chlorophenyl)-dimethylaminomethyl]-cyclohexyl}-diethylaminomethyl)-oxazol-5-yl]-methylamine
22. benzyl-{4-benzyl-2-[{4-[(4-chlorophenyl)-dimethylaminomethyl]-cyclohexyl}-(methylphenylamine)-methyl]-oxazol-5-yl}-methylamine
23. [(4-{[4-benzyl-5-(4-benzylpiperidin-1-yl)-oxazol-2-yl]-piperidin-1-yl-methyl}-cyclohexyl)-thiophen-2-yl-methyl]-dimethylamine
24. [(4-{[4-benzyl-5-(4-methylpiperidin-1-yl)-oxazol-2-yl]-piperidin-1-yl-methyl}-cyclohexyl)-thiophen-2-yl-methyl]-dimethylamine
25. benzyl-(4-benzyl-2-{[4-(dimethylaminothiophen-2-yl-methyl)-cyclohexyl]-piperidin-1-yl-methyl}-oxazol-5-yl)-methylamine
26. [(4-{[4-benzyl-5-(4-phenylpiperazin-1-yl)-oxazol-2-yl]-piperidin-1-yl-methyl}-cyclohexyl)-thiophen-2-yl-methyl]-dimethylamine
27. {[4-benzyl-5-(4-benzylpiperidin-1-yl)-oxazol-2-yl]-[4-(dimethylaminothiophen-2-yl-methyl)-cyclohexyl]-methyl}-diethylamine
28. {[4-benzyl-5-(4-benzylpiperazin-1-yl)-oxazol-2-yl]-[4-(dimethylaminothiophen-2-yl-methyl)-cyclohexyl]-methyl}-diethylamine
29. {[4-benzyl-5-(4-methylpiperidin-1-yl)-oxazol-2-yl]-[4-(dimethylaminothiophen-2-yl-methyl)-cyclohexyl]-methyl}-diethylamine
30. benzyl-(4-benzyl-2-{diethylamino-[4-(dimethylaminothiophen-2-yl-methyl)-cyclohexyl]-methyl}-oxazol-5-yl)-methylamine
31. {[4-benzyl-5-(4-phenylpiperazin-1-yl)-oxazol-2-yl]-[4-(dimethylaminothiophen-2-yl-methyl)-cyclohexyl]-methyl}-diethylamine
32. ({4-[[4-benzyl-5-(4-benzylpiperidin-1-yl)-oxazol-2-yl]-(4-benzylpiperazin-1-yl)-methyl]-cyclohexyl}-thiophen-2-yl-methyl)-dimethylamine
33. [(4-{[4-benzyl-5-(3-methylpiperidin-1-yl)-oxazol-2-yl]-piperidin-1-yl-methyl}-cyclohexyl)-(4-fluorophenyl)-methyl]-dimethylamine
34. [4-benzyl-2-(diethylamino-{4-[dimethylamino-(4-fluorophenyl)-methyl]-cyclohexyl}-methyl)-oxazol-5-yl]-methylphenethylamine
35. [4-benzyl-2-(diethylamino-{4-[dimethylamino-(4-fluorophenyl)-methyl]-cyclohexyl}-methyl)-oxazol-5-yl]-diethylamine
36. ([4-benzyl-5-(3-methylpiperidin-1-yl)-oxazol-2-yl]-{4-[dimethylamino-(4-fluorophenyl)-methyl]-cyclohexyl}-methyl)-diethylamine
37. ([4-benzyl-5-(3,5-dimethylpiperidin-1-yl)-oxazol-2-yl]-{4-[dimethylamino-(4-fluorophenyl)-methyl]-cyclohexyl}-methyl)-methylphenylamine
38. {4-benzyl-2-[{4-[dimethylamino-(4-fluorophenyl)-methyl]-cyclohexyl}-(methylphenylamine)-methyl]-oxazol-5-yl}-methylphenethylamine
39. [4-benzyl-2-({4-[(4-chlorophenyl)-dimethylaminomethyl]-cyclohexyl}-piperidin-1-yl-methyl)-oxazol-5-yl]-diethylamine
40. [(4-{[4-benzyl-5-(3-methylpiperidin-1-yl)-oxazol-2-yl]-piperidin-1-yl-methyl}-cyclohexyl)-(4-chlorophenyl)-methyl]-dimethylamine
41. ([4-benzyl-5-(3,5-dimethylpiperidin-1-yl)-oxazol-2-yl]-{4-[(4-chlorophenyl)-dimethylaminomethyl]-cyclohexyl}-methyl)-diethylamine
42. ([4-benzyl-5-(3,5-dimethylpiperidin-1-yl)-oxazol-2-yl]-{4-[(4-chlorophenyl)-dimethylaminomethyl]-cyclohexyl}-methyl)-methylphenylamine
43. {4-benzyl-2-[{4-[(4-chlorophenyl)-dimethylaminomethyl]-cyclohexyl}-(methylphenylamine)-methyl]-oxazol-5-yl}-methylphenethylamine
44. [4-benzyl-2-((4-benzylpiperazin-1-yl)-{4-[(4-chlorophenyl)-dimethylaminomethyl]-cyclohexyl}-methyl)-oxazol-5-yl]-diethylamine
45. [(4-{[4-benzyl-5-(3,5-dimethylpiperidin-1-yl)-oxazol-2-yl]-piperidin-1-yl-methyl}-cyclohexyl)-thiophen-2-yl-methyl]-dimethylamine
46. (4-benzyl-2-{[4-(dimethylaminothiophen-2-yl-methyl)-cyclohexyl]-piperidin-1-yl-methyl}-oxazol-5-yl)-methylphenethylamine
47. (4-benzyl-2-{[4-(dimethylaminothiophen-2-yl-methyl)-cyclohexyl]-piperidin-1-yl-methyl}-oxazol-5-yl)-diethylamine
48. ({4-[(4-benzyl-5-thiomorpholin-4-yl-oxazol-2-yl)-piperidin-1-yl-methyl]-cyclohexyl}-thiophen-2-yl-methyl)-dimethylamine
49. (4-benzyl-2-{diethylamino-[4-(dimethylaminothiophen-2-yl-methyl)-cyclohexyl]-methyl}-oxazol-5-yl)-methylphenethylamine
50. (4-benzyl-2-{diethylamino-[4-(dimethylaminothiophen-2-yl-methyl)-cyclohexyl]-methyl}-oxazol-5-yl)-diethylamine
51. {[4-benzyl-5-(3-methylpiperidin-1-yl)-oxazol-2-yl]-[4-(dimethylaminothiophen-2-yl-methyl)-cyclohexyl]-methyl}-diethylamine
52. {(4-benzyl-5-thiomorpholin-4-yl-oxazol-2-yl)-[4-(dimethylaminothiophen-2-yl-methyl)-cyclohexyl]-methyl}-methylphenylamine
53. ({4-[[4-benzyl-5-(3,5-dimethylpiperidin-1-yl)-oxazol-2-yl]-(4-benzylpiperazin-1-yl)-methyl]-cyclohexyl}-thiophen-2-yl-methyl)-dimethylamine
54. (4-benzyl-2-{(4-benzylpiperazin-1-yl)-[4-(dimethylaminothiophen-2-yl-methyl)-cyclohexyl]-methyl}-oxazol-5-yl)-methylphenethylamine
55. ({4-[(4-benzylpiperazin-1-yl)-(4-benzyl-5-thiomorpholin-4-yl-oxazol-2-yl)-methyl]-cyclohexyl}-thiophen-2-yl-methyl)-dimethylamine
56. [(4-{2-[4-benzyl-5-(4-benzylpiperazin-1-yl)-oxazol-2-yl]-2-piperidin-1-yl-ethyl}-cyclohexyl)-(4-chlorophenyl)-methyl]-dimethylamine
57. [(4-{2-[4-benzyl-5-(4-methylpiperidin-1-yl)-oxazol-2-yl]-2-piperidin-1-yl-ethyl}-cyclohexyl)-(4-chlorophenyl)-methyl]-dimethylamine
58. benzyl-[4-benzyl-2-(2-{4-[(4-chlorophenyl)-dimethylaminomethyl]-cyclohexyl}-1-piperidin-1-yl-ethyl)-oxazol-5-yl]-methylamine 59. (1-[4-benzyl-5-(4-benzylpiperidin-1-yl)-oxazol-2-yl]-2-{4-[(4-chlorophenyl)-dimethylaminomethyl]-cyclohexyl}-ethyl)-diethylamine
60. (1-[4-benzyl-5-(4-methylpiperidin-1-yl)-oxazol-2-yl]-2-{4-[(4-chlorophenyl)-dimethylaminomethyl]-cyclohexyl}-ethyl)-diethylamine
61. benzyl-[4-benzyl-2-(2-{4-[(4-chlorophenyl)-dimethylaminomethyl]-cyclohexyl}-1-diethylaminoethyl)-oxazol-5-yl]-methylamine
62. [{4-[2-[4-benzyl-5-(4-benzylpiperidin-1-yl)-oxazol-2-yl]-2-(4-benzylpiperazin-1-yl)-ethyl]-cyclohexyl}-(4-chlorophenyl)-methyl]-dimethylamine
63. [{4-[2-[4-benzyl-5-(4-benzylpiperazin-1-yl)-oxazol-2-yl]-2-(4-benzylpiperazin-1-yl)-ethyl]-cyclohexyl}-(4-chlorophenyl)-methyl]-dimethylamine
64. [{4-[2-[4-benzyl-5-(4-methylpiperidin-1-yl)-oxazol-2-yl]-2-(4-benzyl-piperazin-1-yl)-ethyl]-cyclohexyl}-(4-chlorophenyl)-methyl]-dimethylamine
65. [(4-{2-[4-benzyl-5-(4-methylpiperidin-1-yl)-oxazol-2-yl]-2-piperidin-1-yl-ethyl}-cyclohexyl)-(4-fluorophenyl)-methyl]-dimethylamine
66. benzyl-[4-benzyl-2-(2-{4-[dimethylamino-(4-fluorophenyl)-methyl]-cyclohexyl}-1-piperidin-1-yl-ethyl)-oxazol-5-yl]-methylamine
67. (1-[4-benzyl-5-(4-benzylpiperidin-1-yl)-oxazol-2-yl]-2-{4-[dimethylamino-(4-fluorophenyl)-methyl]-cyclohexyl}-ethyl)-diethylamine
68. (1-[4-benzyl-5-(4-benzylpiperazin-1-yl)-oxazol-2-yl]-2-{4-[dimethylamino-(4-fluorophenyl)-methyl]-cyclohexyl}-ethyl)-diethylamine
69. (1-[4-benzyl-5-(4-methylpiperidin-1-yl)-oxazol-2-yl]-2-{4-[dimethylamino-(4-fluorophenyl)-methyl]-cyclohexyl}-ethyl)-diethylamine
70. benzyl-[4-benzyl-2-(1-diethylamino-2-{4-[dimethylamino-(4-fluorophenyl)-methyl]-cyclohexyl}-ethyl)-oxazol-5-yl]-methylamine
71. [{4-[2-[4-benzyl-5-(4-methylpiperidin-1-yl)-oxazol-2-yl]-2-(4-benzylpiperazin-1-yl)-ethyl]-cyclohexyl}-(4-fluorophenyl)-methyl]-dimethylamine
72. [(4-{2-[4-benzyl-5-(4-benzylpiperidin-1-yl)-oxazol-2-yl]-2-piperidin-1-yl-ethyl}-cyclohexyl)-thiophen-2-yl-methyl]-dimethylamine
73. [(4-{2-[4-benzyl-5-(4-benzylpiperazin-1-yl)-oxazol-2-yl]-2-piperidin-1-yl-ethyl}-cyclohexyl)-thiophen-2-yl-methyl]-dimethylamine
74. [(4-{2-[4-benzyl-5-(4-methylpiperidin-1-yl)-oxazol-2-yl]-2-piperidin-1-yl-ethyl}-cyclohexyl)-thiophen-2-yl-methyl]-dimethylamine
75. benzyl-(4-benzyl-2-{2-[4-(dimethylaminothiophen-2-yl-methyl)-cyclohexyl]-1-piperidin-1-yl-ethyl}-oxazol-5-yl)-methylamine
76. [(4-{2-[4-benzyl-5-(4-phenylpiperazin-1-yl)-oxazol-2-yl]-2-piperidin-1-yl-ethyl}-cyclohexyl)-thiophen-2-yl-methyl]-dimethylamine
77. {1-[4-benzyl-5-(4-benzylpiperidin-1-yl)-oxazol-2-yl]-2-[4-(dimethylamino-thiophen-2-yl-methyl)-cyclohexyl]-ethyl}-diethylamine
78. {1-[4-benzyl-5-(4-benzylpiperazin-1-yl)-oxazol-2-yl]-2-[4-(dimethylamino-thiophen-2-yl-methyl)-cyclohexyl]-ethyl}-diethylamine
79. {1-[4-benzyl-5-(4-methylpiperidin-1-yl)-oxazol-2-yl]-2-[4-(dimethylamino-thiophen-2-yl-methyl)-cyclohexyl]-ethyl}-diethylamine
80. benzyl-(4-benzyl-2-{1-diethylamino-2-[4-(dimethylaminothiophen-2-yl-methyl)-cyclohexyl]-ethyl}-oxazol-5-yl)-methylamine
81. ({4-[2-[4-benzyl-5-(4-benzyl-piperidin-1-yl)-oxazol-2-yl]-2-(4-benzylpiperazin-1-yl)-ethyl]-cyclohexyl}-thiophen-2-yl-methyl)-dimethylamine
82. ({4-[2-[4-benzyl-5-(4-benzylpiperazin-1-yl)-oxazol-2-yl]-2-(4-benzylpiperazin-1-yl)-ethyl]-cyclohexyl}-thiophen-2-yl-methyl)-dimethylamine
83. ({4-[2-[4-benzyl-5-(4-methylpiperidin-1-yl)-oxazol-2-yl]-2-(4-benzylpiperazin-1-yl)-ethyl]-cyclohexyl}-thiophen-2-yl-methyl)-dimethylamine
84. benzyl-(4-benzyl-2-{1-(4-benzylpiperazin-1-yl)-2-[4-(dimethylaminothiophen-2-yl-methyl)-cyclohexyl]-ethyl}-oxazol-5-yl)-methylamine
85. ({4-[2-[4-benzyl-5-(4-phenylpiperazin-1-yl)-oxazol-2-yl]-2-(4-benzylpiperazin-1-yl)-ethyl]-cyclohexyl}-thiophen-2-yl-methyl)-dimethylamine
86. [4-benzyl-2-(2-{4-[(4-chlorophenyl)-dimethylaminomethyl]-cyclohexyl}-1-piperidin-1-yl-ethyl)-oxazol-5-yl]-methylphenethylamine
87. [4-benzyl-2-(2-{4-[(4-chlorophenyl)-dimethylaminomethyl]-cyclohexyl}-1-piperidin-1-yl-ethyl)-oxazol-5-yl]-diethylamine
88. (1-[4-benzyl-5-(3,5-dimethylpiperidin-1-yl)-oxazol-2-yl]-2-{4-[(4-chlorophenyl)-dimethylaminomethyl]-cyclohexyl}-ethyl)-diethylamine
89. [4-benzyl-2-(2-{4-[(4-chlorophenyl)-dimethylaminomethyl]-cyclohexyl}-1-diethylaminoethyl)-oxazol-5-yl]-methylphenethylamine
90. [4-benzyl-2-(2-{4-[(4-chlorophenyl)-dimethylaminomethyl]-cyclohexyl}-1-diethylaminoethyl)-oxazol-5-yl]-diethylamine
91. (1-(4-benzyl-5-thiomorpholin-4-yl-oxazol-2-yl)-2-{4-[(4-chlorophenyl)-dimethylaminomethyl]-cyclohexyl}-ethyl)-diethylamine
92. (1-(4-benzyl-5-thiomorpholin-4-yl-oxazol-2-yl)-2-{4-[(4-chlorophenyl)-dimethylaminomethyl]-cyclohexyl}-ethyl)-methylphenylamine
93. [4-benzyl-2-(1-(4-benzylpiperazin-1-yl)-2-{4-[(4-chlorophenyl)-dimethylaminomethyl]-cyclohexyl}-ethyl)-oxazol-5-yl]-methylphenethylamine
94. [4-benzyl-2-(1-(4-benzylpiperazin-1-yl)-2-{4-[(4-chlorophenyl)-dimethylaminomethyl]-cyclohexyl}-ethyl)-oxazol-5-yl]-diethylamine
95. [4-benzyl-2-(2-{4-[dimethylamino-(4-fluorophenyl)-methyl]-cyclohexyl}-1-piperidin-1-yl-ethyl)-oxazol-5-yl]-methylphenethylamine
96. (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-diethylamine
97. [4-benzyl-2-(1-diethylamino-2-{4-[dimethylamino-(4-fluorophenyl)-methyl]-cyclohexyl}-ethyl)-oxazol-5-yl]-methylphenethylamine
98. [4-benzyl-2-(1-diethylamino-2-{4-[dimethylamino-(4-fluorophenyl)-methyl]-cyclohexyl}-ethyl)-oxazol-5-yl]-diethylamine
99. (1-(4-benzyl-5-thiomorpholin-4-yl-oxazol-2-yl)-2-{4-[dimethylamino-(4-fluorophenyl)-methyl]-cyclohexyl}-ethyl)-diethylamine
100. (1-[4-benzyl-5-(3-methylpiperidin-1-yl)-oxazol-2-yl]-2-{4-[dimethylamino-(4-fluorophenyl)-methyl]-cyclohexyl}-ethyl)-diethylamine
101. (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-methylphenylamine
102. {4-benzyl-2-[2-{4-[dimethylamino-(4-fluorophenyl)-methyl]-cyclohexyl}-1-(methylphenylamine)-ethyl]-oxazol-5-yl}-methylphenethylamine 103. {4-benzyl-2-[2-{4-[dimethylamino-(4-fluorophenyl)-methyl]-cyclohexyl}-1-(methylphenylamine)-ethyl]-oxazol-5-yl}-diethylamine
104. (1-(4-benzyl-5-thiomorpholin-4-yl-oxazol-2-yl)-2-{4-[dimethylamino-(4-fluorophenyl)-methyl]-cyclohexyl}-ethyl)-methylphenylamine
105. (1-[4-benzyl-5-(3-methylpiperidin-1-yl)-oxazol-2-yl]-2-{4-[dimethylamino-(4-fluorophenyl)-methyl]-cyclohexyl}-ethyl)-methylphenylamine
106. [{4-[2-[4-benzyl-5-(3-methylpiperidin-1-yl)-oxazol-2-yl]-2-(4-benzylpiperazin-1-yl)-ethyl]-cyclohexyl}-(4-fluorophenyl)-methyl]-dimethylamine
107. [(4-{2-[4-benzyl-5-(3,5-dimethylpiperidin-1-yl)-oxazol-2-yl]-2-piperidin-1-yl-ethyl}-cyclohexyl)-thiophen-2-yl-methyl]-dimethylamine
108. (4-benzyl-2-{2-[4-(dimethylaminothiophen-2-yl-methyl)-cyclohexyl]-1-piperidin-1-yl-ethyl}-oxazol-5-yl)-methylphenethylamine
109. (4-benzyl-2-{2-[4-(dimethylaminothiophen-2-yl-methyl)-cyclohexyl]-1-piperidin-1-yl-ethyl}-oxazol-5-yl)-diethylamine
110. ({4-[2-(4-benzyl-5-thiomorpholin-4-yl-oxazol-2-yl)-2-piperidin-1-yl-ethyl]-cyclohexyl}-thiophen-2-yl-methyl)-dimethylamine
111. [(4-{2-[4-benzyl-5-(3-methylpiperidin-1-yl)-oxazol-2-yl]-2-piperidin-1-yl-ethyl}-cyclohexyl)-thiophen-2-yl-methyl]-dimethylamine
112. {1-[4-benzyl-5-(3,5-dimethylpiperidin-1-yl)-oxazol-2-yl]-2-[4-(dimethylamino-thiophen-2-yl-methyl)-cyclohexyl]-ethyl}-diethylamine
113. (4-benzyl-2-{1-diethylamino-2-[4-(dimethylaminothiophen-2-yl-methyl)-cyclohexyl]-ethyl}-oxazol-5-yl)-methylphenethylamine
114. (4-benzyl-2-{1-diethylamino-2-[4-(dimethylaminothiophen-2-yl-methyl)-cyclohexyl]-ethyl}-oxazol-5-yl)-diethylamine
115. {1-(4-benzyl-5-thiomorpholin-4-yl-oxazol-2-yl)-2-[4-(dimethylaminothiophen-2-yl-methyl)-cyclohexyl]-ethyl}-diethylamine
116. {1-[4-benzyl-5-(3-methylpiperidin-1-yl)-oxazol-2-yl]-2-[4-(dimethylaminothiophen-2-yl-methyl)-cyclohexyl]-ethyl}-diethylamine
117. {1-[4-benzyl-5-(3-methylpiperidin-1-yl)-oxazol-2-yl]-2-[4-(dimethylaminothiophen-2-yl-methyl)-cyclohexyl]-ethyl}-methylphenylamine
118. ({4-[2-(4-benzylpiperazin-1-yl)-2-(4-benzyl-5-thiomorpholin-4-yl-oxazol-2-yl)-ethyl]-cyclohexyl}-thiophen-2-yl-methyl)-dimethylamine
119. ({4-[2-[4-benzyl-5-(3-methylpiperidin-1-yl)-oxazol-2-yl]-2-(4-benzylpiperazin-1-yl)-ethyl]-cyclohexyl}-thiophen-2-yl-methyl)-dimethylamine
120. [{4-[(4-benzyl-5-pyrrolidin-1-yl-oxazol-2-yl)-morpholin-4-yl-methyl]-cyclohexyl}-(3-fluorophenyl)-methyl]-dimethylamine
121. [{4-[(4-benzyl-5-morpholin-4-yl-oxazol-2-yl)-morpholin-4-yl-methyl]-cyclohexyl}-(3-fluorophenyl)-methyl]-dimethylamine
122. [(4-{(4-benzyl-5-pyrrolidin-1-yl-oxazol-2-yl)-[4-(4-fluorophenyl)-piperazin-1-yl]-methyl}-cyclohexyl)-(3-fluorophenyl)-methyl]-dimethylamine
123. [(4-{(4-benzyl-5-pyrrolidin-1-yl-oxazol-2-yl)-[4-(4-methoxyphenyl)-piperazin-1-yl]-methyl}-cyclohexyl)-(3-fluorophenyl)-methyl]-dimethylamine
124. [(4-{(4-benzyl-5-morpholin-4-yl-oxazol-2-yl)-[4-(4-methoxyphenyl)-piperazin-1-yl]-methyl}-cyclohexyl)-(3-fluorophenyl)-methyl]-dimethylamine
125. [{4-[(4-benzyl-5-pyrrolidin-1-yl-oxazol-2-yl)-(3,4-dihydro-1H-isoquinolin-2-yl)-methyl]-cyclohexyl}-(3-fluorophenyl)-methyl]-dimethylamine
126. [{4-[(4-benzyl-5-morpholin-4-yl-oxazol-2-yl)-(3,4-dihydro-1H-isoquinolin-2-yl)-methyl]-cyclohexyl}-(3-fluorophenyl)-methyl]-dimethylamine
127. [{4-[{4-benzyl-5-[4-(4-methoxyphenyl)-piperazin-1-yl]-oxazol-2-yl}-(3,4-dihydro-1H-isoquinolin-2-yl)-methyl]-cyclohexyl}-(3-fluorophenyl)-methyl]-dimethylamine
128. [{4-[[4-benzyl-5-(2,6-dimethylmorpholin-4-yl)-oxazol-2-yl]-(3,4-dihydro-1H-isoquinolin-2-yl)-methyl]-cyclohexyl}-(3-fluorophenyl)-methyl]-dimethylamine
129. [{4-[(4-benzyl-5-pyrrolidin-1-yl-oxazol-2-yl)-morpholin-4-yl-methyl]-cyclohexyl}-(4-chlorophenyl)-methyl]-dimethylamine
130. [{4-[(4-benzyl-5-morpholin-4-yl-oxazol-2-yl)-morpholin-4-yl-methyl]-cyclohexyl}-(4-chlorophenyl)-methyl]-dimethylamine
131. [[4-({4-benzyl-5-[4-(4-methoxy-phenyl)-piperazin-1-yl]-oxazol-2-yl}-morpholin-4-yl-methyl)-cyclohexyl]-(4-chlorophenyl)-methyl]-dimethylamine
132. [(4-{[4-benzyl-5-(2,6-dimethylmorpholin-4-yl)-oxazol-2-yl]-morpholin-4-yl-methyl}-cyclohexyl)-(4-chlorophenyl)-methyl]-dimethylamine
133. [(4-{(4-benzyl-5-pyrrolidin-1-yl-oxazol-2-yl)-[4-(4-fluorophenyl)-piperazin-1-yl]-methyl}-cyclohexyl)-(4-chlorophenyl)-methyl]-dimethylamine
134. [(4-{(4-benzyl-5-pyrrolidin-1-yl-oxazol-2-yl)-[4-(4-methoxyphenyl)-piperazin-1-yl]-methyl}-cyclohexyl)-(4-chlorophenyl)-methyl]-dimethylamine
135. [(4-{(4-benzyl-5-morpholin-4-yl-oxazol-2-yl)-[4-(4-methoxyphenyl)-piperazin-1-yl]-methyl}-cyclohexyl)-(4-chlorophenyl)-methyl]-dimethylamine
136. [(4-{[4-benzyl-5-(2,6-dimethylmorpholin-4-yl)-oxazol-2-yl]-[4-(4-methoxy-phenyl)-piperazin-1-yl]-methyl}-cyclohexyl)-(4-chlorophenyl)-methyl]-dimethylamine
137. [{4-[(4-benzyl-5-pyrrolidin-1-yl-oxazol-2-yl)-(3,4-dihydro-1H-isoquinolin-2-yl)-methyl]-cyclohexyl}-(4-chlorophenyl)-methyl]-dimethylamine
138. ({4-[(4-benzyl-5-pyrrolidin-1-yl-oxazol-2-yl)-morpholin-4-yl-methyl]-cyclohexyl}-thiophen-2-yl-methyl)-dimethylamine
139. ({4-[(4-benzyl-5-morpholin-4-yl-oxazol-2-yl)-morpholin-4-yl-methyl]-cyclohexyl}-thiophen-2-yl-methyl)-dimethylamine
140. {[4-({4-benzyl-5-[4-(4-methoxyphenyl)-piperazin-1-yl]-oxazol-2-yl}-morpholin-4-yl-methyl)-cyclohexyl]-thiophen-2-yl-methyl}-dimethylamine
141. [(4-{[4-benzyl-5-(2,6-dimethylmorpholin-4-yl)-oxazol-2-yl]-morpholin-4-yl-methyl}-cyclohexyl)-thiophen-2-yl-methyl]-dimethylamine
142. [(4-{(4-benzyl-5-pyrrolidin-1-yl-oxazol-2-yl)-[4-(4-fluorophenyl)-piperazin-1-yl]-methyl}-cyclohexyl)-thiophen-2-yl-methyl]-dimethylamine
143. [(4-{(4-benzyl-5-pyrrolidin-1-yl-oxazol-2-yl)-[4-(4-methoxyphenyl)-piperazin-1-yl]-methyl}-cyclohexyl)-thiophen-2-yl-methyl]-dimethylamine
144. [(4-{(4-benzyl-5-morpholin-4-yl-oxazol-2-yl)-[4-(4-methoxyphenyl)-piperazin-1-yl]-methyl}-cyclohexyl)-thiophen-2-yl-methyl]-dimethylamine
145. [(4-{[4-benzyl-5-(2,6-dimethylmorpholin-4-yl)-oxazol-2-yl]-[4-(4-methoxy-phenyl)-piperazin-1-yl]-methyl}-cyclohexyl)-thiophen-2-yl-methyl]-dimethylamine 146. ({4-[(4-benzyl-5-pyrrolidin-1-yl-oxazol-2-yl)-(3,4-dihydro-1H-isoquinolin-2-yl)-methyl]-cyclohexyl}-thiophen-2-yl-methyl)-dimethylamine
147. ({4-[{4-benzyl-5-[4-(4-methoxyphenyl)-piperazin-1-yl]-oxazol-2-yl}-(3,4-dihydro-1H-isoquinolin-2-yl)-methyl]-cyclohexyl}-thiophen-2-yl-methyl)-dimethylamine
148. ({4-[[4-benzyl-5-(2,6-dimethylmorpholin-4-yl)-oxazol-2-yl]-(3,4-dihydro-1H-isoquinolin-2-yl)-methyl]-cyclohexyl}-thiophen-2-yl-methyl)-dimethylamine
149. [{4-[2-(4-benzyl-5-pyrrolidin-1-yl-oxazol-2-yl)-2-morpholin-4-yl-ethyl]-cyclohexyl}-(3-fluorophenyl)-methyl]-dimethylamine
150. [{4-[2-(4-benzyl-5-morpholin-4-yl-oxazol-2-yl)-2-morpholin-4-yl-ethyl]-cyclohexyl}-(3-fluorophenyl)-methyl]-dimethylamine
151. [[4-(2-{4-benzyl-5-[4-(4-methoxyphenyl)-piperazin-1-yl]-oxazol-2-yl}-2-morpholin-4-yl-ethyl)-cyclohexyl]-(3-fluorophenyl)-methyl]-dimethylamine
152. [(4-{2-[4-benzyl-5-(2,6-dimethylmorpholin-4-yl)-oxazol-2-yl]-2-morpholin-4-yl-ethyl}-cyclohexyl)-(3-fluorophenyl)-methyl]-dimethylamine
153. [(4-{2-[4-benzyl-5-(2,6-dimethylmorpholin-4-yl)-oxazol-2-yl]-2-[4-(4-fluorophenyl)-piperazin-1-yl]-ethyl}-cyclohexyl)-(3-fluorophenyl)-methyl]-dimethylamine
154. [(4-{2-(4-benzyl-5-morpholin-4-yl-oxazol-2-yl)-2-[4-(4-methoxyphenyl)-piperazin-1-yl]-ethyl}-cyclohexyl)-(3-fluorophenyl)-methyl]-dimethylamine
155. [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-(3-fluorophenyl)-methyl]-dimethylamine
156. [(4-{2-[4-benzyl-5-(2,6-dimethylmorpholin-4-yl)-oxazol-2-yl]-2-[4-(4-methoxy-phenyl)-piperazin-1-yl]-ethyl}-cyclohexyl)-(3-fluorophenyl)-methyl]-dimethylamine
157. [{4-[2-{4-benzyl-5-[4-(4-methoxyphenyl)-piperazin-1-yl]-oxazol-2-yl}-2-(3,4-dihydro-1H-isoquinolin-2-yl)-ethyl]-cyclohexyl}-(3-fluorophenyl)-methyl]-dimethylamine
158. ({4-[2-(4-benzyl-5-morpholin-4-yl-oxazol-2-yl)-2-morpholin-4-yl-ethyl]-cyclohexyl}-thiophen-2-yl-methyl)-dimethylamine
159. {[4-(2-{4-benzyl-5-[4-(4-methoxyphenyl)-piperazin-1-yl]-oxazol-2-yl}-2-morpholin-4-yl-ethyl)-cyclohexyl]-thiophen-2-yl-methyl}-dimethylamine
160. [(4-{2-[4-benzyl-5-(2,6-dimethylmorpholin-4-yl)-oxazol-2-yl]-2-morpholin-4-yl-ethyl}-cyclohexyl)-thiophen-2-yl-methyl]-dimethylamine
161. [(4-{2-(4-benzyl-5-morpholin-4-yl-oxazol-2-yl)-2-[4-(4-fluorophenyl)-piperazin-1-yl]-ethyl}-cyclohexyl)-thiophen-2-yl-methyl]-dimethylamine
162. [(4-{2-{4-benzyl-5-[4-(4-methoxyphenyl)-piperazin-1-yl]-oxazol-2-yl}-2-[4-(4-fluorophenyl)-piperazin-1-yl]-ethyl}-cyclohexyl)-thiophen-2-yl-methyl]-dimethylamine
163. [(4-{2-(4-benzyl-5-pyrrolidin-1-yl-oxazol-2-yl)-2-[4-(4-methoxyphenyl)-piperazin-1-yl]-ethyl}-cyclohexyl)-thiophen-2-yl-methyl]-dimethylamine
164. [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-thiophen-2-yl-methyl]-dimethylamine
165. [(4-{2-[4-benzyl-5-(2,6-dimethylmorpholin-4-yl)-oxazol-2-yl]-2-[4-(4-methoxy-phenyl)-piperazin-1-yl]-ethyl}-cyclohexyl)-thiophen-2-yl-methyl]-dimethylamine
166. ({4-[2-{4-benzyl-5-[4-(4-methoxyphenyl)-piperazin-1-yl]-oxazol-2-yl}-2-(3,4-dihydro-1H-isoquinolin-2-yl)-ethyl]-cyclohexyl}-thiophen-2-yl-methyl)-dimethylamine The invention also provides a method for the preparation of an oxazole derivative according to the invention. The substances according to the invention can be prepared by heating aldehydes of the general Formula A with amines of the general Formula B and isonitrile amides of the general Formula C in an organic solvent, for example methanol or ethanol, for 1 to 10 hours at a temperature between 30° and 100° C., preferably 40 to 80° C.

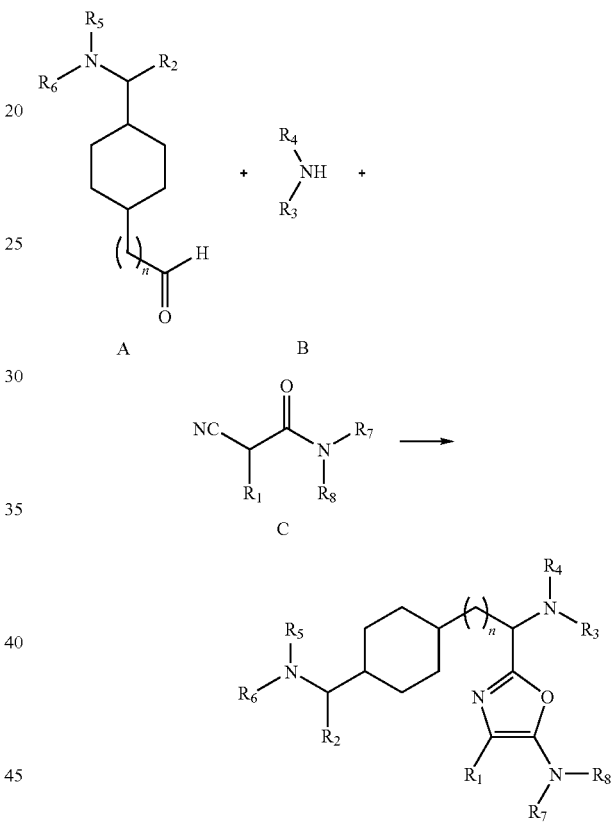

The component C can be prepared analogously to the synthesis described in K. Numani et al, Agric. Biol. Chem. 1985, 49, 10, 3023-3028 according to the following reaction scheme. After preparation of the corresponding amino acid ester, as described in V. Wehner et al., Tetrahedron 2004, 60, 19, 4295-4302, the isonitrile ester is formed under dehydrating conditions. After subsequently reacting the ester with an amine, the desired isonitrile amide is obtained.

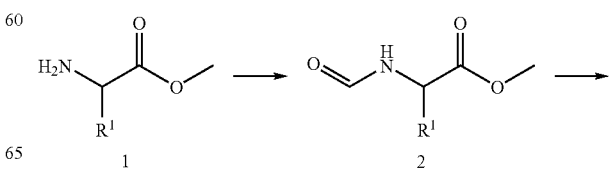

-continued

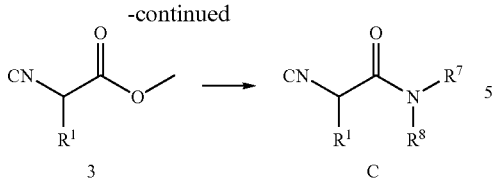

The amines of the general Formula B are commercially obtainable or can be prepared by methods known to the person skilled in the art.

In order to prepare the aldehydes of the general Formula A, the keto function of 4-oxo-cyclohexanecarboxylic acid esters,

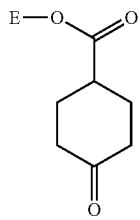

where E denotes a $C_{1-6}$-alkyl radical, preferably ethyl, is protected by methods known to those skilled in the art

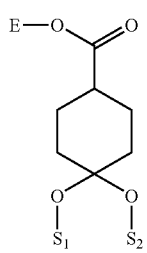

10

$S_1$ and $S_2$ each denote a protective group, preferably form a ring, and together denote —$CH_2$—$CH_2$—. The ester 10 is reduced with a reducing agent, for example diisobutyl aluminium hydride to form the aldehyde 11.

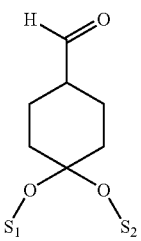

11

By adding an amine of the general Formula $R^5R^6NH$ and a cyanide, for example KCN or NaCN, the aldehyde 11 is converted under the addition of an acid, for example hydrochloric acid, in an organic solvent, for example methanol or ethanol, to the nitrile 12.

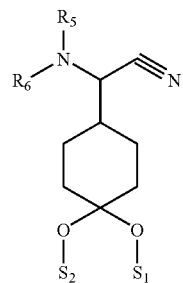

12

The nitrile 12 is reacted with a Grignard reagent of the general Formula $R^2MgHal$, where Hal denotes Br, Cl or I, or an organometallic compound of the general Formula $R^2Li$ in an organic solvent, for example diethyl ether, dioxane or tetrahydrofuran, to form a compound of the general Formula 13.

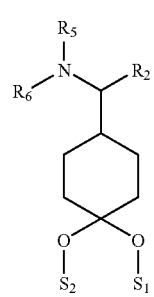

13

The protective groups are split off by conventional methods to obtain the ketone 14.

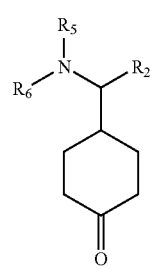

14

The aldehyde 15

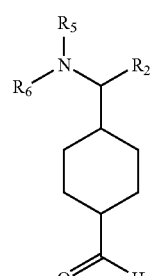

15 is obtained by reacting the ketone 14 with (methoxymethyl) triphenylphosphonium chloride and a strong base, for example potassium tert-butylate, at a temperature from −20° C. to +30° C.

By reacting the aldehyde 15 with (methoxymethyl)triphenylphosphonium chloride and a strong base, for example potassium tert-butylate, at a temperature from −20° C. to +30° C., an aldehyde of the general Formula 16 is obtained.

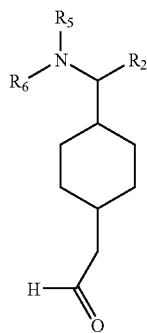

16

By repeating the last reaction step aldehydes can be obtained in which n is 2.

The substances according to the invention are suitable as pharmaceutical active substances in medicaments. The invention accordingly also provides medicaments containing at least one substituted oxazole derivatives according to the invention, as well as optionally suitable additives and/or auxiliary substances and/or optionally further active substances.

The medicaments according to the invention contain, in addition to at least one substituted oxazole derivative according to the invention, optionally also suitable additives and/or auxiliary substances, thus also carrier materials, fillers, solvents, diluents, colorants and/or binders, and can be administered as liquid medicament in the form of injection solutions, drops or juices, or as semi-solid medicament in the form of granules, tablets, pellets, patches, capsules, plasters or aerosols. The choice of the auxiliary substances, etc. as well as the amounts thereof to be employed depends on whether the medicament is to be administered orally, parenterally, intravenously, intraperitoneally, intradermally, intramuscularly, intranasally, buccally, rectally or topically, for example to the skin, mucus membranes or the eyes. For oral application suitable preparations are in the form of tablets, pills, capsules, granules, drops, juices and syrups, while for parenteral, topical and inhalative application suitable preparations are solutions, suspensions, easily reconstitutable dry preparations as well as sprays. Oxazole derivatives according to the invention in a depot form, in dissolved form or in a plaster, optionally with the addition of agents promoting penetration of the skin, are suitable percutaneous application forms. Orally or percutaneously employable preparation forms can release the oxazole derivatives according to the invention in a delayed manner. In principle other active substances known to the person skilled in the art can also be added to the medicaments according to the invention.

The amount of active substance to be administered to the patient varies depending on the patient's weight, type of application, medical indications and the severity of the disease. Normally 0.005 to 20 mg/kg, preferably 0.05 to 5 mg/kg of at least one oxazole derivative according to the invention are administered. The medicament can contain an oxazole derivative according to the invention as pure diastereomer and/or enantiomer, as racemate, or as a non-equimolar or equimolar mixture of the diastereomers and/or enantiomers.

The invention also provides for the use of an oxazole derivative according to the invention for the treatment of pain or preparation of a medicament for treating pain, in particular acute, neuropathic or chronic pain.

The invention also provides for the use of an oxazole derivative according to the invention for the treatment of depression or the preparation of a medicament for treating depression and/or anxiety.

In addition the substituted oxazole derivatives of the general Formula I can be used to treat urinary incontinence, diarrhoea, pruritus, alcohol and drug misuse, drug dependence and lack of drive or lethargy.

The invention accordingly also provides for the use of a substituted oxazole derivative of the general Formula I for the preparation of a medicament for treating urinary incontinence, diarrhoea, pruritus, alcohol and drug misuse, drug dependence and lack of drive or lethargy.

EXAMPLES

Preparation of the Isonitrile Amide

Methyl 2-(formylamino)-3-phenylpropanoate 2i

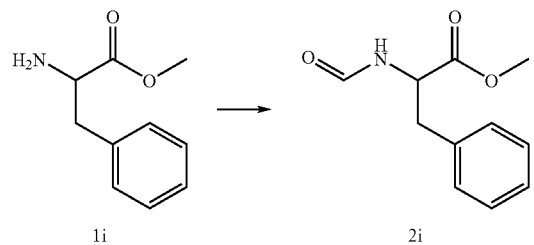

Cyanomethyl formate (Aldrich, Order No. 453579, 5.05 g, 59.3 mmole) was suspended together with the phenylalanine methyl ester hydrochloride (Aldrich, Order No. 525472, 12.80 g, 59.3 mmole) in 80 ml dichloromethane and cooled to 0° C. in an ice bath. Triethylamine (6.01 g, 59.3 mmole) dissolved in 15 ml of dichloromethane was then added and the mixture was stirred for 16 hours at room temperature. A clear solution formed. In order to work up the mixture the latter was diluted with 100 ml of dichloromethane and washed firstly with 200 ml of saturated $NaHCO_3$ solution and then twice with saturated NaCl solution. The organic phase was dried over magnesium sulfate and concentrated by evaporation. The product obtained was used without further purification for the next stage.

Yield: 12.5 g colorless oil $^1$H-NMR (300 MHz, $CDCl_3$): δ=3.07-3.22 (m, 2H); 3.74 (s, 3H); 4.92-5.01 (m, 1H); 6.20 (bs, 1H); 7.07-7.15 (m, 2H); 7.23-7.34 (m, 3H); 8.15 (s, 1H).

Methyl 2-isocyano-3-phenylpropionate 3i

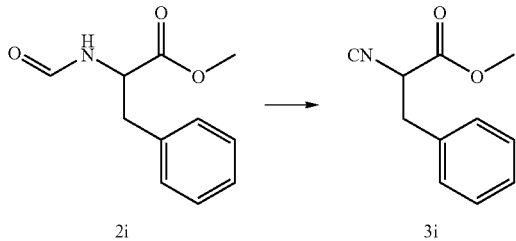

Methyl 2-(formylamino)-3-phenylpropanoate 2i (2.00 g, 9.7 mmole) was dissolved in 20 ml of dichloromethane and cooled to 0° C. After addition of triethylamine (4.88 g, 48.3 mmole), phosphorous oxychloride (2.22 g, 14.5 mmole) dissolved in 10 ml of dichloromethane was then slowly added dropwise. The initially colorless solution turned yellow, with the formation finally of an orange solid. After stirring for 1 hour in an ice bath potassium carbonate solution (0.8 M in water, 39 ml) was slowly added dropwise. To work up the mixture the phases were separated. The organic phase was first of all washed twice with water, each time 20 ml, and then once with 20 ml of saturated NaCl solution. The solution was dried over sodium sulfate and concentrated by evaporation. The product was used without further purification for the next stage.

Yield: m=1.55 g of orange-brown liquid $^1$H-NMR (300 MHz, CDCl$_3$): δ=3.14 (dd, 1H, J$_{AA'}$=8.66 Hz, J$_{AB}$=8.29 Hz); 3.23 (dd, 1H, J$_{AA'}$=4.52 Hz, J$_{AB}$=4.90 Hz); 3.80 (s, 3H), 4.46 (dd, 1H, J=8.29; J=4.90 Hz); 7.22-7.39 (m, 5H).

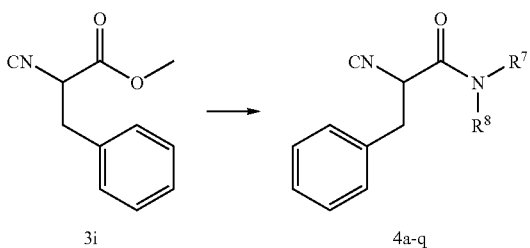

General Procedure:

Methyl 2-isocyano-3-phenyl-propionate 3i (13 g, 68.71 mmole) and the corresponding amine (137.42 mmole) were mixed together and stirred at room temperature. After completion of the reaction (TLC check) the product was first of all concentrated by evaporation on a rotary evaporator and then purified by column chromatography (solvent: gradient: hexane to ether:hexane=1:1)

1-[(2R)-2-isocyano-3-phenylpropanoyl]piperidine 4a (NR$^7$R$^8$=piperidinyl)

$^1$H-NMR (300 MHz, CDCl$_3$): δ=1.26-1.44 (m, 1H); 1.46-1.73 (m, 5H); 3.10-3.34 (m, 2H); 3.35-3.56 (m, 2H); 3.57-3.69 (m, 1H); 4.66 (dd, 1H, J=6.03 Hz, J=9.0 Hz); 7.23-7.39 (m, 5H).

1-[(2R)-2-isocyano-3-phenylpropanoyl]pyrrolidine 4b (NR$^7$R$^8$=pyrrolidinyl)

$^1$H-NMR (300 MHz, CDCl$_3$): δ=1.70-1.99 (m, 4H); 2.98-3.11 (m, 1H); 3.12-3.35 (m, 2H); 3.36-3.59 (m, 3H); 4.40 (dd, 1H, JA,B=7.53 Hz, JA,B'=7.16 Hz); 7.23-7.38 (m, 5H).

4-[(2R)-2-isocyano-3-phenylpropanoyl]morpholine 4c (NR$^7$R$^8$=morpholinyl)

$^1$H-NMR (300 MHz, CDCl$_3$): δ=3.13-3.52 (m, 5H); 3.52-3.80 (m, 5H); 4.47-4.61 (m, 1H); 7.19-7.43 (m, 5H).

(2R)-1-(4-benzylpiperidin-1-yl)-2-isocyano-3-phenylpropan-1-one 4d (NR$^7$R$^8$=4-benzylpiperidinyl)

$^{13}$C-NMR (75 MHz, CDCl$_3$) both diastereomers: δ=31.45, 31.80 (t); 37.77, 38.18 (d); 38.82, 39.25 (t); 42.68, 42.73 (t); 43.21 (t); 46.11, 46.34 (t); 55.10, 55.60 (d); 126.15 (d); 127.51, 127.60 (d); 128.36 (d); 128.74, 128.87 (d); 129.01, 129.05 (d); 129.39, 129.51 (d); 135.32, 135.53 (s); 139.55, 139.71 (s); 162.86, 163.07 (s).

(2R)-1-(4-benzylpiperazin-1-yl)-2-isocyano-3-phenylpropan-1-one 4e (NR$^7$R$^8$=4-benzylpiperazinyl)

$^{13}$C-NMR (75 MHz, CDCl$_3$): δ=38.95 (t); 42.73 (t); 45.93 (t); 52.32 (t); 55.33 (d); 62.66 (t); 127.37 (d); 127.67 (d); 128.38 (d); 128.84 (d); 129.07 (d); 129.41 (d); 135.25 (s); 137.36 (s); 163.12 (s).

(2R)-2-isocyano-1-(4-methylpiperidin-1-yl)-3-phenylpropan-1-one 4f (NR$^7$R$^8$=4-methylpiperidinyl)

$^{13}$C-NMR (75 MHz, CDCl$_3$) both diastereomers: δ=21.47 (q); 21.51 (q); 30.68 (d); 30.96 (d); 33.42 (t); 33.82 (t); 33.94 (t); 38.83 (t); 39.20 (t); 43.26 (t); 43.29 (t); 46.17 (t); 46.37 (t); 55.18 (d); 55.64 (d); 127.50 (d); 127.57 (d); 128.75 (d); 128.84 (d); 129.40 (d); 129.47 (d); 135.36 (s); 135.58 (s); 162.88 (s); 163.07 (s).

(2R)—N-benzyl-2-isocyano-N-methyl-3-phenylpropanamide 4g (R$^7$=methyl, R$^8$=benzyl)

$^1$H-NMR (300 MHz, CDCl$_3$): δ=2.85 (s, 3H); 3.11-3.40 (m, 2H); 4.30-4.66 (m, 3H); 7.12-7.21 (m, 2H); 7.24-7.39 (m, 8H).

(2R)-2-isocyano-3-phenyl-1-(4-phenylpiperazin-1-yl)-propan-1-one 4h (NR$^7$R$^8$=4-phenylpiperazinyl)

$^1$H-NMR (300 MHz, CDCl$_3$): δ=3.06-3.90 (m, 10H); 4.60 (dd, 1H, J=6.78 Hz, J=6.0 Hz); 6.83-6.98 (m, 3H); 7.22-7.42 (m, 7H).

1-(3,5-dimethylpiperidin-1-yl)-2-isocyano-3-phenyl-propan-1-one 4l (NR$^7$R$^3$=3,5-dimethylpiperidinyl)

$^1$H-NMR (300 MHz, CDCl$_3$) both diastereomers: δ=0.68-0.80 (m, 2H); 0.80-0.96 (m, 12H); 0.99-1.14 (m, 1H); 1.38-1.53 (m, 1H); 1.63-1.90 (m, 4H); 1.97-2.13 (m, 2H); 2.31-2.44 (m, 1H); 2.49-2.61 (m, 1H); 3.10-3.67 (m, 6H); 4.48-4.63 (m, 4H); 7.21-7.40 (m, 10H).

(2R)-2-isocyano-N-methyl-N-phenethyl-3-phenyl-propionamide 4j (R$^7$=methyl, R$^8$=2-phenylethyl)

$^{13}$C-NMR (75 MHz, CDCl$_3$) both rotamers: δ=33.31 (t); 36.18 (q); 38.66 (t); 38.82 (t); 51.04 (t); 51.36 (t); 54.97 (d); 55.66 (d); 126.59 (d); 127.24 (d); 127.45 (d); 127.59 (d);

128.64 (d); 128.78 (d); 128.83 (d); 129.10 (d); 129.36 (d); 129.41 (d); 135.35 (s); 137.51 (s); 138.41 (s); 164.36 (s); 164.82 (s).

(2R)—N,N-diethyl-2-isocyano-3-phenylpropionamide 4k ($R^7$=ethyl, $R^8$=ethyl)

$^1$H-NMR (300 MHz, CDCl$_3$): δ=1.10 (t, 3H, J=7.16 Hz); 1.11 (t, 3H, J=7.16 Hz); 3.09-3.47 (m, 6H); 4.49 (t, 1H, J=7.16 Hz); 7.22-7.38 (m, 5H).

4-[(2R)-2-isocyano-3-phenylpropanoyl]thiomorpholine 4l ($NR^7R^8$=thiomorpholinyl)

$^1$H-NMR (300 MHz, CDCl$_3$): δ=2.24-2.40 (m, 1H), 2.43-2.65 (m, 3H); 2.94-3.17 (m, 2H); 3.64-3.81 (m, 4H); 5.28 (dd, 1H, J=8.67 Hz, J=6.03 Hz); 7.24-7.39 (m, 5H).

1-[(2S)-2-isocyano-3-phenylpropanoyl]-4-(4-methoxyphenyl)piperazine 4m ($NR^7R^8$=1-(4-methoxyphenyl)piperazinyl $^1$H-NMR (300 MHz, CDCl$_3$): δ=2.74-2.83 (m, 1H); 2.93-3.10 (m, 3H); 3.13-3.88 (m, 7H); 3.77 (s, 3H); 4.60 (dd, 1H, J=8.10 Hz, J=6.59 Hz); 6.84-6.86 (m, 4H); 7.26-7.38 (m, 5H).

1-[2-isocyano-3-phenylpropanoyl]-3-methylpiperidine 4n ($NR^7R^8$=3-methylpiperidinyl)

$^1$H-NMR (300 MHz, CDCl$_3$) diastereomers and rotamers: δ=0.82-0.94 (m, 3H); 1.01-1.91 (m, 5H); 2.20-3.76 (m, 4H); 4.28-4.65 (m, 2H); 7.23-7.39 (m, 5H).

2-isocyano-1-morpholin-4-yl-3-phenylpropan-1-one 4o ($NR^7R^8$=2,6-dimethylmorpholinyl)

$^1$H-NMR (300 MHz, CDCl$_3$) diasteromers and rotamers: δ=1.04-1.27 (m, 6H); 2.26-3.80 (m, 8H); 4.34-4.63 (m, 2H); 7.16-7.39 (m, 5H).

1-[4-(2-fluorophenyl)-piperazin-1-yl]-2-isocyano-3-phenylpropan-1-one 4p ($NR^7R^8$=1-(2-fluorophenyl)piperazinyl)

$^1$H-NMR (300 MHz, CDCl$_3$): δ=2.77-2.85 (m, 1H); 2.96-3.10 (m, 3H); 3.16-3.37 (m, 2H); 3.38-3.50 (m, 1H); 3.59-3.77 (m, 2H); 3.83-3.92 (m, 1H); 4.60 (dd, 1H, J=8.10 Hz, J=6.59 Hz), 6.84-6.91 (m, 1H); 6.96-7.10 (m, 3H); 7.26-7.39 (m, 5H).

1-[4-(4-fluorophenyl)-piperazin-1-yl]-2-isocyano-3-phenylpropan-1-one 4q ($NR^7R^8$=1-(4-fluorophenyl)piperazinyl)

$^1$H-NMR (300 MHz, CDCl$_3$): δ=2.77-2.85 (m, 1H); 3.00-3.11 (m, 3H); 3.17-3.46 (m, 3H); 3.57-3.77 (m, 2H); 3.80-3.89 (m, 1H); 4.60 (dd, 1H, J=8.10 Hz, J=6.78 Hz), 6.82-6.88 (m, 2H); 6.94-7.01 (m, 2H); 7.25-7.39 (m, 5H).

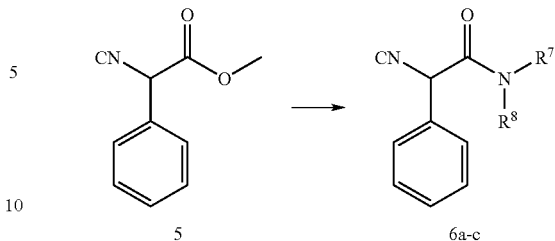

General Procedure:
Methyl 2-isocyano-2-phenylacetate 5 (13 g, 68.71 mmole) and the corresponding amine (137.42 mmole) were mixed together and stirred at room temperature. After completion of the reaction (TLC check) the mixture was first of all concentrated by evaporation on a rotary evaporator and then purified by column chromatography (solvent: gradient:hexane to ether:hexane=1:1)

2-isocyano-2-phenyl-1-pyrrolidin-1-yl-ethanone 6a ($NR^7R^8$=pyrrolidinyl)

$^1$H-NMR (300 MHz, CDCl$_3$): δ=1.74-1.99 (m, 4H); 3.25-3.63 (m, 4H); 5.51 (s, 1H); 7.38-7.53 (m, 5H).

2-isocyano-1-morpholin-4-yl-2-phenylethanone 6b ($NR^7R^8$=morpholinyl)

$^1$H-NMR (300 MHz, CDCl$_3$): δ=3.30-3.48 (m, 4H); 3.59-3.70 (m, 4H); 5.66 (s, 1H); 7.37-7.50 (m, 5H).

2-isocyano-2-phenyl-1-(piperidin-1-yl)ethanone 6c ($NR^7R^8$=piperidinyl)

$^1$H-NMR (300 MHz, CDCl$_3$): δ=1.22-1.36 (m, 2H); 1.47-1.65 (m, 4H); 3.29 (t, J=4.90 Hz, 2H); 3.50-3.65 (m, 2H); 5.67 (s, 1H); 7.36-7.46 (m, 5H).

3-(4-chlorophenyl)-2-isocyano-1-piperidin-1-yl-propan-1-one 8

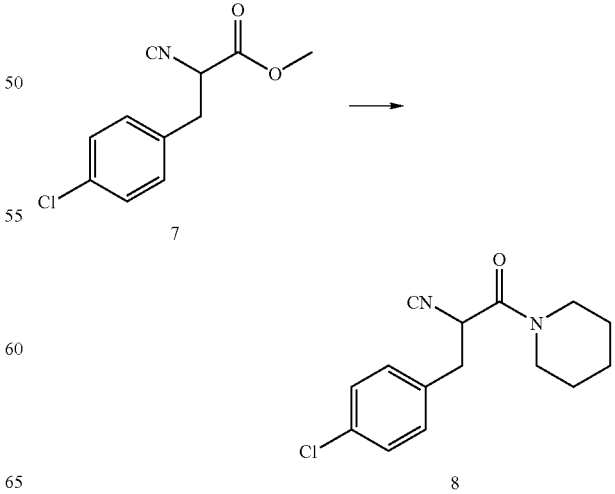

Methyl 2-isocyano-2-(4-chlorophenyl)propionate 7 (Priaton, Order No. 224.8 g, 35.87 mmole) and piperidine (6.1 µg, 71.74 mmole) were mixed together and stirred at room temperature. After completion of the reaction (TLC check) the mixture was first of all concentrated by evaporation on a rotary evaporator and then purified by column chromatography (solvent: gradient:hexane to ether:hexane=1:1)

$^1$H-NMR (300 MHz, CDCl$_3$): δ=1.38-1.77 (m, 6H); 3.08-3.35 (m, 3H); 3.41-3.53 (m, 2H); 3.61-3.73 (m, 1H); 4.50 (dd, 1H, J=8.29 Hz, J=6.03 Hz); 7.19-7.34 (m, 4H).

Synthesis of the Aldehydes

The aldehydes 15a-e and 16a-e were obtained in the way described below in a multi-stage synthesis from the commercially obtainable 4-oxo-cyclohexane-carboxylic acid ethyl ester. The yields of the prepared compounds are not optimized. All temperatures are uncorrected.

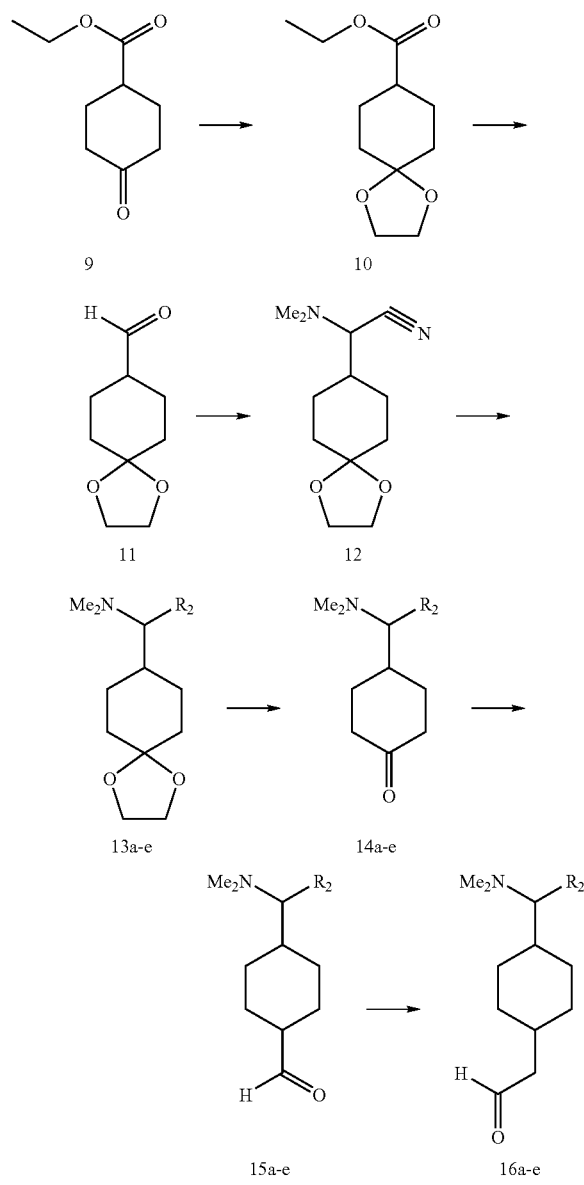

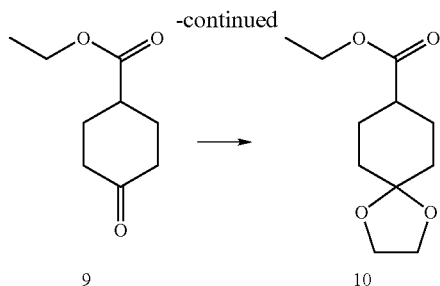

1,4-dioxa-spiro[4.5]decane-8-carboxylic acid ethyl ester 10

4-oxocyclohexane carboxylic acid ethyl ester 9 (52.8 g, 0.31 mole, Merck, Order No. 814249), ethylene glycol (67.4 g, 1.08 mol) and p-toluenesulfonic acid (0.7 g) in toluene (160 ml) were stirred for 20 hours at RT, and the reaction solution was poured into diethyl ether (300 ml) and washed with water, sodium hydrogen carbonate solution and sodium chloride solution. The solution was dried (Na$_2$SO$_4$), concentrated by evaporation in vacuo, and the remaining colorless liquid was processed further without purification.

Yield: 66.5 g (100%) $^1$H-NMR (CDCl$_3$): 1.24 (t, 3H); 1.53 (m, 2H); 1.76 (m, 4H); 1.92 (m, 2H); 2.31 (m, 1H); 3.91 (s, 4H); 4.11 (q, 2H). $^{13}$C-NMR (CDCl$_3$): 14.28 (q); 26.32 (t); 33.76 (t); 41.59 (d); 60.14 (t); 64.21 (t); 107.90 (d); 174.77 (s).

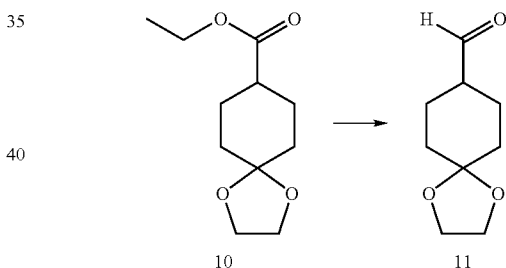

1,4-dioxa-spiro[4.5]decane-8-carbaldehyde 11

Diisobutyl aluminium hydride (1.5 M solution in toluene, 102 ml, 153 mmole) was added dropwise to a solution of 1,4-dioxa-spiro[4.5]decane-8-carboxylic acid ethyl ester 10 (32.13 g, 150 mmole) in absolute toluene (160 ml) under argon at −70° to −65° C. and stirred for 30 minutes. The reaction mixture was then quenched at −70° to −60° C. by adding methanol (80 ml). The reaction solution was heated to RT, sodium chloride solution (100 ml) was added, and the reaction solution was suction filtered through diatomaceous earth. The diatomaceous earth was washed twice with ethyl acetate, and the aqueous solution was separated and extracted twice with ethyl acetate. The combined organic extracts were washed with saturated sodium chloride solution, dried over sodium sulfate and concentrated by evaporation in vacuo.

Yield: 24.01 g (94%), yellow oil $^1$H-NMR (CDCl$_3$): 1.54 (m, 2H); 1.74 (m, 4H); 1.91 (m, 2H); 2.21 (m, 1H); 3.91 (s, 4H); 9.60 (s, 1H). $^{13}$C-NMR (CDCl$_3$): 23.35 (t); 33.37 (t); 48.18 (d); 64.30 (t); 107.89 (d); 203.51 (s).

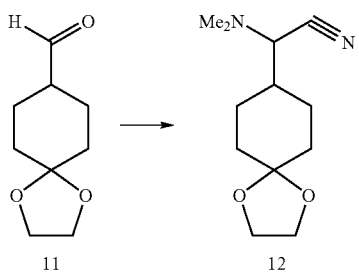

Dimethylamino-(1,4-dioxa-spiro[4.5]dec-8-yl)-acetonitrile 12

40% aqueous dimethylamine solution (85 ml, 0.67 mole), 1,4-dioxa-spiro-[4.5]decane-8-carbaldehyde 11 (240 g, 0.141 mole) and potassium cyanide (22.05 g, 0.338 mole) were added dropwise to a mixture of 4N hydrochloric acid (37 ml) and methanol (22 ml) while cooling with ice. The mixture was stirred for 4 days at room temperature and was then extracted with diethyl ether (4×100 ml) after adding water (80 ml). The organic phase was dried over sodium sulfate, concentrated by evaporation in vacuo, and the product was obtained as a white solid.

Yield: 25.2 g (81%) m.p.: 48-51° C. $^1$H-NMR (CDCl$_3$): 1.23-2.03 (m, 9H); 2.28 (s, 6H); 3.16 (d, 1H); 3.93 (m, 4H). $^{13}$C-NMR (CDCl$_3$): 26.67 (t); 27.93 (t); 33.87 (t); 36.94 (d); 41.90 (q); 64.30 (t); 64.36 (t); 108.33 (d); 115.94 (s).

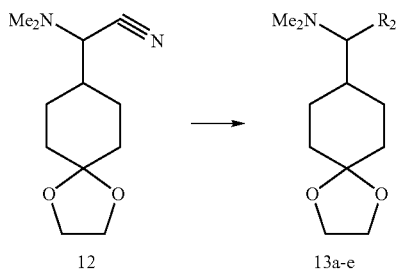

[(1,4-dioxa-spiro[4.5]dec-8-yl)-4-fluorophenylmethyl]-dimethylamine 13a (R$^2$=4-fluorophenyl)

A solution of the aminonitrile 12 (19.89 g, 88 mmole) in absolute THF (160 ml) was added dropwise to a 1M solution of 4-fluorophenyl magnesium bromide in THF (220 ml, 220 mmole) under argon and while cooling with ice, and stirred for 20 hours at RT. To work up the reaction mixture saturated ammonium chloride solution (100 ml) and water (100 ml) were added while cooling with ice and the mixture was extracted with diethyl ether (3×100 ml). The organic phase was washed with water and saturated sodium chloride solution, dried (Na$_2$SO$_4$) and concentrated by evaporation.

Yield: 31 g (>100%) $^{13}$C-NMR (CDCl$_3$): 26.68 (t); 28.11 (t); 34.43 (t); 34.55 (t); 37.37 (d); 41.68 (q); 64.12 (t); 73.65 (d); 108.88 (d); 114.23 (d); 114.44 (d); 130.27; 130.35; 132.43; 160.36 (s); 162.78 (s).

[(1,4-dioxa-spiro[4.5]dec-8-yl)-3-fluorophenylmethyl]-dimethylamine 13b (R$^2$=3-fluorophenyl)

A solution of the aminonitrile 12 (23.45 g, 104 mmole) in absolute THF (100 ml) was added dropwise to a 1M solution of 3-fluorophenyl magnesium bromide in THF (208 ml, 208 mmole) under argon and while cooling with ice, and stirred for 20 hours at RT. To work up the reaction mixture saturated ammonium chloride solution (100 ml) and water (100 ml) were added while cooling with ice and the mixture was extracted with diethyl ether (3×100 ml). The organic phase was washed with water and saturated sodium chloride solution, dried and concentrated by evaporation.

Yield: 30.33 g (99%). $^1$H-NMR (CDCl$_3$): 1.12 (m, 1H); 1.26 (m, 1H); 1.46-1.81 (m, 7H); 2.10 (s, 6H); 3.10 (d, 1H); 3.90 (m, 4H); 6.85 (m, 3H); 7.27 (m, 1H). $^{13}$C-NMR (CDCl$_3$): 26.80 (t); 28.08 (t); 34.48 (t); 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(4-chlorophenyl)-(1,4-dioxa-spiro[4.5]dec-8-yl)-methyl]-dimethylamine 13c (R$^2$=4-chlorophenyl)

A solution of the aminonitrile 12 (22.43 g, 100 mmole) in absolute ether (100 ml) was added dropwise to a 1M solution of 4-chlorophenyl magnesium bromide in ether (200 ml, 200 mmole) and stirred for 20 hours at RT. To work up the reaction mixture saturated ammonium chloride solution (100 ml) and water (100 ml) were added while cooling with ice and the mixture was extracted with diethyl ether (3×100 ml). The organic phase was washed with water and saturated sodium chloride solution, dried, and concentrated by evaporation.

Yield: 30.9 g (100%) $^{13}$C-NMR (CDCl$_3$): 26.65 (t); 28.11 (t); 34.46 (t); 34.60 (t); 37.28 (d); 41.76 (q); 64.17 (t); 73.80 (d); 108.88 (s); 127.72 (d); 129.53 (d); 132.39 (d); 135.33 (d).

[(1,4-Dioxa-spiro[4.5]dec-8-yl)-thiophen-2-yl-methyl]-dimethylamine 13d (R$^2$=2-thienyl)

A solution of the aminonitrile 12 (2.24 g, 10 mmole) in absolute THF (10 ml) was added dropwise to a 1M solution of thiophen-2-yl-magnesium bromide in THF (20 ml, 20 mmole) under argon and while cooling with ice, and stirred for 20 hours at RT. To work up the reaction mixture saturated ammonium chloride solution (10 ml) and water (10 ml) were added while cooling with ice and the mixture was extracted with diethyl ether (3×10 ml). The organic phase was washed with water and saturated sodium chloride solution, dried and concentrated by evaporation.

Yield: 2.8 g (100%) $^{13}$C-NMR (CDCl$_3$): 27.72 (t); 27.88 (t); 34.27 (t); 39.28 (d); 41.10 (q); 64.11 (t); 68.89 (d); 108.88 (s); 123.55 (d); 125.88 (d); 127.53 (d); 139.50 (s).

[1-(1,4-dioxa-spiro[4.5]dec-8-yl)-3-phenylpropyl]-dimethylamine 13e (R$^2$=phenethyl)

A solution of the aminonitrile 12 (21.93 g, 97 mmole) in absolute THF (180 ml) was added dropwise to a 1M solution of phenylethyl magnesium chloride in THF (242 ml, 242 mmole) under argon and while cooling with ice, and stirred for 20 hours at RT. To work up the reaction mixture saturated ammonium chloride solution (100 ml) and water (100 ml) were added while cooling with ice and the mixture was extracted with diethyl ether (3×100 ml). The organic phase was washed with water and saturated sodium chloride solution, dried, and concentrated by evaporation.

Yield: 34 g (>100%). $^{13}$C-NMR (CDCl$_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

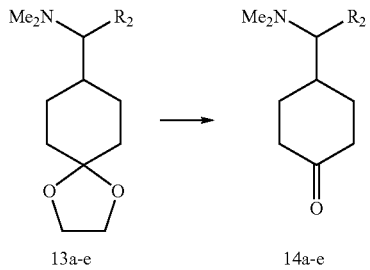

13a-e → 14a-e

4-[dimethylamino-(4-fluorophenyl)-methyl]-cyclohexanone 14a (R$^2$=4-fluorophenyl)

The crude product of the ketal 13a (26 g, 88 mmole) was dissolved in water (40 ml), concentrated hydrochloric acid (59 ml) was added, and the mixture was stirred for 20 hours at RT. The reaction mixture was extracted with diethyl ether (2×100 ml), the aqueous phase was made alkaline with 5 N NaOH while cooling in ice, extracted with dichloromethane (3×100 ml), dried, and concentrated by evaporation.

Yield: 21.36 g (98%) $^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[dimethylamino-(3-fluorophenyl)-methyl]-cyclohexanone 14b (R$^2$=3-fluorophenyl)

The ketal 13b (30.3 g, 103 mmole) was dissolved in water (44 ml), concentrated hydrochloric acid (64 ml) was added, and the mixture was stirred for 20 hours at RT. The reaction mixture was shaken with diethyl ether (2×100 ml), the aqueous phase was made alkaline with 5 N NaOH while cooling with ice, extracted with dichloromethane (3×100 ml), dried, and concentrated by evaporation. The ketone was isolated as a colorless solid.

Yield: 22.4 g (87%) m.p.: 72°-75° C. $^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62; 124.71; 129.03; 129.11; 139.00; 139.06; 161.16; 163.60; 211.40 (s).

4-[(4-chlorophenyl)-dimethylaminomethyl]-cyclohexanone 14c (R$^2$=4-chlorophenyl)

The ketal 13c (30.98 g, 100 mmole) was dissolved in water (44 ml), concentrated hydrochloric acid (64 ml) was added, and the mixture was stirred for 20 hours at RT. The reaction mixture was shaken with diethyl ether (2×100 ml), the aqueous phase was made alkaline with 5N NaOH while cooling with ice, extracted with dichloromethane (3×100 ml), dried and concentrated by evaporation. The ketone was isolated as an oil.

Yield: 21.9 g (82%) $^{13}$C-NMR (CDCl$_3$): 28.88 (t); 30.45 (t); 36.89 (t); 40.49 (t); 40.74 (t); 41.83 (q); 73.12 (d); 127.87 (d); 130.16 (d); 132.75 (d); 13470 (s); 211.35 (s).

4-(dimethylaminothiophen-2-yl-methyl)-cyclohexanone 14d (R$^2$=2-thienyl)

The ketal 13d (2.80 g, 10 mmole) was dissolved in water (4.4 ml), concentrated hydrochloric acid (6.4 ml) was added, and the mixture was stirred for 20 hours at RT. The reaction mixture was shaken with diethyl ether (2×10 ml), the aqueous phase was made alkaline with 5N NaOH while cooling with ice, extracted with dichloromethane (3×10 ml), dried and concentrated by evaporation. The ketone 14d was isolated as an oil.

Yield: 1.79 g (75%) $^{13}$C-NMR (CDCl$_3$): 30.02 (t); 30.18 (t); 38.84 (t); 40.29 (t); 39.28 (d); 41.17 (q); 68.24 (d); 123.88 (d); 126.01 (d); 126.34 (d); 138.77 (d); 211.49 (s).

4-(1-dimethylamino-3-phenylpropyl)-cyclohexanone 14e (R$^2$=phenethyl)

The crude product of the ketal 13e (29.6 g, 97 mmole) was dissolved in water (44 ml), concentrated hydrochloric acid (64 ml) was added, and the mixture was stirred for 20 hours at RT. The reaction mixture was shaken with diethyl ether (2×100 ml), the aqueous phase was made alkaline with 5N NaOH while cooling with ice, and extracted with dichloromethane (3×100 ml), dried and concentrated by evaporation. The ketone was isolated as a colorless oil.

Yield: 16.9 g (58%) $^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

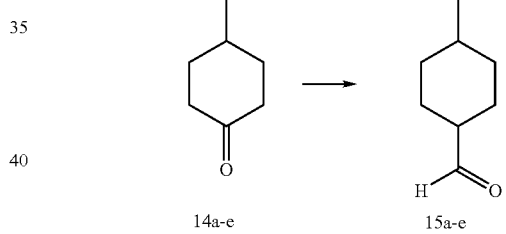

14a-e → 15a-e

4-[dimethylamino-(4-fluorophenyl)-methyl]-cyclohexanecarbaldehyde 15a (R$^2$=4-fluorophenyl)

(Methoxymethyl)triphenylphosphonium chloride (25.7 g, 75 mmole) was suspended in absolute THF (100 ml) under argon, potassium tert-butylate (8.42 g, 75 mmole), dissolved in absolute THF (70 ml), was added dropwise at 0° C., and the mixture was then stirred for 15 minutes at 0° C. The ketone 14a (12.44 g, 50 mmole), dissolved in absolute THF (75 ml), was then added dropwise at RT to the above solution and the mixture was stirred overnight at RT. The mixture was hydrolysed by dropwise addition of water (38 ml) and 6N HCl (112 ml) while cooling in iced water. After stirring for 1 hour at RT the mixture was extracted with ether (10×50 ml), and the aqueous phase was adjusted to pH 11 with 5N NaOH, shaken with ethyl acetate (3×50 ml), dried over Na$_2$SO$_4$ and concentrated by evaporation in vacuo. The crude product was purified by flash chromatography with ethyl acetate/cyclohexane (1:1).

Yield: 9.13 g (70%). $^1$H-NMR (DMSO, 600 MHz, selected signals): δ=1.97 (s, 3H); 1.99 (s, 3H); 3.08 (d, 1H, J=9.06 Hz); 3.14 (d, 1H, J=9.82 Hz); 9.53 (s, 1H); 9.56 (s, 1H). $^{13}$C-NMR (CDCl₃, both diastereomers): δ=23.97; 24.21; 25.85; 26.02; 26.17; 27.35; 28.00; 29.90; 37.26; 38.34; 41.50; 41.95; 47.36; 50.55; 72.75; 75.84; 114.25; 114.45; 130.33; 130.40; 132.61; 160.41; 162.83; 204.10; 204.93.

4-[dimethylamino-(3-fluorophenyl)-methyl]-cyclohexanecarbaldehyde 15b (R²=3-fluorophenyl)

(Methoxymethyl)triphenylphosphonium chloride (15.42 g, 45 mmole) was suspended in absolute THF (50 ml) under argon, potassium tert-butylate (5.05 g, 45 mmole), dissolved in absolute THF (50 ml), was added dropwise at 0° C., and the mixture was then stirred for 15 minutes at 0° C. The ketone 14b (7.48 g, 0.30 mmole), dissolved in absolute THF (50 ml), was then added dropwise at RT to the above solution and the mixture was stirred overnight at RT. The mixture was hydrolysed by dropwise addition of water (25 ml) and 6N HCl (75 ml) while cooling in iced water. After stirring for 1 hour at RT the mixture was extracted with ether (10×50 ml), and the aqueous phase was adjusted to pH 11 with 5N NaOH, extracted with ethyl acetate (3×50 ml), dried over Na₂SO₄ and concentrated by evaporation in vacuo. The crude product was purified by flash chromatography with ethyl acetate/cyclohexane (1:1).

Yield: 6.55 g (83%). m.p.: 40-43° C. ¹H-NMR (DMSO, 600 MHz, selected signals): δ=1.99 (s, 3H); 2.01 (s, 3H); 3.10 (d, 1H, J=9.06 Hz); 3.18 (d, 1H, J=9.82 Hz); 9.54 (s, 1H); 9.56 (s, 1H). ¹³C-NMR (CDCl₃): 23.93; 24.12; 25.79; 25.95; 26.19; 27.19; 27.99; 29.77; 37.05; 38.16; 41.45; 41.91; 47.30; 50.49; 71.50; 74.78; 113.50; 115.37; 124.78; 128.24; 130.59; 131.24; 131.67; 139.14; 139.76; 160.06; 163.50; 204.01; 204.85.

4-[(4-chlorophenyl)-dimethylaminomethyl]-cyclohexanecarbaldehyde 15c (R²=4-chlorophenyl)

(Methoxymethyl)triphenylphosphonium chloride (68.55 g, 200 mmole) was suspended in absolute THF (200 ml) under argon, potassium tert-butylate (22.44 g, 200 mmole), dissolved in absolute THF (300 ml), was added dropwise at 0° C., and the mixture was then stirred for 15 minutes at 0° C. The ketone 14c (38 g, 143 mmole), dissolved in absolute THF (200 ml), was then added dropwise at RT to the above solution and the mixture was stirred overnight at RT. The mixture was hydrolysed by dropwise addition of water (150 ml) and 6N HCl (450 ml) while cooling in iced water. After stirring for 1 hour at RT the mixture was extracted with ether (10×100 ml), and the aqueous phase was adjusted to pH 11 with 5N NaOH, shaken with ethyl acetate (3×100 ml), dried over Na₂SO₄ and concentrated by evaporation in vacuo. The crude product was purified by passage through two silica gel columns (400 g) with ethyl acetate/cyclohexane (1:1).

Yield: 32.17 g (80%). ¹H-NMR (DMSO, 600 MHz, selected signals): δ=1.97 (s, 3H); 1.99 (s, 3H); 3.07 (d, 1H, J=9.07 Hz); 3.14 (d, 1H, J=9.82 Hz); 9.53 (s, 1H); 9.55 (s, 1H). ¹³C-NMR (CDCl₃ both diastereomers): δ=23.92; 24.16; 25.80; 25.97; 26.13; 27.25; 27.90; 29.81; 37.08; 38.19; 41.47; 41.96; 47.29; 50.48; 72.81; 74.54; 127.65; 130.28; 132.40; 134.78; 135.43; 203.98; 204.82.

4-(dimethylaminothiophen-2-yl-methyl)-cyclohexanecarbaldehyde 15d (R²=2-thienyl)

(Methoxymethyl)triphenylphosphonium chloride (20.56 g, 60 mmole) was suspended in absolute THF (70 ml) under argon, potassium tert-butylate (6.73 g, 60 mmole), dissolved in absolute THF (70 ml), was added dropwise at 0° C., and the mixture was then stirred for 15 minutes at 0° C. The ketone 14d (9.4 g, 40 mmole), dissolved in absolute THF (70 ml), was then added dropwise at RT to the above solution and the mixture was stirred overnight at RT. The mixture was hydrolysed by dropwise addition of water, (60 ml) and 6 N HCl (180 ml) while cooling in iced water. After stirring for 1 hour at RT the mixture was extracted with ether (5×50 ml), and the aqueous phase was adjusted to pH 11 with 5 N NaOH, shaken with ethyl acetate (3×50 ml), dried over Na₂SO₄ and concentrated by evaporation in vacuo. The crude product was purified by flash chromatography with ethyl acetate/cyclohexane (1:1).

Yield: 7.66 g (77%). ¹H-NMR (DMSO, 600 MHz, selected signals): δ=2.03 (s, 3H); 2.05 (s, 3H); 3.44 (d, 1H, J=9.82 Hz); 3.52 (d, 1H, J=10.58 Hz); 9.54 (s, 1H); 9.58 (s, 1H). ¹³C-NMR (CDCl₃, both diastereomers): δ=23.74; 23.83; 25.80; 25.84; 26.98; 27.09; 29.15; 29.68; 39.13; 40.20; 40.98; 41.29 (N(CH₃)₂); 47.48; 50.49; 67.81; 69.79; 123.61; 123.70; 125.89; 126.20; 126.24; 139.14; 139.48; 204.07; 204.82.

4-(1-dimethylamino-3-phenylpropyl)-cyclohexanecarbaldehyde 15e (R²=phenethyl)

(Methoxymethyl)triphenylphosphonium chloride (20.56 g, 60 mmole) was suspended in absolute THF (85 ml) under argon, potassium tert-butylate (6.73 g, 60 mmole), dissolved in absolute THF (70 ml), was added dropwise at 0° C., and the mixture was then stirred for 15 minutes at 0° C. The ketone 14e (10.2 g, 40 mmole), dissolved in absolute THF (60 ml), was then added dropwise at RT to the above solution and the mixture was stirred overnight at RT. The mixture was hydrolysed by dropwise addition of water (35 ml) and 6N HCl (90 ml) while cooling in iced water. After stirring for 1 hour at RT the mixture was extracted with ether (10×50 ml), and the aqueous phase was adjusted to pH 11 with 5N NaOH, extracted with ethyl acetate (3×50 ml), dried over Na₂SO₄ and concentrated by evaporation in vacuo. The crude product was purified by flash chromatography with ethyl acetate/cyclohexane (1:1).

Yield: 6.73 g (63%). ¹H-NMR (DMSO, 600 MHz, selected signals): δ=2.18 (s, 3H); 2.20 (s, 3H); 9.54 (s, 1H); 9.61 (s, 1H). ¹³C-NMR (CDCl₃, both diastereomers): δ=24.35; 24.49; 26.00; 26.09; 26.85; 27.79; 29.07; 29.13; 35.27; 39.02; 40.98; 41.19; 46.99; 50.33; 66.85; 67.85; 70.54; 71.42; 125.40; 125.44; 128.02; 128.13; 131.15; 131.17; 142.45; 204.10; 205.01.

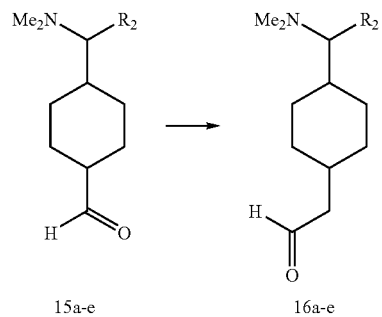

15a-e        16a-e

{4-[dimethylamino-(4-fluorophenyl)-methyl]-cyclohexyl}-acetaldehyde 16a (R²=4-fluorophenyl)

(Methoxymethyl)triphenylphosphonium chloride (43.53 g, 127 mmole) was suspended in absolute THF (200 ml) under argon, potassium tert-butylate (14.25 g, 127 mmole), dissolved in absolute THF (130 ml), was added dropwise at 0° C., and the mixture was then stirred for 15 minutes at 0° C. The aldehyde 15a (22.3 g, 85 mmole), dissolved in absolute THF (130 ml), was then added dropwise at RT and the mixture was stirred overnight at RT. The mixture was hydrolysed by dropwise addition of water (80 ml) and 6N HCl (200 ml) while cooling in iced water. After stirring for 1 hour at RT the mixture was extracted 10 times with ether (each time 100 ml). The aqueous phase was adjusted to pH 11 with 5N NaOH, shaken three times with ethyl acetate (each time 100 ml), dried over $Na_2SO_4$ and concentrated by evaporation in vacuo. The crude product was purified by flash chromatography with ethyl acetate/cyclohexane (1:1).

Yield: 15.8 g (67%) $^{13}$C-NMR (CDCl$_3$, both diastereomers): δ=25.08; 25.87; 28.80; 29.10; 29.13; 29.62; 30.82; 32.90; 33.08; 36.19; 38.43; 41.36; 42.01; 47.94; 51.17; 71.11; 74.69; 114.11; 114.20; 114.32; 130.32; 130.40; 132.00; 132.92; 160.31; 162.74; 202.15; 202.23.

{4-[dimethylamino-(3-fluorophenyl)-methyl]-cyclohexyl}-acetaldehyde 16b ($R^2$=3-fluorophenyl)

(Methoxymethyl)triphenylphosphonium chloride (26.73 g, 78 mmole) was suspended in absolute THF (90 ml) under argon, potassium tert-butylate (8.75 g, 78 mmole), dissolved in absolute THF (90 ml), was added dropwise at 0° C., and the mixture was then stirred for 15 minutes at 0° C. The aldehyde 15b (13.69 g, 52 mmole), dissolved in absolute THF (90 ml), was then added dropwise at RT and the mixture was stirred overnight at RT. The mixture was hydrolysed by dropwise addition of water (50 ml) and 6N HCl (150 ml), while cooling in iced water. After stirring for 1 hour at RT the mixture was extracted 10 times with ether (each time 50 ml). The aqueous phase was adjusted to pH 11 with 5N NaOH, shaken three times with ethyl acetate (each time 100 ml), dried over $Na_2SO_4$ and concentrated by evaporation in vacuo. The crude product was purified by flash chromatography with ethyl acetate/cyclohexane (1:1).

Yield: 12.61 g (87%) $^{13}$C-NMR (CDCl$_3$, both diastereomers): δ=25.19; 25.83; 28.90; 29.06; 29.14; 29.68; 30.77; 32.92; 32.98; 33.10; 36.05; 38.36; 41.39; 42.04; 48.02; 51.20; 71.48; 75.07; 113.43; 113.49; 113.64; 113.69; 115.55; 115.76; 124.89; 128.70; 128.78; 128.88; 139.24; 140.08; 140.14; 161.09; 163.52; 202.19; 202.27.

{4-[(4-chlorophenyl)-dimethylaminomethyl]-cyclohexyl}-acetaldehyde 16c ($R^2$=4-chlorophenyl)

(Methoxymethyl)triphenylphosphonium chloride (25.02 g, 73 mmole) was suspended in absolute THF (90 ml) under argon, potassium tert-butylate (8.19 g, 73 mmole), dissolved in absolute THF (90 ml), was added dropwise at 0° C., and the mixture was then stirred for 15 minutes at 0° C. The aldehyde 15c (13.86 g, 49 mmole), dissolved in absolute THF (90 ml), was then added dropwise at RT and the mixture was stirred overnight at RT. The mixture was hydrolysed by dropwise addition of water (50 ml) and 6N HCl (150 ml) while cooling in iced water. After stirring for 1 hour at RT the mixture was extracted ten times with ether (each time 50 ml). The aqueous phase was adjusted to pH 11 with 5N NaOH, shaken three times with ethyl acetate (each time 100 ml), dried over $Na_2SO_4$ and concentrated by evaporation in vacuo. The crude product was purified by flash chromatography with ethyl acetate/cyclohexane (1:1).

Yield: 12.07 g (84%). $^{13}$C-NMR (CDCl$_3$, both diastereomers): δ=25.06; 25.82; 28.74; 29.00; 29.13; 29.60; 30.77; 32.87; 32.94; 33.07; 36.06; 38.32; 41.38; 42.05; 47.95; 51.17; 71.23; 74.80; 127.58; 127.66; 130.31; 132.28; 132.34; 134.81; 135.77; 202.12; 202.20.

{4-[dimethylaminothiophen-2-yl-methyl]-cyclohexyl}-acetaldehyde 16d ($R^2$=2-thienyl)

(Methoxymethyl)triphenylphosphonium chloride (28.79 g, 84 mmole) was suspended in absolute THF (100 ml) under argon, potassium tert-butylate (9.42 g, 84 mmole), dissolved in absolute THF (100 ml), was added dropwise at 0° C., and the mixture was then stirred for 15 min at 0° C. The aldehyde 15d (14.08 g, 56 mmole), dissolved in absolute THF (100 ml), was then added dropwise at RT and the mixture was stirred overnight at RT. The mixture was hydrolysed by dropwise addition of water (50 ml) and 6N HCl (150 ml) while cooling in iced water. After stirring for 1 hour at RT the mixture was extracted ten times with ether (each time 50 ml). The aqueous phase was adjusted to pH 11 with 5N NaOH, shaken with three times with ethyl acetate (each time 100 ml), dried over $Na_2SO_4$ and concentrated by evaporation in vacuo. The crude product was purified by flash chromatography with ethyl acetate/cyclohexane (1:2).

Yield: 11.48 g (77%). $^{13}$C-NMR (CDCl$_3$, both diastereomers): δ=25.80; 25.88; 28.73; 29.95; 30.49, 32.23; 32.76; 37.89; 40.21; 40.88; 41.23; 48.36; 51.09; 66.02; 69.97; 123.19; 123.72; 125.95; 126.31; 139.42; 139.91; 202.61.

[4-(1-dimethylamino-3-phenylpropyl)-cyclohexyl]-acetaldehyde 16e ($R^2$-phenethyl)

(Methoxymethyl)triphenylphosphonium chloride (50.3 g, 147 mmole) was suspended in absolute THF (150 ml) under argon, potassium tert-butylate (16.5 g, 147 mmole), dissolved in absolute THF (140 ml), was added dropwise at 0° C. and the mixture was then stirred for 15 minutes at 0° C. The aldehyde 15e (27.0 g, 98 mmole), dissolved in absolute THF (150 ml), was then added dropwise at RT and the mixture was stirred overnight at RT. The mixture was hydrolysed by dropwise addition of water (102 ml) and 6N HCl (240 ml) while cooling in iced water. After stirring for 1 hour at RT the mixture was extracted five times with ether (each time 200 ml). The aqueous phase was adjusted to pH 11 with 5N NaOH while cooling with ice, shaken three times with ethyl acetate (each time 200 ml), dried over $Na_2SO_4$ and concentrated by evaporation in vacuo. The crude product was purified by flash chromatography with ethyl acetate/cyclohexane (1:1).

Yield: 18.1 g (64%) $^{13}$C-NMR (CDCl$_3$, both diastereomers): δ=25.55; 26.19; 29.04; 29.15; 29.35; 29.85; 31.00; 32.87; 32.68; 33.04; 35.33; 38.49; 40.86; 41.13; 47.51; 51.15; 65.48; 68.09; 125.58; 128.20; 142.79; 202.69.

Automated Synthesis

The compounds were prepared with the aid of the automated synthesis protocol using the SLT106 accelerator from the company Chemspeed Ltd according to the following experimental procedure:

120 μmole (1.2 ml, 0.1 M in methanol) of aldehyde solution (solution II), 130 μmole (1.3 ml, 0.1 M in methanol) of amine solution (solution III) and 100 μmole (1 ml, 0.1 M in methanol) of isonitrile amide derivative (solution I) were added at room temperature to a dry 13 ml capacity double jacket glass reactor. The reaction solution was heated for 6 hours at 60° C. and shaken. After completion of the reaction, the reaction solution was concentrated by evaporation in a GeneVac. Purification was carried out by HPLC.

The following compounds were prepared by the general procedure described above. The analysis was carried out by HPLC-MS. In all cases the exact mass was found as M+1.

| No. | Name | Mass |
|---|---|---|
| 17. | [{4-[(4-benzyl-5-pyrrolidin-1-yl-oxazol-2-yl)-piperidin-1-yl-methyl]-cyclohexyl}-(4-fluorophenyl)-methyl]-dimethylamine | 558.37 |
| 18. | ((4-benzyl-5-morpholin-4-yl-oxazol-2-yl)-{4-[dimethylamino-(4-fluorophenyl)-methyl]-cyclohexyl}-methyl)-methylphenylamine | 596.35 |
| 19. | ([4-benzyl-5-(4-methylpiperidin-1-yl)-oxazol-2-yl]-{4-[dimethylamino-(4-fluorophenyl)-methyl]-cyclohexyl}-methyl)-methylphenylamine | 608.39 |
| 20. | ([4-benzyl-5-(4-methylpiperidin-1-yl)-oxazol-2-yl]-{4-[(4-chlorophenyl)-dimethylaminomethyl]-cyclohexyl}-methyl)-diethylamine | 590.38 |
| 21. | Benzyl-[4-benzyl-2-({4-[(4-chlorophenyl)-dimethylaminomethyl]-cyclohexyl}-diethylamino)-oxazol-5-yl]-methylamine | 612.36 |
| 22. | Benzyl-{4-benzyl-2-[{4-[(4-chlorophenyl)-dimethylaminomethyl]-cyclohexyl}-(methylphenylamine)-methyl]-oxazol-5-yl}-methylamine | 646.34 |
| 23. | [(4-{[4-benzyl-5-(4-benzyl-piperidin-1-yl)-oxazol-2-yl]-piperidin-1-yl-methyl}-cyclohexyl)-thiophen-2-yl-methyl]-dimethylamine | 650.40 |
| 24. | [(4-{[4-benzyl-5-(4-methylpiperidin-1-yl)-oxazol-2-yl]-piperidin-1-yl-methyl}-cyclohexyl)-thiophen-2-yl-methyl]-dimethylamine | 574.37 |
| 25. | Benzyl-(4-benzyl-2-{[4-(dimethylamino-thiophen-2-yl-methyl)-cyclohexyl]-piperidin-1-yl-methyl}-oxazol-5-yl)-methylamine | 596.35 |
| 26. | [(4-{[4-benzyl-5-(4-phenylpiperazin-1-yl)-oxazol-2-yl]-piperidin-1-yl-methyl}-cyclohexyl)-thiophen-2-yl-methyl]-dimethylamine | 637.38 |
| 27. | {[4-benzyl-5-(4-benzyl-piperidin-1-yl)-oxazol-2-yl]-[4-(dimethylamino-thiophen-2-yl-methyl)-cyclohexyl]-methyl}-diethylamine | 638.40 |
| 28. | {[4-benzyl-5-(4-benzyl-piperazin-1-yl)-oxazol-2-yl]-[4-(dimethylamino-thiophen-2-yl-methyl)-cyclohexyl]-methyl}-diethylamine | 639.40 |
| 29. | {[4-benzyl-5-(4-methylpiperidin-1-yl)-oxazol-2-yl]-[4-(dimethylamino-thiophen-2-yl-methyl)-cyclohexyl]-methyl}-diethylamine | 562.37 |
| 30. | Benzyl-(4-benzyl-2-{diethylamino-[4-(dimethylaminothiophen-2-yl-methyl)-cyclohexyl]-methyl}-oxazol-5-yl)-methylamine | 584.35 |
| 31. | {[4-benzyl-5-(4-phenylpiperazin-1-yl)-oxazol-2-yl]-[4-(dimethylamino-thiophen-2-yl-methyl)-cyclohexyl]-methyl}-diethylamine | 625.38 |
| 32. | ({4-[[4-benzyl-5-(4-benzylpiperidin-1-yl)-oxazol-2-yl]-(4-benzylpiperazin-1-yl)-methyl]-cyclohexyl}-thiophen-2-yl-methyl)-dimethylamine | 741.44 |
| 33. | [(4-{[4-benzyl-5-(3-methylpiperidin-1-yl)-oxazol-2-yl]-piperidin-1-yl-methyl}-cyclohexyl)-(4-fluorophenyl)-methyl]-dimethylamine | 586.40 |
| 34. | [4-benzyl-2-(diethylamino-{4-[dimethylamino-(4-fluorophenyl)-methyl]-cyclohexyl}-methyl)-oxazol-5-yl]-methylphenethylamine | 610.40 |
| 35. | [4-benzyl-2-(diethylamino-{4-[dimethylamino-(4-fluorophenyl)-methyl]-cyclohexyl}-methyl)-oxazol-5-yl]-diethylamine | 548.39 |
| 36. | ([4-benzyl-5-(3-methylpiperidin-1-yl)-oxazol-2-yl]-{4-[dimethylamino-(4-fluorophenyl)-methyl]-cyclohexyl}-methyl)-diethylamine | 574.40 |
| 37. | ([4-benzyl-5-(3,5-dimethylpiperidin-1-yl)-oxazol-2-yl]-{4-[dimethylamino-(4-fluorophenyl)-methyl]-cyclohexyl}-methyl)-methylphenylamine | 622.40 |
| 38. | {4-benzyl-2-[{4-[dimethylamino-(4-fluorophenyl)-methyl]-cyclohexyl}-(methylphenylamine)-methyl]-oxazol-5-yl}-methylphenethylamine | 644.39 |
| 39. | [4-benzyl-2-({4-[(4-chlorophenyl)-dimethylaminomethyl]-cyclohexyl}-piperidin-1-yl-methyl)-oxazol-5-yl]-diethylamine | 576.36 |
| 40. | [(4-{[4-benzyl-5-(3-methylpiperidin-1-yl)-oxazol-2-yl]-piperidin-1-yl-methyl}-cyclohexyl)-(4-chlorophenyl)-methyl]-dimethylamine | 602.38 |
| 41. | ([4-benzyl-5-(3,5-dimethylpiperidin-1-yl)-oxazol-2-yl]-{4-[(4-chlorophenyl)-dimethylaminomethyl]-cyclohexyl}-methyl)-diethylamine | 604.39 |
| 42. | ([4-benzyl-5-(3,5-dimethylpiperidin-1-yl)-oxazol-2-yl]-{4-[(4-chlorophenyl)-dimethylaminomethyl]-cyclohexyl}-methyl)-methylphenylamine | 638.38 |
| 43. | {4-benzyl-2-[{4-[(4-chlorophenyl)-dimethylaminomethyl]-cyclohexyl}-(methylphenylamine)-methyl]-oxazol-5-yl}-methylphenethylamine | 660.36 |
| 44. | [4-benzyl-2-((4-benzylpiperazin-1-yl)-{4-[(4-chlorophenyl)-dimethylaminomethyl]-cyclohexyl}-methyl)-oxazol-5-yl]-diethylamine | 667.40 |
| 45. | [(4-{[4-benzyl-5-(3,5-dimethylpiperidin-1-yl)-oxazol-2-yl]-piperidin-1-yl-methyl}-cyclohexyl)-thiophen-2-yl-methyl]-dimethylamine | 588.39 |
| 46. | (4-benzyl-2-{[4-(dimethylaminothiophen-2-yl-methyl)-cyclohexyl]-piperidin-1-yl-methyl}-oxazol-5-yl)-methylphenethylamine | 610.37 |
| 47. | (4-benzyl-2-{[4-(dimethylamino-thiophen-2-yl-methyl)-cyclohexyl]-piperidin-1-yl-methyl}-oxazol-5-yl)-diethylamine | 548.35 |
| 48. | ({4-[(4-benzyl-5-thiomorpholin-4-yl-oxazol-2-yl)-piperidin-1-yl-methyl]-cyclohexyl}-thiophen-2-yl-methyl)-dimethylamine | 578.31 |
| 49. | (4-benzyl-2-{diethylamino-[4-(dimethylamino-thiophen-2-yl-methyl)-cyclohexyl]-methyl}-oxazol-5-yl)-methylphenethylamine | 598.37 |
| 50. | (4-benzyl-2-{diethylamino-[4-(dimethylaminothiophen-2-yl-methyl)-cyclohexyl]-methyl}-oxazol-5-yl)-diethylamine | 536.35 |
| 51. | {[4-benzyl-5-(3-methylpiperidin-1-yl)-oxazol-2-yl]-[4-(dimethylamino-thiophen-2-yl-methyl)-cyclohexyl]-methyl}-diethylamine | 562.37 |
| 52. | {(4-benzyl-5-thiomorpholin-4-yl-oxazol-2-yl)-[4-(dimethylaminothiophen-2-yl-methyl)-cyclohexyl]-methyl}-methylphenylamine | 600.30 |
| 53. | ({4-[[4-benzyl-5-(3,5-dimethylpiperidin-1-yl)-oxazol-2-yl]-(4-benzyl-piperazin-1-yl)-methyl]-cyclohexyl}-thiophen-2-yl-methyl)-dimethylamine | 679.43 |
| 54. | (4-benzyl-2-{(4-benzyl-piperazin-1-yl)-[4-(dimethylaminothiophen-2-yl-methyl)-cyclohexyl]-methyl}-oxazol-5-yl)-methyl-phenethylamine | 701.41 |

-continued

| No. | Name | Mass |
|---|---|---|
| 55. | ({4-[(4-benzylpiperazin-1-yl)-(4-benzyl-5-thiomorpholin-4-yl-oxazol-2-yl)-methyl]-cyclohexyl}-thiophen-2-yl-methyl)-dimethylamine | 669.35 |
| 56. | [(4-{2-[4-benzyl-5-(4-benzyl-piperazin-1-yl)-oxazol-2-yl]-2-piperidin-1-yl-ethyl}-cyclohexyl)-(4-chlorophenyl)-methyl]-dimethylamine | 693.42 |
| 57. | [(4-{2-[4-benzyl-5-(4-methylpiperidin-1-yl)-oxazol-2-yl]-2-piperidin-1-yl-ethyl}-cyclohexyl)-(4-chlorophenyl)-methyl]-dimethylamine | 616.39 |
| 58. | Benzyl-[4-benzyl-2-(2-{4-[(4-chlorophenyl)-dimethylaminomethyl]-cyclohexyl}-1-piperidin-1-yl-ethyl)-oxazol-5-yl]-methylamine | 638.38 |
| 59. | (1-[4-benzyl-5-(4-benzylpiperidin-1-yl)-oxazol-2-yl]-2-{4-[(4-chlorophenyl)-dimethylaminomethyl]-cyclohexyl}-ethyl)-diethylamine | 680.42 |
| 60. | (1-[4-benzyl-5-(4-methylpiperidin-1-yl)-oxazol-2-yl]-2-{4-[(4-chlorophenyl)-dimethylaminomethyl]-cyclohexyl}-ethyl)-diethylamine | 604.39 |
| 61. | Benzyl-[4-benzyl-2-(2-{4-[(4-chlorophenyl)-dimethylaminomethyl]-cyclohexyl}-1-diethylamino-ethyl)-oxazol-5-yl]-methylamine | 626.38 |
| 62. | [{4-[2-[4-benzyl-5-(4-benzyl-piperidin-1-yl)-oxazol-2-yl]-2-(4-benzyl-piperazin-1-yl)-ethyl]-cyclohexyl}-(4-chlorophenyl)-methyl]-dimethylamine | 783.46 |
| 63. | [{4-[2-[4-benzyl-5-(4-benzylpiperazin-1-yl)-oxazol-2-yl]-2-(4-benzyl-piperazin-1-yl)-ethyl]-cyclohexyl}-(4-chlorophenyl)-methyl]-dimethylamine | 784.46 |
| 64. | [{4-[2-[4-benzyl-5-(4-methylpiperidin-1-yl)-oxazol-2-yl]-2-(4-benzyl-piperazin-1-yl)-ethyl]-cyclohexyl}-(4-chlorophenyl)-methyl]-dimethylamine | 707.43 |
| 65. | [(4-{2-[4-benzyl-5-(4-methylpiperidin-1-yl)-oxazol-2-yl]-2-piperidin-1-yl-ethyl}-cyclohexyl)-(4-fluorophenyl)-methyl]-dimethylamine | 600.42 |
| 66. | Benzyl-[4-benzyl-2-(2-{4-[dimethylamino-(4-fluorophenyl)-methyl]-cyclohexyl}-1-piperidin-1-yl-ethyl)-oxazol-5-yl]-methylamine | 622.40 |
| 67. | (1-[4-benzyl-5-(4-benzyl-piperidin-1-yl)-oxazol-2-yl]-2-{4-[dimethylamino-(4-fluorophenyl)-methyl]-cyclohexyl}-ethyl)-diethylamine | 664.45 |
| 68. | (1-[4-benzyl-5-(4-benzyl-piperazin-1-yl)-oxazol-2-yl]-2-{4-[dimethylamino-(4-fluorophenyl)-methyl]-cyclohexyl}-ethyl)-diethylamine | 665.45 |
| 69. | (1-[4-benzyl-5-(4-methylpiperidin-1-yl)-oxazol-2-yl]-2-{4-[dimethylamino-(4-fluorophenyl)-methyl]-cyclohexyl}-ethyl)-diethylamine | 588.42 |
| 70. | Benzyl-[4-benzyl-2-(1-diethylamino-2-{4-[dimethylamino-(4-fluorophenyl)-methyl]-cyclohexyl}-ethyl)-oxazol-5-yl]-methylamine | 610.40 |
| 71. | [{4-[2-[4-benzyl-5-(4-methylpiperidin-1-yl)-oxazol-2-yl]-2-(4-benzyl-piperazin-1-yl)-ethyl]-cyclohexyl}-(4-fluorophenyl)-methyl]-dimethylamine | 691.46 |
| 72. | [(4-{2-[4-benzyl-5-(4-benzyl-piperidin-1-yl)-oxazol-2-yl]-2-piperidin-1-yl-ethyl}-cyclohexyl)-thiophen-2-yl-methyl]-dimethylamine | 664.42 |
| 73. | [(4-{2-[4-benzyl-5-(4-benzyl-piperazin-1-yl)-oxazol-2-yl]-2-piperidin-1-yl-ethyl}-cyclohexyl)-thiophen-2-yl-methyl]-dimethylamine | 665.41 |
| 74. | [(4-{2-[4-benzyl-5-(4-methylpiperidin-1-yl)-oxazol-2-yl]-2-piperidin-1-yl-ethyl}-cyclohexyl)-thiophen-2-yl-methyl]-dimethylamine | 588.39 |
| 75. | Benzyl-(4-benzyl-2-{2-[4-(dimethylaminothiophen-2-yl-methyl)-cyclohexyl]-1-piperidin-1-yl-ethyl}-oxazol-5-yl)-methylamine | 610.37 |
| 76. | [(4-{2-[4-benzyl-5-(4-phenyl-piperazin-1-yl)-oxazol-2-yl]-2-piperidin-1-yl-ethyl}-cyclohexyl)-thiophen-2-yl-methyl]-dimethylamine | 651.40 |
| 77. | {1-[4-benzyl-5-(4-benzyl-piperidin-1-yl)-oxazol-2-yl]-2-[4-(dimethylamino-thiophen-2-yl-methyl)-cyclohexyl]-ethyl}-diethylamine | 652.42 |
| 78. | {1-[4-benzyl-5-(4-benzyl-piperazin-1-yl)-oxazol-2-yl]-2-[4-(dimethylamino-thiophen-2-yl-methyl)-cyclohexyl]-ethyl}-diethylamine | 653.41 |
| 79. | {1-[4-benzyl-5-(4-methylpiperidin-1-yl)-oxazol-2-yl]-2-[4-(dimethylamino-thiophen-2-yl-methyl)-cyclohexyl]-ethyl}-diethylamine | 576.39 |
| 80. | Benzyl-(4-benzyl-2-{1-diethylamino-2-[4-(dimethylaminothiophen-2-yl-methyl)-cyclohexyl]-ethyl}-oxazol-5-yl)-methylamine | 598.37 |
| 81. | ({4-[2-[4-benzyl-5-(4-benzyl-piperidin-1-yl)-oxazol-2-yl]-2-(4-benzyl-piperazin-1-yl)-ethyl]-cyclohexyl}-thiophen-2-yl-methyl)-dimethylamine | 755.46 |
| 82. | ({4-[2-[4-benzyl-5-(4-benzylpiperazin-1-yl)-oxazol-2-yl]-2-(4-benzyl-piperazin-1-yl)-ethyl]-cyclohexyl}-thiophen-2-yl-methyl)-dimethylamine | 756.45 |
| 83. | ({4-[2-[4-benzyl-5-(4-methylpiperidin-1-yl)-oxazol-2-yl]-2-(4-benzyl-piperazin-1-yl)-ethyl]-cyclohexyl}-thiophen-2-yl-methyl)-dimethylamine | 679.43 |
| 84. | Benzyl-(4-benzyl-2-{1-(4-benzyl-piperazin-1-yl)-2-[4-(dimethylamino-thiophen-2-yl-methyl)-cyclohexyl]-ethyl}-oxazol-5-yl)-methylamine | 701.41 |
| 85. | ({4-[2-[4-benzyl-5-(4-phenyl-piperazin-1-yl)-oxazol-2-yl]-2-(4-benzyl-piperazin-1-yl)-ethyl]-cyclohexyl}-thiophen-2-yl-methyl)-dimethylamine | 742.44 |
| 86. | [4-benzyl-2-(2-{4-[(4-chlorophenyl)-dimethylaminomethyl-cyclohexyl}-1-piperidin-1-yl-ethyl)-oxazol-5-yl]-methylphenethylamine | 652.39 |
| 87. | [4-benzyl-2-(2-{4-[(4-chlorophenyl)-dimethylaminomethyl]-cyclohexyl}-1-piperidin-1-yl-ethyl)-oxazol-5-yl]-diethylamine | 590.38 |
| 88. | (1-[4-benzyl-5-(3,5-dimethylpiperidin-1-yl)-oxazol-2-yl]-2-{4-[(4-chlorophenyl)-dimethylaminomethyl]-cyclohexyl}-ethyl)-diethylamine | 618.41 |
| 89. | [4-benzyl-2-(2-{4-[(4-chlorophenyl)-dimethylaminomethyl]-cyclohexyl}-1-diethylaminoethyl)-oxazol-5-yl]-methyl-phenethylamine | 640.39 |
| 90. | [4-benzyl-2-(2-{4-[(4-chlorophenyl)-dimethylaminomethyl]-cyclohexyl}-1-diethylaminoethyl)-oxazol-5-yl]-diethylamine | 578.38 |
| 91. | (1-(4-benzyl-5-thiomorpholin-4-yl-oxazol-2-yl)-2-{4-[(4-chlorophenyl)-dimethylaminomethyl]-cyclohexyl}-ethyl)-diethylamine | 608.33 |
| 92. | (1-(4-benzyl-5-thiomorpholin-4-yl-oxazol-2-yl)-2-{4-[(4-chlorophenyl)-dimethylaminomethyl]-cyclohexyl}-ethyl)-methylphenylamine | 642.32 |

-continued

| No. | Name | Mass |
|---|---|---|
| 93. | [4-Benzyl-2-(1-(4-benzylpiperazin-1-yl)-2-{4-[(4-chlorophenyl)-dimethylaminomethyl]-cyclohexyl}-ethyl)-oxazol-5-yl]-methylphenethyl-amine | 743.43 |
| 94. | [4-benzyl-2-(1-(4-benzylpiperazin-1-yl)-2-{4-[(4-chlorophenyl)-dimethylaminomethyl]-cyclohexyl}-ethyl)-oxazol-5-yl]-diethylamine | 681.42 |
| 95. | [4-benzyl-2-(2-{4-[dimethylamino-(4-fluorophenyl)-methyl]-cyclohexyl}-1-piperidin-1-yl-ethyl)-oxazol-5-yl]-methylphenethylamine | 636.42 |
| 96. | (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-diethylamine | 602.44 |
| 97. | [4-benzyl-2-(1-diethylamino-2-{4-[dimethylamino-(4-fluorophenyl)-methyl]-cyclohexyl}-ethyl)-oxazol-5-yl]-methylphenethylamine | 624.42 |
| 98. | [4-benzyl-2-(1-diethylamino-2-{4-[dimethylamino-(4-fluorophenyl)-methyl]-cyclohexyl}-ethyl)-oxazol-5-yl]-diethylamine | 562.40 |
| 99. | (1-(4-benzyl-5-thiomorpholin-4-yl-oxazol-2-yl)-2-{4-[dimethylamino-(4-fluorophenyl)-methyl]-cyclohexyl}-ethyl)-diethylamine | 592.36 |
| 100. | (1-[4-benzyl-5-(3-methylpiperidin-1-yl)-oxazol-2-yl]-2-{4-[dimethylamino-(4-fluorophenyl)-methyl]-cyclohexyl}-ethyl)-diethylamine | 588.42 |
| 101. | (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-methylphenylamine | 636.42 |
| 102. | {4-benzyl-2-[2-{4-[dimethylamino-(4-fluorophenyl)-methyl]-cyclohexyl}-1-(methylphenylamine)-ethyl]-oxazol-5-yl}-methylphenethylamine | 658.40 |
| 103. | {4-benzyl-2-[2-{4-[dimethylamino-(4-fluorophenyl)-methyl]-cyclohexyl}-1-(methylphenylamine)-ethyl]-oxazol-5-yl}-diethylamine | 596.39 |
| 104. | (1-(4-benzyl-5-thiomorpholin-4-yl-oxazol-2-yl)-2-{4-[dimethylamino-(4-fluorophenyl)-methyl]-cyclohexyl}-ethyl)-methylphenylamine | 626.35 |
| 105. | (1-[4-benzyl-5-(3-methylpiperidin-1-yl)-oxazol-2-yl]-2-{4-[dimethylamino-(4-fluorophenyl)-methyl]-cyclohexyl}-ethyl)-methylphenylamine | 622.40 |
| 106. | [{4-[2-[4-benzyl-5-(3-methylpiperidin-1-yl)-oxazol-2-yl]-2-(4-benzyl-piperazin-1-yl)-ethyl]-cyclohexyl}-(4-fluorophenyl)-methyl]-dimethylamine | 691.46 |
| 107. | [(4-{2-[4-benzyl-5-(3,5-dimethylpiperidin-1-yl)-oxazol-2-yl]-2-piperidin-1-yl-ethyl}-cyclohexyl)-thiophen-2-yl-methyl]-dimethylamine | 602.40 |
| 108. | (4-benzyl-2-{2-[4-(dimethylaminothiophen-2-yl-methyl)-cyclohexyl]-1-piperidin-1-yl-ethyl}-oxazol-5-yl)-methylphenethylamine | 624.39 |
| 109. | (4-benzyl-2-{2-[4-(dimethylaminothiophen-2-yl-methyl)-cyclohexyl]-1-piperidin-1-yl-ethyl}-oxazol-5-yl)-diethylamine | 562.37 |
| 110. | ({4-[2-(4-benzyl-5-thiomorpholin-4-yl-oxazol-2-yl)-2-piperidin-1-yl-ethyl]-cyclohexyl}-thiophen-2-yl-methyl)-dimethylamine | 592.33 |
| 111. | [(4-{2-[4-benzyl-5-(3-methylpiperidin-1-yl)-oxazol-2-yl]-2-piperidin-1-yl-ethyl}-cyclohexyl)-thiophen-2-yl-methyl]-dimethylamine | 588.39 |
| 112. | {1-[4-benzyl-5-(3,5-dimethylpiperidin-1-yl)-oxazol-2-yl]-2-[4-(dimethylamino-thiophen-2-yl-methyl)-cyclohexyl]-ethyl}-diethylamine | 590.40 |
| 113. | (4-benzyl-2-{1-diethylamino-2-[4-(dimethylaminothiophen-2-yl-methyl)-cyclohexyl]-ethyl}-oxazol-5-yl)-methylphenethylamine | 612.39 |
| 114. | (4-benzyl-2-{1-diethylamino-2-[4-(dimethylaminothiophen-2-yl-methyl)-cyclohexyl]-ethyl}-oxazol-5-yl)-diethylamine | 550.37 |
| 115. | {1-(4-benzyl-5-thiomorpholin-4-yl-oxazol-2-yl)-2-[4-(dimethylamino-thiophen-2-yl-methyl)-cyclohexyl]-ethyl}-diethylamine | 580.33 |
| 116. | {1-[4-benzyl-5-(3-methylpiperidin-1-yl)-oxazol-2-yl]-2-[4-(dimethylamino-thiophen-2-yl-methyl)-cyclohexyl]-ethyl}-diethylamine | 576.39 |
| 117. | {1-[4-benzyl-5-(3-methylpiperidin-1-yl)-oxazol-2-yl]-2-[4-(dimethylamino-thiophen-2-yl-methyl)-cyclohexyl]-ethyl}-methylphenylamine | 610.37 |
| 118. | ({4-[2-(4-benzylpiperazin-1-yl)-2-(4-benzyl-5-thiomorpholin-4-yl-oxazol-2-yl)-ethyl]-cyclohexyl}-thiophen-2-yl-methyl)-dimethylamine | 683.37 |
| 119. | ({4-[2-[4-benzyl-5-(3-methylpiperidin-1-yl)-oxazol-2-yl]-2-(4-benzyl-piperazin-1-yl)-ethyl]-cyclohexyl}-thiophen-2-yl-methyl)-dimethylamine | 679.43 |
| 120. | [{4-[(4-benzyl-5-pyrrolidin-1-yl-oxazol-2-yl)-morpholin-4-yl-methyl]-cyclohexyl}-(3-fluorophenyl)-methyl]-dimethylamine | 560.35 |
| 121. | [{4-[(4-benzyl-5-morpholin-4-yl-oxazol-2-yl)-morpholin-4-yl-methyl]-cyclohexyl}-(3-fluorophenyl)-methyl]-dimethylamine | 576.35 |
| 122. | [(4-{(4-benzyl-5-pyrrolidin-1-yl-oxazol-2-yl)-[4-(4-fluorophenyl)-piperazin-1-yl]-methyl}-cyclohexyl)-(3-fluorophenyl)-methyl]-dimethylamine | 653.39 |
| 123. | [(4-{(4-benzyl-5-pyrrolidin-1-yl-oxazol-2-yl)-[4-(4-methoxyphenyl)-piperazin-1-yl]-methyl}-cyclohexyl)-(3-fluorophenyl)-methyl]-dimethylamine | 665.41 |
| 124. | [(4-{(4-benzyl-5-morpholin-4-yl-oxazol-2-yl)-[4-(4-methoxyphenyl)-piperazin-1-yl]-methyl}-cyclohexyl)-(3-fluorophenyl)-methyl]-dimethylamine | 681.41 |
| 125. | [{4-[(4-benzyl-5-pyrrolidin-1-yl-oxazol-2-yl)-(3,4-dihydro-1H-isoquinolin-2-yl)-methyl]-cyclohexyl}-(3-fluorophenyl)-methyl]-dimethylamine | 606.37 |
| 126. | [{4-[(4-benzyl-5-morpholin-4-yl-oxazol-2-yl)-(3,4-dihydro-1H-isoquinolin-2-yl)-methyl]-cyclohexyl}-(3-fluorophenyl)-methyl]-dimethylamine | 622.37 |
| 127. | [{4-[{4-benzyl-5-[4-(4-methoxy-phenyl)-piperazin-1-yl]-oxazol-2-yl}-(3,4-dihydro-1H-isoquinolin-2-yl)-methyl]-cyclohexyl}-(3-fluorophenyl)-methyl]-dimethylamine | 727.43 |
| 128. | [{4-[[4-benzyl-5-(2,6-dimethyl-morpholin-4-yl)-oxazol-2-yl]-(3,4-dihydro-1H-isoquinolin-2-yl)-methyl]-cyclohexyl}-(3-fluorophenyl)-methyl]-dimethylamine | 650.40 |

-continued

| No. | Name | Mass |
|---|---|---|
| 129. | [{4-[(4-benzyl-5-pyrrolidin-1-yl-oxazol-2-yl)-morpholin-4-yl-methyl]-cyclohexyl}-(4-chlorophenyl)-methyl]-dimethylamine | 576.32 |
| 130. | [{4-[(4-benzyl-5-morpholin-4-yl-oxazol-2-yl)-morpholin-4-yl-methyl]-cyclohexyl}-(4-chlorophenyl)-methyl]-dimethylamine | 592.32 |
| 131. | [[4-({4-benzyl-5-[4-(4-methoxyphenyl)-piperazin-1-yl]-oxazol-2-yl}-morpholin-4-yl-methyl)-cyclohexyl]-(4-chlorophenyl)-methyl]-dimethylamine | 697.38 |
| 132. | [(4-{[4-benzyl-5-(2,6-dimethylmorpholin-4-yl)-oxazol-2-yl]-morpholin-4-yl-methyl}-cyclohexyl)-(4-chlorophenyl)-methyl]-dimethylamine | 620.35 |
| 133. | [(4-{(4-benzyl-5-pyrrolidin-1-yl-oxazol-2-yl)-[4-(4-fluorophenyl)-piperazin-1-yl]-methyl}-cyclohexyl)-(4-chlorophenyl)-methyl]-dimethylamine | 669.36 |
| 134. | [(4-{(4-benzyl-5-pyrrolidin-1-yl-oxazol-2-yl)-[4-(4-methoxyphenyl)-piperazin-1-yl]-methyl}-cyclohexyl)-(4-chlorophenyl)-methyl]-dimethylamine | 681.38 |
| 135. | [(4-{(4-benzyl-5-morpholin-4-yl-oxazol-2-yl)-[4-(4-methoxyphenyl)-piperazin-1-yl]-methyl}-cyclohexyl)-(4-chlorophenyl)-methyl]-dimethylamine | 697.38 |
| 136. | [(4-{[4-benzyl-5-(2,6-dimethylmorpholin-4-yl)-oxazol-2-yl]-[4-(4-methoxy-phenyl)-piperazin-1-yl]-methyl}-cyclohexyl)-(4-chlorophenyl)-methyl]-dimethylamine | 725.41 |
| 137. | [{4-[(4-benzyl-5-pyrrolidin-1-yl-oxazol-2-yl)-(3,4-dihydro-1H-isoquinolin-2-yl)-methyl]-cyclohexyl}-(4-chlorophenyl)-methyl]-dimethylamine | 622.34 |
| 138. | ({4-[(4-benzyl-5-pyrrolidin-1-yl-oxazol-2-yl)-morpholin-4-yl-methyl]-cyclohexyl}-thiophen-2-yl-methyl)-dimethylamine | 548.32 |
| 139. | ({4-[(4-benzyl-5-morpholin-4-yl-oxazol-2-yl)-morpholin-4-yl-methyl]-cyclohexyl}-thiophen-2-yl-methyl)-dimethylamine | 564.31 |
| 140. | {[4-({4-benzyl-5-[4-(4-methoxyphenyl)-piperazin-1-yl]-oxazol-2-yl}-morpholin-4-yl-methyl)-cyclohexyl]-thiophen-2-yl-methyl}-dimethylamine | 669.37 |
| 141. | [(4-{[4-benzyl-5-(2,6-dimethylmorpholin-4-yl)-oxazol-2-yl]-morpholin-4-yl-methyl}-cyclohexyl)-thiophen-2-yl-methyl]-dimethylamine | 592.34 |
| 142. | [(4.-{(4-benzyl-5-pyrrolidin-1-yl-oxazol-2-yl)-[4-(4-fluorophenyl)-piperazin-1-yl]-me.thyl}-cyclohexyl)-thiophen-2-yl-methyl]-dimethylamine | 641.36 |
| 143. | [(4-{(4-benzyl-5-pyrrolidin-1-yl-oxazol-2-yl)-[4-(4-methoxyphenyl)-piperazin-1-yl]-methyl}-cyclohexyl)-thiophen-2-yl-methyl]-dimethylamine | 653.38 |
| 144. | (4-{(4-benzyl-5-morpholin-4-yl-oxazol-2-yl)-[4-(4-methoxy-phenyl)-piperazin-1-yl]-methyl}-cyclohexyl)-thiophen-2-yl-methyl]-dimethylamine | 669.37 |
| 145. | [(4-{[4-benzyl-5-(2,6-dimethylmorpholin-4-yl)-oxazol-2-yl]-[4-(4-methoxy-phenyl)-piperazin-1-yl]-methyl}-cyclohexyl)-thiophen-2-yl-methyl]-dimethylamine | 697.40 |
| 146. | ({4-[(4-benzyl-5-pyrrolidin-1-yl-oxazol-2-yl)-(3,4-dihydro-1H-isoquinolin-2-yl)-methyl]-cyclohexyl}-thiophen-2-yl-methyl)-dimethylamine | 594.34 |
| 147. | ({4-[{4-benzyl-5-[4-(4-methoxyphenyl)-piperazin-1-yl]-oxazol-2-yl}-(3,4-dihydro-1H-isoquinolin-2-yl)-methyl]-cyclohexyl}-thiophen-2-yl-methyl)-dimethylamine | 715.39 |
| 148. | ({4-[[4-benzyl-5-(2,6-dimethylmorpholin-4-yl)-oxazol-2-yl]-(3,4-dihydro-1H-isoquinolin-2-yl)-methyl]-cyclohexyl}-thiophen-2-yl-methyl)-dimethylamine | 638.37 |
| 149. | [{4-[2-(4-benzyl-5-pyrrolidin-1-yl-oxazol-2-yl)-2-morpholin-4-yl-ethyl]-cyclohexyl}-(3-fluorophenyl)-methyl]-dimethylamine | 574.37 |
| 150. | [{4-[2-(4-benzyl-5-morpholin-4-yl-oxazol-2-yl)-2-morpholin-4-yl-ethyl]-cyclohexyl}-(3-fluorophenyl)-methyl]-dimethylamine | 590.36 |
| 151. | [[4-(2-{4-benzyl-5-[4-(4-methoxyphenyl)-piperazin-1-yl]-oxazol-2-yl}-2-morpholin-4-yl-ethyl)-cyclohexyl]-(3-fluorophenyl)-methyl]-dimethylamine | 695.42 |
| 152. | [(4-{2-[4-benzyl-5-(2,6-dimethylmorpholin-4-yl)-oxazol-2-yl]-2-morpholin-4-yl-ethyl}-cyclohexyl)-(3-fluorophenyl)-methyl]-dimethylamine | 618.39 |
| 153. | [(4-{2-[4-benzyl-5-(2,6-dimethylmorpholin-4-yl)-oxazol-2-yl]-2-[4-(4-fluorophenyl)-piperazin-1-yl]-ethyl}-cyclohexyl)-(3-fluorophenyl)-methyl]-dimethylamine | 711.43 |
| 154. | [(4-{2-(4-benzyl-5-morpholin-4-yl-oxazol-2-yl)-2-[4-(4-methoxy-phenyl)-piperazin-1-yl]-ethyl}-cyclohexyl)-(3-fluorophenyl)-methyl]-dimethylamine | 695.42 |
| 155. | [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-(3-fluorophenyl)-methyl]-dimethylamine | 800.48 |
| 156. | [(4-{2-[4-benzyl-5-(2,6-dimethylmorpholin-4-yl)-oxazol-2-yl]-2-[4-(4-methoxyphenyl)-piperazin-1-yl]-ethyl}-cyclohexyl)-(3-fluorophenyl)-methyl]-dimethylamine | 723.45 |
| 157. | [{4-[2-{4-benzyl-5-[4-(4-methoxy-phenyl)-piperazin-1-yl]-oxazol-2-yl}-2-(3,4-dihydro-1H-isoquinolin-2-yl)-ethyl]-cyclohexyl}-(3-fluorophenyl)-methyl]-dimethylamine | 741.44 |
| 158. | ({4-[2-(4-benzyl-5-morpholin-4-yl-oxazol-2-yl)-2-morpholin-4-yl-ethyl]-cyclohexyl}-thiophen-2-yl-methyl)-dimethylamine | 578.33 |
| 159. | {[4-(2-{4-benzyl-5-[4-(4-methoxyphenyl)-piperazin-1-yl]-oxazol-2-yl}-2-morpholin-4-yl-ethyl)-cyclohexyl]-thiophen-2-yl-methyl}-dimethylamine | 683.39 |
| 160. | [(4-{2-[4-benzyl-5-(2,6-dimethyl-morpholin-4-yl)-oxazol-2-yl]-2-morpholin-4-yl-ethyl}-cyclohexyl)-thiophen-2-yl-methyl]-dimethylamine | 606.36 |
| 161. | [(4-{2-(4-benzyl-5-morpholin-4-yl-oxazol-2-yl)-2-[4-(4-fluorophenyl)-piperazin-1-yl]-ethyl}-cyclohexyl)-thiophen-2-yl-methyl]-dimethylamine | 671.37 |
| 162. | [(4-{2-{4-benzyl-5-[4-(4-methoxy-phenyl)-piperazin-1-yl]-oxazol-2-yl}-2-[4-(4-fluorophenyl)-piperazin-1-yl]-ethyl}-cyclohexyl)-thiophen-2-yl-methyl]-dimethylamine | 776.42 |

| No. | Name | Mass |
|---|---|---|
| 163. | [(4-{2-(4-benzyl-5-pyrrolidin-1-yl-oxazol-2-yl)-2-[4-(4-methoxyphenyl)-piperazin-1-yl]-ethyl}-cyclohexyl)-thiophen-2-yl-methyl]-dimethylamine | 667.39 |
| 164. | [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-thiophen-2-yl-methyl]-dimethylamine | 788.44 |
| 165. | [(4-{2-[4-benzyl-5-(2,6-dimethyl-morpholin-4-yl)-oxazol-2-yl]-2-[4-(4-methoxyphenyl)-piperazin-1-yl]-ethyl}-cyclohexyl)-thiophen-2-yl-methyl]-dimethylamine | 711.42 |
| 166. | ({4-[2-{4-benzyl-5-[4-(4-methoxy-phenyl)-piperazin-1-yl]-oxazol-2-yl}-2-(3,4-dihydro-1H-isoquinolin-2-yl)-ethyl]-cyclohexyl}-thiophen-2-yl-methyl)-dimethylamine | 729.41 |

Investigations on the Efficacy of the Compounds According to the Invention

The data obtained in the following assays are summarized in Table 1.

Method for Determining the Affinity for the Human μ-Opiate Receptor

The receptor affinity for the human μ-opiate receptor is determined in a homogeneous batch in microtiter plates. For this purpose dilution series of the substances to be tested are incubated for 90 minutes at room temperature with a receptor membrane preparation (15-40 μg protein/250 μl incubation batch) of CHO-K1 cells, which express the human μ-opiate receptor (RB-HOM receptor membrane preparation from the Nen company, Zaventem, Belgium), in the presence of 1 nmole/l of the radioactive ligand [$^3$H]-naloxone (NET719, Nen company, Zaventem, Belgium) and 1 mg WGA-SPA beads (wheat germ agglutinin SPA beads from Amersham/Pharmacia, Freiburg, Germany) in a total volume of 250 μl. 50 mmole/l of Tris-HCl supplemented with 0.05% sodium azide and with 0.06% bovine serum albumin is used as incubation buffer. In order to determine the non-specific binding, 25 μmole/l of naloxone is additionally added. After the end of the 90 minutes' incubation time the microtiter plates are centrifuged for 20 minutes at 1000 g and the radioactivity is measured in a beta counter (Microbeta-Trilux, PerkinElmer Wallac, Freiburg, Germany). The percentage displacement of the radioactive ligand from its binding to the human μ-opiate receptor at a concentration of the test substances of 1 μmole/l is determined and is given as percentage inhibition of the specific binding.

| | n | $R^2$ | $R^3$ | $R^4$ | $R^1$ | $R^7$ | $R^8$ | μ-opioid receptor, % inhibition [1 μM] |
|---|---|---|---|---|---|---|---|---|
| 17 | 0 | 4-F-C$_6$H$_4$-CH(−)− | ]—(CH$_2$)$_5$—[ | | CH$_2$Ph | ]—(CH$_2$)$_4$—[ | | 76 |
| 18 | 0 | 4-F-C$_6$H$_4$-CH(−)− | Me | Ph | CH$_2$Ph | ]—(CH$_2$)$_2$—O—(CH$_2$)$_2$—[ | | 65 |
| 19 | 0 | 4-F-C$_6$H$_4$-CH(−)− | Me | Ph | CH$_2$Ph | ]—(CH$_2$)$_2$—CH(CH$_3$)—(CH$_2$)$_2$—[ | | 63 |

-continued
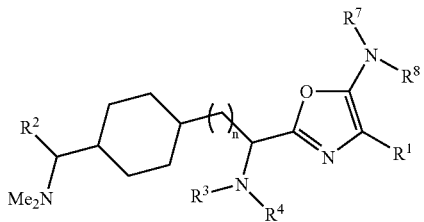
| | n | R² | R³ | R⁴ | R¹ | R⁷ | R⁸ | μ-opioid receptor, % inhibition [1 μM] |
|---|---|---|---|---|---|---|---|---|
| 20 | 0 | 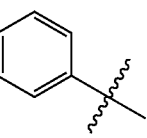 | Et | Et | CH₂Ph | 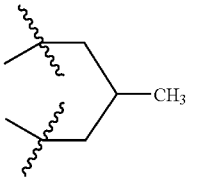 | | 63 |
| 21 | 0 | 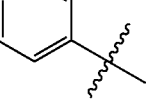 | Et | Et | CH₂Ph | Me | CH₂Ph | 72 |
| 22 | 0 | 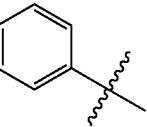 | Me | CH₂Ph | CH₂Ph | Me | CH₂Ph | 64 |
| 23 | 0 | 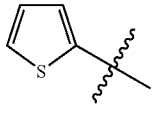 | ]—(CH₂)₅—[ | | CH₂Ph | 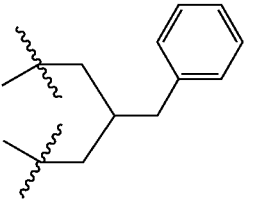 | | 70 |
| 24 | 0 | 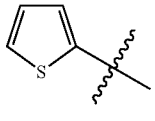 | ]—(CH₂)₅—[ | | CH₂Ph | 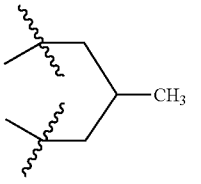 | | 70 |
| 25 | 0 | 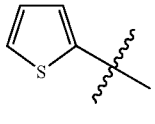 | ]—(CH₂)₅—[ | | CH₂Ph | Me | CH₂Ph | 80 |
| 26 | 0 | 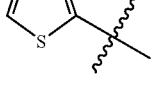 | ]—(CH₂)₅—[ | | CH₂Ph | 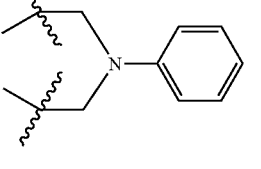 | | 85 |

-continued

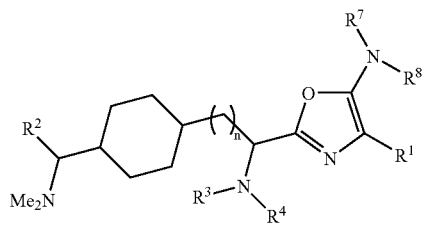

| | n | R² | R³ | R⁴ | R¹ | R⁷ | R⁸ | μ-opioid receptor, % inhibition [1 μM] |
|---|---|---|---|---|---|---|---|---|
| 27 | 0 | 2-thienyl | Et | Et | CH₂Ph | \_/CH(CH₂Ph)\\\_ (R⁷,R⁸ joined, 4-benzyl) | | 78 |
| 28 | 0 | 2-thienyl | Et | Et | CH₂Ph | \_/N(CH₂Ph)\\\_ (R⁷,R⁸ joined piperazine with N-benzyl) | | 72 |
| 29 | 0 | 2-thienyl | Et | Et | CH₂Ph | \_/CH(CH₃)\\\_ (R⁷,R⁸ joined, 4-methyl) | | 95 |
| 30 | 0 | 2-thienyl | Et | Et | CH₂Ph | Me | CH₂Ph | 92 |
| 31 | 0 | 2-thienyl | Et | Et | CH₂Ph | \_/N(Ph)\\\_ (R⁷,R⁸ joined piperazine with N-phenyl) | | 62 |
| 32 | 0 | 2-thienyl | \_/N(CH₂Ph)\\\_ (R³,R⁴ joined piperazine N-benzyl) | | CH₂Ph | \_/CH(CH₂Ph)\\\_ (R⁷,R⁸ joined, 4-benzyl) | | 75 |

-continued
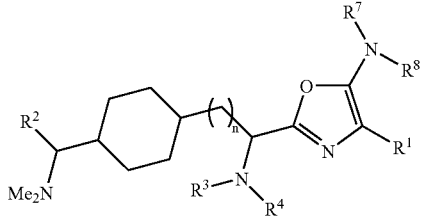
| | n | R² | R³ | R⁴ | R¹ | R⁷ | R⁸ | μ-opioid receptor, % inhibition [1 μM] |
|---|---|---|---|---|---|---|---|---|
| 33 | 0 | 4-F-C₆H₄ | ]—(CH₂)₅—[ | | CH₂Ph | 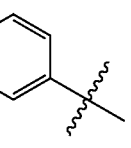 | | 65 |
| 34 | 0 | 4-F-C₆H₄ | Et | Et | CH₂Ph | Me | (CH₂)₂Ph | 84 |
| 35 | 0 | 4-F-C₆H₄ | Et | Et | CH₂Ph | Et | Et | 61 |
| 36 | 0 | 4-F-C₆H₄ | Et | Et | CH₂Ph | 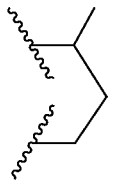 | | 69 |
| 37 | 0 | 4-F-C₆H₄ | Me | Ph | CH₂Ph | 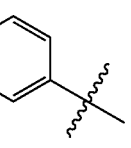 | | 68 |
| 38 | 0 | 4-F-C₆H₄ | Me | Ph | CH₂Ph | Me | (CH₂)₂Ph | 62 |
| 39 | 0 | 4-Cl-C₆H₄ | ]—(CH₂)₅—[ | | CH₂Ph | Et | Et | 75 |

-continued
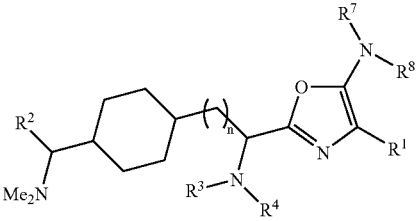
| | n | R² | R³ | R⁴ | R¹ | R⁷ | R⁸ | μ-opioid receptor, % inhibition [1 μM] |
|---|---|---|---|---|---|---|---|---|
| 40 | 0 | Cl-C₆H₄- 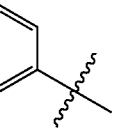 | ]—(CH₂)₅—[ | | CH₂Ph | 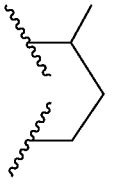 | | 60 |
| 41 | 0 | Cl-C₆H₄- 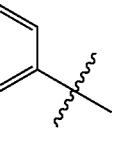 | Et | Et | CH₂Ph | 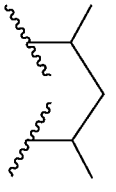 | | 64 |
| 42 | 0 | Cl-C₆H₄- 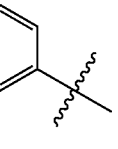 | Me | Ph | CH₂Ph | 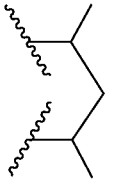 | | 79 |
| 43 | 0 | Cl-C₆H₄- 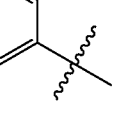 | Me | Ph | CH₂Ph | Me | (CH₂)₂Ph | 72 |
| 44 | 0 | Cl-C₆H₄- 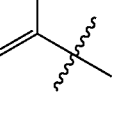 | 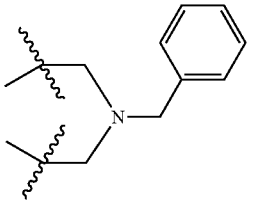 | | CH₂Ph | Et | Et | 67 |
| 45 | 0 | 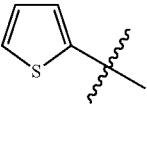 | ]—(CH₂)₅—[ | | CH₂Ph | 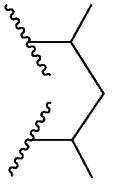 | | 71 |
| 46 | 0 | 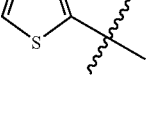 | ]—(CH₂)₅—[ | | CH₂Ph | Me | (CH₂)₂Ph | 80 |

-continued
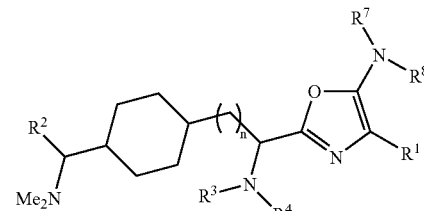
| | n | R² | R³ | R⁴ | R¹ | R⁷ | R⁸ | μ-opioid receptor, % inhibition [1 μM] |
|---|---|---|---|---|---|---|---|---|
| 47 | 0 | 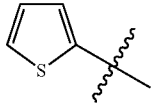 | ]—(CH₂)₅—[ | | CH₂Ph | Et | Et | 73 |
| 48 | 0 | 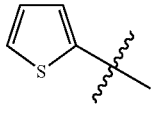 | ]—(CH₂)₅—[ | | CH₂Ph | ]—(CH₂)₂—S—(CH₂)₂—[ | | 60 |
| 49 | 0 | 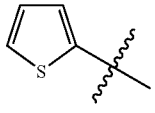 | Et | Et | CH₂Ph | Me | (CH₂)₂Ph | 90 |
| 50 | 0 | 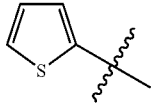 | Et | Et | Ch₂Ph | Et | Et | 83 |
| 51 | 0 | 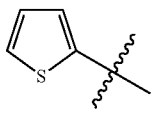 | Et | Et | CH₂Ph | 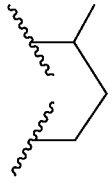 | | 100 |
| 52 | 0 | 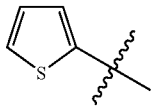 | Me | Ph | CH₂Ph | ]—(CH₂)₂—S—(CH₂)₂—[ | | 92 |
| 53 | 0 | 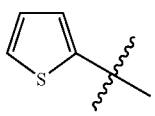 | 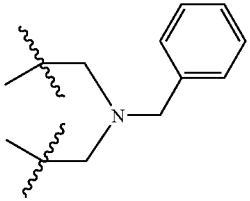 | | CH₂Ph | 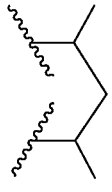 | | 86 |
| 54 | 0 | 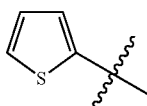 | 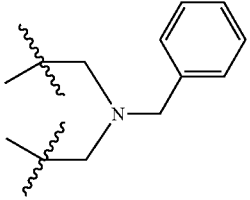 | | CH₂Ph | Me | (CH₂)₂Ph | 74 |

-continued
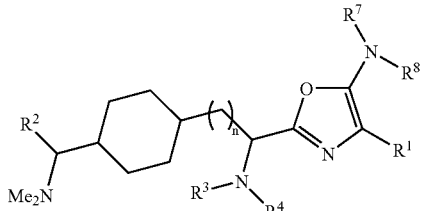
| | n | R² | R³ | R⁴ | R¹ | R⁷ | R⁸ | μ-opioid receptor, % inhibition [1 μM] |
|---|---|---|---|---|---|---|---|---|
| 55 | 0 | 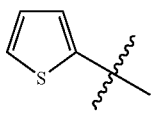 | 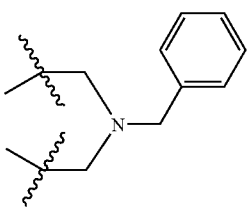 | | CH₂Ph | ]—(CH₂)₂—S—(CH₂)₂—[ | | 63 |
| 56 | 1 | 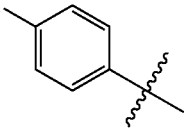 | ]—(CH₂)₅—[ | | CH₂Ph | 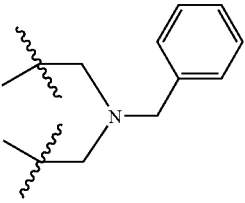 | | 62 |
| 57 | 1 | 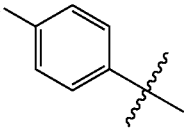 | ]—(CH₂)₅—[ | | CH₂Ph | 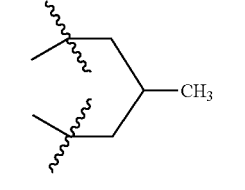 | | 64 |
| 58 | 1 | 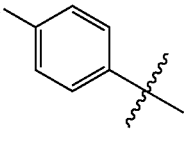 | ]—(CH₂)₅—[ | | CH₂Ph | Me | CH₂Ph | 73 |
| 59 | 1 | 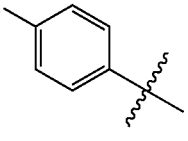 | Et | Et | CH₂Ph | 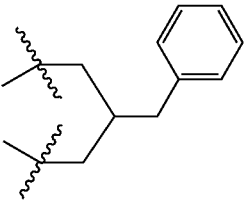 | | 60 |
| 60 | 1 | 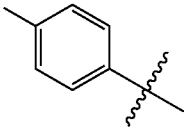 | Et | Et | CH₂Ph | 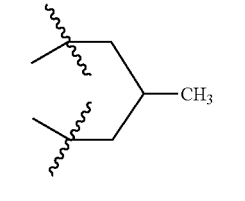 | | 68 |

-continued
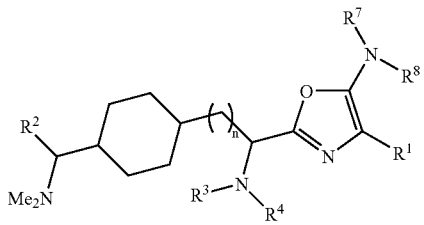
| | n | R² | R³ | R⁴ | R¹ | R⁷ | R⁸ | μ-opioid receptor, % inhibition [1 μM] |
|---|---|---|---|---|---|---|---|---|
| 61 | 1 | 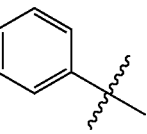 | Et | Et | CH₂Ph | Me | CH₂Ph | 76 |
| 62 | 1 | 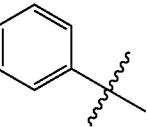 | 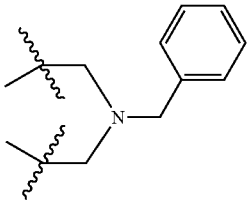 | | CH₂Ph | 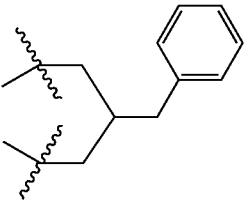 | | 87 |
| 63 | 1 | 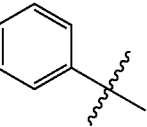 | 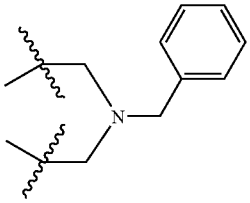 | | CH₂Ph | 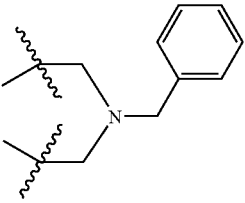 | | 78 |
| 64 | 1 | 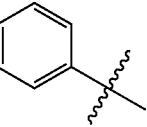 | 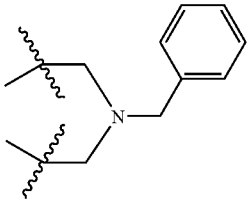 | | CH₂Ph | 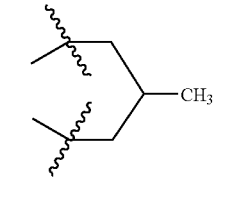 | | 69 |
| 65 | 1 | 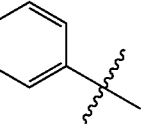 | ]—(CH₂)₅—[ | | CH₂Ph | 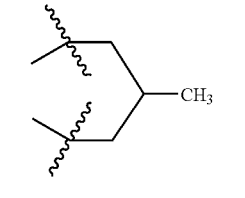 | | 61 |
| 66 | 1 | 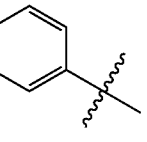 | ]—(CH₂)₅—[ | | CH₂Ph | Me | CH₂Ph | 65 |

-continued
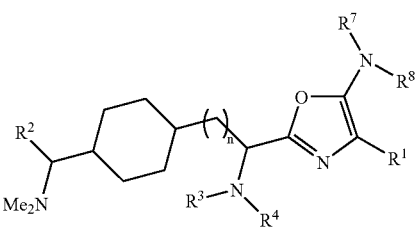
|  | n | R² | R³ | R⁴ | R¹ | R⁷ | R⁸ | μ-opioid receptor, % inhibition [1 μM] |
|---|---|---|---|---|---|---|---|---|
| 67 | 1 | 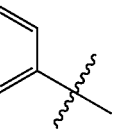 | Et | Et | CH₂Ph | 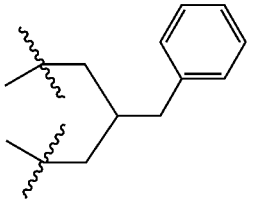 | | 64 |
| 68 | 1 | 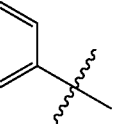 | Et | Et | CH₂Ph | 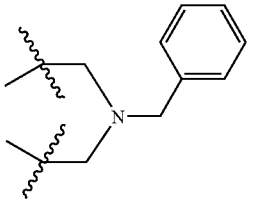 | | 60 |
| 69 | 1 | 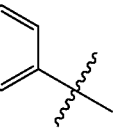 | Et | Et | CH₂Ph | 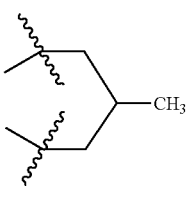 | | 82 |
| 70 | 1 | 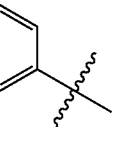 | Et | Et | CH₂Ph | Me | CH₂Ph | 60 |
| 71 | 1 | 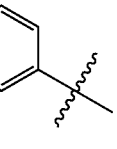 | 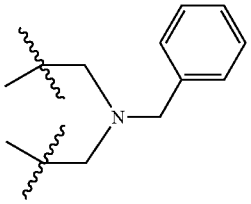 | | CH₂Ph | 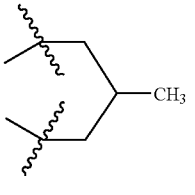 | | 67 |
| 72 | 1 | 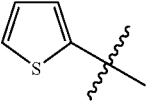 | ]—(CH₂)₅—[ | | CH₂Ph | 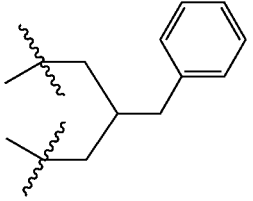 | | 69 |

-continued
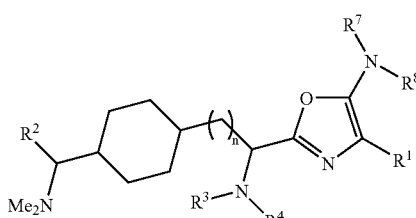
| | n | R² | R³ | R⁴ | R¹ | R⁷ | R⁸ | μ-opioid receptor, % inhibition [1 μM] |
|---|---|---|---|---|---|---|---|---|
| 73 | 1 | 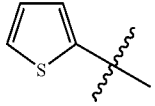 | ]—(CH₂)₅—[ | | CH₂Ph | 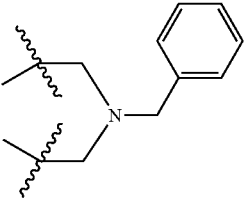 | | 94 |
| 74 | 1 | 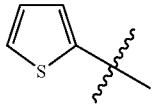 | ]—(CH₂)₅—[ | | CH₂Ph | 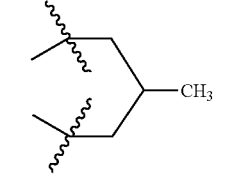 | | 79 |
| 75 | 1 | 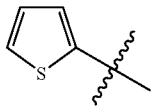 | ]—(CH₂)₅—[ | | CH₂Ph | Me | CH₂Ph | 90 |
| 76 | 1 | 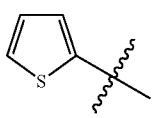 | ]—(CH₂)₅—[ | | CH₂Ph | 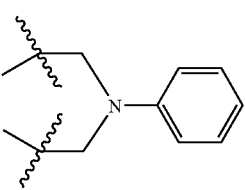 | | 94 |
| 77 | 1 | 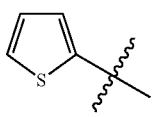 | Et | Et | CH₂Ph | 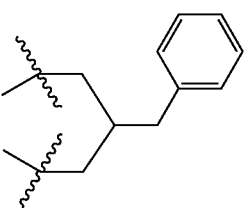 | | 91 |
| 78 | 1 | 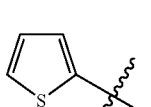 | Et | Et | CH₂Ph | 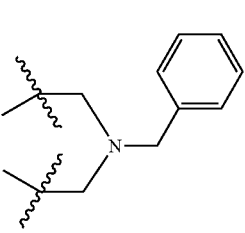 | | 100 |

-continued
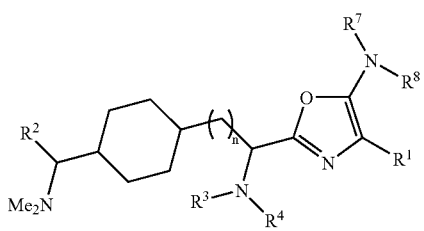
| | n | R² | R³ | R⁴ | R¹ | R⁷ | R⁸ | μ-opioid receptor, % inhibition [1 μM] |
|---|---|---|---|---|---|---|---|---|
| 79 | 1 | 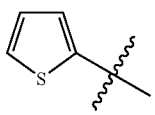 | Et | Et | CH₂Ph | 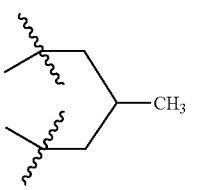 | | 97 |
| 80 | 1 | 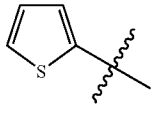 | Et | Et | CH₂Ph | Me | CH₂Ph | 93 |
| 81 | 1 | 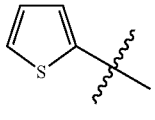 | 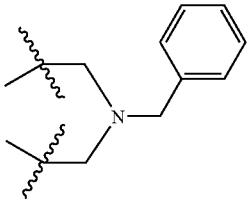 | | CH₂Ph | 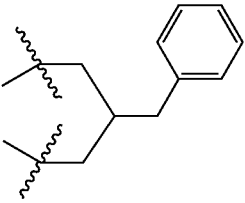 | | 81 |
| 82 | 1 | 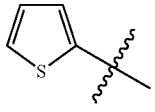 | 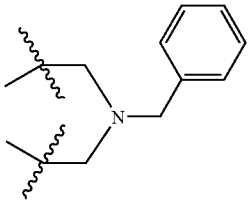 | | CH₂Ph | 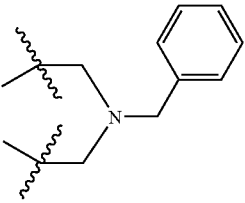 | | 83 |
| 83 | 1 | 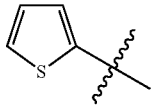 | 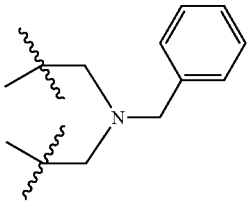 | | CH₂Ph | 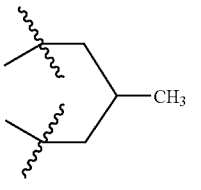 | | 97 |
| 84 | 1 | 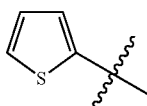 | 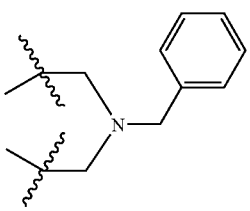 | | CH₂Ph | Me | CH₂Ph | 88 |

-continued
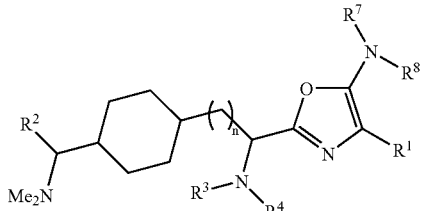
| | n | R² | R³ | R⁴ | R¹ | R⁷ | R⁸ | µ-opioid receptor, % inhibition [1 µM] |
|---|---|---|---|---|---|---|---|---|
| 85 | 1 | 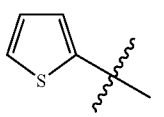 | 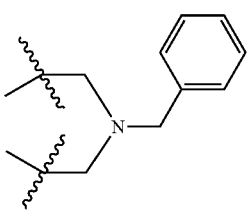 | | CH₂Ph | 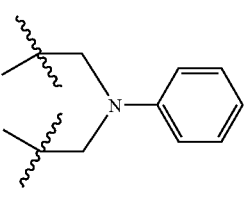 | | 91 |
| 86 | 1 | 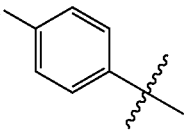 | ]—(CH₂)₅—[ | | CH₂Ph | Me | (CH₂)₂Ph | 63 |
| 87 | 1 | 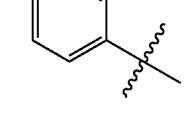 | ]—(CH₂)₅—[ | | CH₂Ph | Et | Et | 64 |
| 88 | 1 | 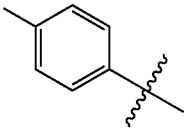 | Et | Et | CH₂Ph | 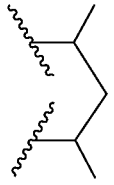 | | 79 |
| 89 | 1 | 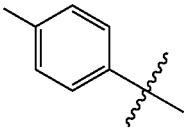 | Et | Et | CH₂Ph | Me | (CH₂)₂Ph | 87 |
| 90 | 1 | 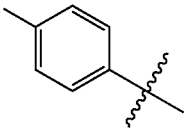 | Et | Et | CH₂Ph | Et | Et | 89 |
| 91 | 1 | 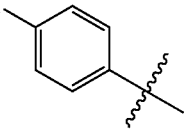 | Et | Et | CH₂Ph | ]—(CH₂)₂—S—(CH₂)₂—[ | | 75 |

-continued

| | n | R² | R³ | R⁴ | R¹ | R⁷ | R⁸ | μ-opioid receptor, % inhibition [1 μM] |
|---|---|---|---|---|---|---|---|---|
| 92 | 1 | 4-Cl-C₆H₄ | Me | Ph | CH₂Ph | ]—(CH₂)₂—S—(CH₂)₂—[ | | 87 |
| 93 | 1 | 4-Cl-C₆H₄ | —CH₂—N(CH₂Ph)—CH₂— (cyclic) | | CH₂Ph | Me | (CH₂)₂Ph | 66 |
| 94 | 1 | 4-Cl-C₆H₄ | —CH₂—N(CH₂Ph)—CH₂— (cyclic) | | CH₂Ph | Et | Et | 74 |
| 95 | 1 | 4-F-C₆H₄ | ]—(CH₂)₅—[ | | CH₂Ph | Me | (CH₂)₂Ph | 65 |
| 96 | 1 | 4-F-C₆H₄ | Et | Et | CH₂Ph | ]—CH(Me)—CH₂—CH(Me)—[ | | 80 |
| 97 | 1 | 4-F-C₆H₄ | Et | Et | CH₂Ph | Me | (CH₂)₂Ph | 85 |
| 98 | 1 | 4-F-C₆H₄ | Et | Et | CH₂Ph | Et | Et | 77 |

-continued
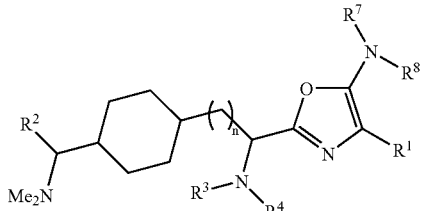
| | n | R² | R³ | R⁴ | R¹ | R⁷ | R⁸ | µ-opioid receptor, % inhibition [1 µM] |
|---|---|---|---|---|---|---|---|---|
| 99 | 1 | 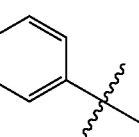 4-F-C₆H₄ | Et | Et | CH₂Ph | ]—(CH₂)₂—S—(CH₂)₂—[ | | 62 |
| 100 | 1 | 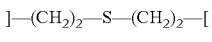 4-F-C₆H₄ | Et | Et | CH₂Ph | 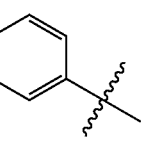 | | 86 |
| 101 | 1 | 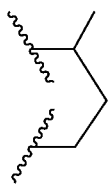 4-F-C₆H₄ | Me | Ph | CH₂Ph | 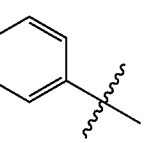 | | 68 |
| 102 | 1 | 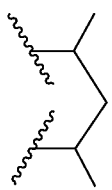 4-F-C₆H₄ | Me | Ph | CH₂Ph | Me | (CH₂)₂Ph | 77 |
| 103 | 1 | 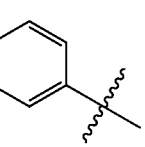 4-F-C₆H₄ | Me | Ph | CH₂Ph | Et | Et | 79 |
| 104 | 1 |  4-F-C₆H₄ | Me | Ph | CH₂Ph | ]—(CH₂)₂—S—(CH₂)₂—[ | | 89 |
| 105 | 1 | 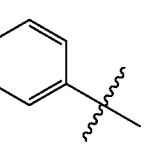 4-F-C₆H₄ | Me | Ph | CH₂Ph | 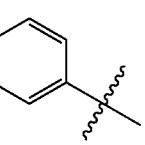 | | 71 |

-continued
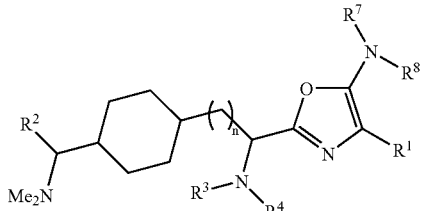
| | n | R² | R³ | R⁴ | R¹ | R⁷ | R⁸ | μ-opioid receptor, % inhibition [1 μM] |
|---|---|---|---|---|---|---|---|---|
| 106 | 1 | 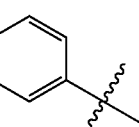 | 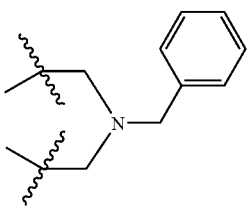 | | $CH_2Ph$ |  | | 61 |
| 107 | 1 | 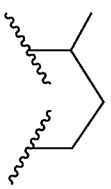 | ]—(CH₂)₅—[ | | $CH_2Ph$ | 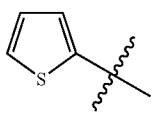 | | 84 |
| 108 | 1 | 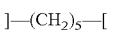 | ]—(CH₂)₅—[ | | $CH_2Ph$ | Me | $(CH_2)_2Ph$ | 88 |
| 109 | 1 |  | ]—(CH₂)₅—[ | | $CH_2Ph$ | Et | Et | 98 |
| 110 | 1 | 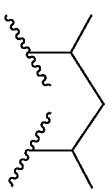 | ]—(CH₂)₅—[ | | $CH_2Ph$ | ]—(CH₂)₂—S—(CH₂)₂—[ | | 97 |
| 111 | 1 | 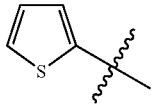 | ]—(CH₂)₅—[ | | $CH_2Ph$ | 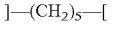 | | 92 |
| 112 | 1 |  | Et | Et | $CH_2Ph$ | 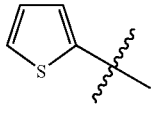 | | 89 |

-continued

[Structure: cyclohexane with Me₂N-CHR²- on one side, and -(CH₂)ₙ-CH(NR³R⁴)- linked to oxazole bearing R¹ and NR⁷R⁸ (with O in ring)]

| | n | R² | R³ | R⁴ | R¹ | R⁷ | R⁸ | μ-opioid receptor, % inhibition [1 μM] |
|---|---|---|---|---|---|---|---|---|
| 113 | 1 | 2-thienyl-CH< | Et | Et | CH₂Ph | Me | (CH₂)₂Ph | 97 |
| 114 | 1 | 2-thienyl-CH< | Et | Et | CH₂Ph | Et | Et | 94 |
| 115 | 1 | 2-thienyl-CH< | Et | Et | CH₂Ph | ]—(CH₂)₂—S—(CH₂)₂—[ | | 93 |
| 116 | 1 | 2-thienyl-CH< | Et | Et | CH₂Ph | ]—CH₂CH(CH₃)CH₂CH₂—[ (piperidine-like) | | 94 |
| 117 | 1 | 2-thienyl-CH< | Me | Ph | CH₂Ph | ]—CH₂CH(CH₃)CH₂CH₂—[ | | 99 |
| 118 | 1 | 2-thienyl-CH< | N-benzyl-bis(CH₂)— (piperazinyl) | | CH₂Ph | ]—(CH₂)₂—S—(CH₂)₂—[ | | 84 |
| 119 | 1 | 2-thienyl-CH< | N-benzyl-bis(CH₂)— (piperazinyl) | | CH₂Ph | ]—CH₂CH(CH₃)CH₂CH₂—[ | | 99 |

-continued

[Structure: cyclohexane with Me₂N-CHR² group on one side, and -(CH₂)ₙ-CH(NR³R⁴)- linker to an oxazole bearing R¹ at 4-position and NR⁷R⁸ at 5-position]

| | n | R² | R³ | R⁴ | R¹ | R⁷ | R⁸ | μ-opioid receptor, % inhibition [1 μM] |
|---|---|---|---|---|---|---|---|---|
| 120 | 0 | 3-F-C₆H₄- | ]—(CH₂)₂—O—(CH₂)₂—[ | | CH₂Ph | ]—(CH₂)₄—[ | | 75 |
| 121 | 0 | 3-F-C₆H₄- | ]—(CH₂)₂—O—(CH₂)₂—[ | | CH₂Ph | ]—(CH₂)₂—O—(CH₂)₂—[ | | 67 |
| 122 | 0 | 3-F-C₆H₄- | -CH₂CH₂-N(4-F-C₆H₄)-CH₂CH₂- | | CH₂Ph | ]—(CH₂)₄—[ | | 72 |
| 123 | 0 | 3-F-C₆H₄- | -CH₂CH₂-N(4-MeO-C₆H₄)-CH₂CH₂- | | CH₂Ph | ]—(CH₂)₄—[ | | 66 |
| 124 | 0 | 3-F-C₆H₄- | -CH₂CH₂-N(4-MeO-C₆H₄)-CH₂CH₂- | | CH₂Ph | ]—(CH₂)₂—O—(CH₂)₂—[ | | 60 |
| 125 | 0 | 3-F-C₆H₄- | 1,2-disubstituted benzene-CH₂- tether | | CH₂Ph | ]—(CH₂)₄—[ | | 83 |
| 126 | 0 | 3-F-C₆H₄- | 1,2-disubstituted benzene-CH₂- tether | | CH₂Ph | ]—(CH₂)₂—O—(CH₂)₂—[ | | 76 |

-continued
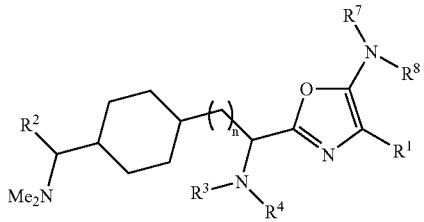
| | n | R² | R³ | R⁴ | R¹ | R⁷ | R⁸ | μ-opioid receptor, % inhibition [1 μM] |
|---|---|---|---|---|---|---|---|---|
| 127 | 0 | 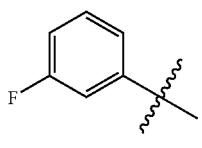 | 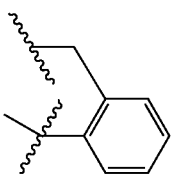 | | CH₂Ph | 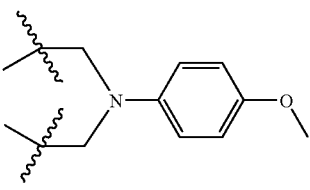 | | 73 |
| 128 | 0 | 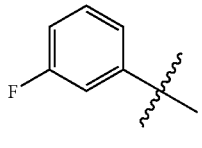 | 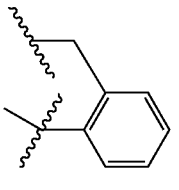 | | CH₂Ph | 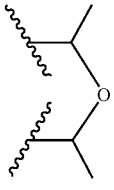 | | 71 |
| 129 | 0 | 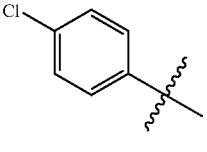 | ]—(CH₂)₂—O—(CH₂)₂—[ | | CH₂Ph | ]—(CH₂)₄—[ | | 75 |
| 130 | 0 | 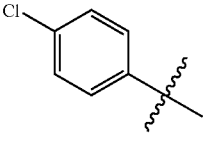 | ]—(CH₂)₂—O—(CH₂)₂—[ | | CH₂Ph | ]—(CH₂)₂—O—(CH₂)₂—[ | | 77 |
| 131 | 0 | 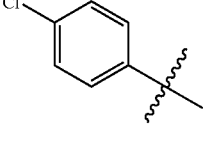 | ]—(CH₂)₂—O—(CH₂)₂—[ | | CH₂Ph | 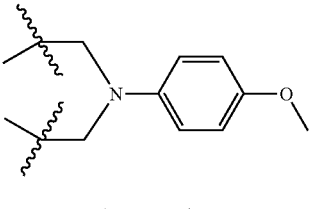 | | 64 |
| 132 | 0 | 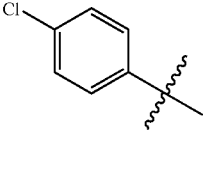 | ]—(CH₂)₂—O—(CH₂)₂—[ | | CH₂Ph | 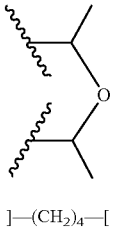 | | 64 |
| 133 | 0 | 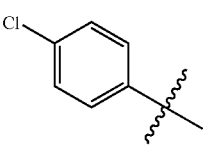 | 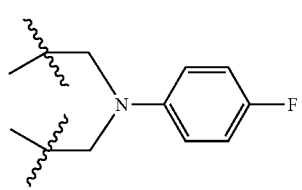 | | CH₂Ph | ]—(CH₂)₄—[ | | 64 |

-continued

| | n | R² | R³ | R⁴ | R¹ | R⁷ | R⁸ | µ-opioid receptor, % inhibition [1 µM] |
|---|---|---|---|---|---|---|---|---|
| 134 | 0 | 4-Cl-C₆H₄- | \[N(4-MeO-C₆H₄)-CH₂CH₂-, CH₂CH₂-\] | | CH₂Ph | ]—(CH₂)₄—[ | | 72 |
| 135 | 0 | 4-Cl-C₆H₄- | \[N(4-MeO-C₆H₄)-CH₂CH₂-, CH₂CH₂-\] | | CH₂Ph | ]—(CH₂)₂—O—(CH₂)₂—[ | | 70 |
| 136 | 0 | 4-Cl-C₆H₄- | \[N(4-MeO-C₆H₄)-CH₂CH₂-, CH₂CH₂-\] | | CH₂Ph | \[CH(CH₃)-O-CH(CH₃)\] | | 62 |
| 137 | 0 | 4-Cl-C₆H₄- | \[2-(CH₂)-C₆H₄-(CH₂)-\] | | CH₂Ph | ]—(CH₂)₄—[ | | 85 |
| 138 | 0 | 2-thienyl | ]—(CH₂)₂—O—(CH₂)₂—[ | | CH₂Ph | ]—(CH₂)₄—[ | | 91 |
| 139 | 0 | 2-thienyl | ]—(CH₂)₂—O—(CH₂)₂—[ | | CH₂Ph | ]—(CH₂)₂—O—(CH₂)₂—[ | | 72 |
| 140 | 0 | 2-thienyl | ]—(CH₂)₂—O—(CH₂)₂—[ | | CH₂Ph | \[N(4-MeO-C₆H₄)-CH₂CH₂-, CH₂CH₂-\] | | 67 |

-continued
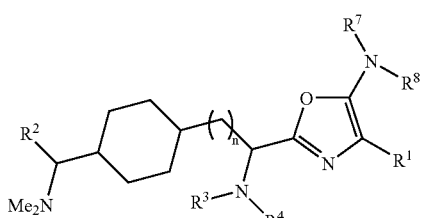
| | n | R² | R³ | R⁴ | R¹ | R⁷ | R⁸ | μ-opioid receptor, % inhibition [1 μM] |
|---|---|---|---|---|---|---|---|---|
| 141 | 0 | 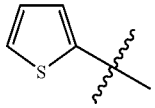 | ]—(CH₂)₂—O—(CH₂)₂—[ | | CH₂Ph | 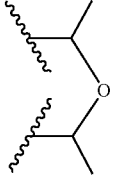 | | 65 |
| 142 | 0 | 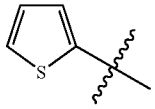 | 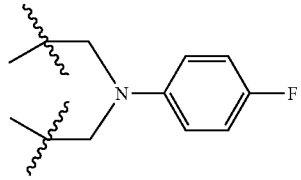 | | CH₂Ph | ]—(CH₂)₄—[ | | 85 |
| 143 | 0 | 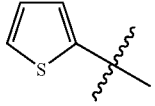 | 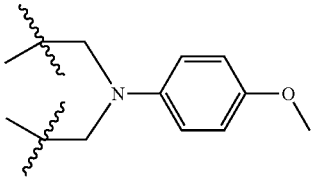 | | CH₂Ph | ]—(CH₂)₄—[ | | 77 |
| 144 | 0 | 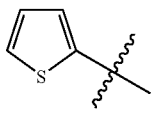 | 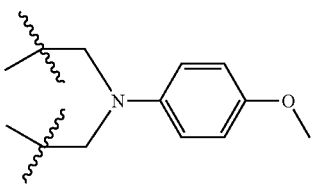 | | CH₂Ph | ]—(CH₂)₂—O—(CH₂)₂—[ | | 64 |
| 145 | 0 | 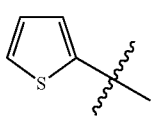 | 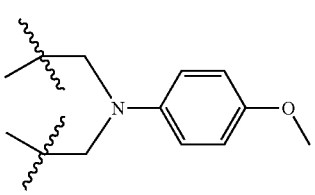 | | CH₂Ph | ]—(CH₂)₂—O—(CH₂)₂—[ | | 69 |
| 146 | 0 | 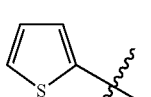 | 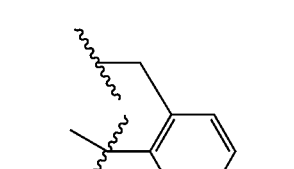 | | CH₂Ph | ]—(CH₂)₄—[ | | 92 |

-continued
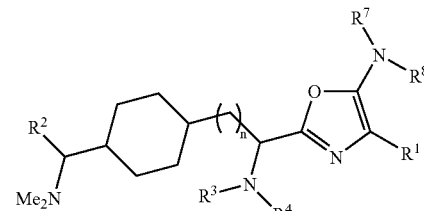
| | n | R² | R³ | R⁴ | R¹ | R⁷ | R⁸ | μ-opioid receptor, % inhibition [1 μM] |
|---|---|---|---|---|---|---|---|---|
| 147 | 0 | 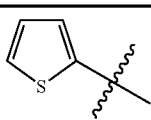 | 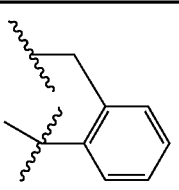 | | CH₂Ph | 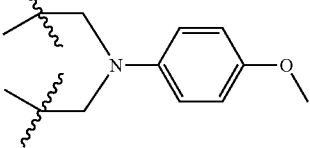 | | 91 |
| 148 | 0 | 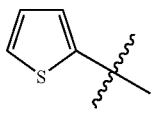 | 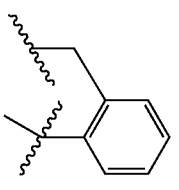 | | CH₂Ph | 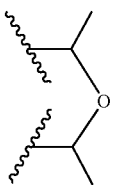 | | 84 |
| 149 | 1 | 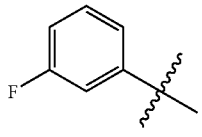 | ]—(CH₂)₂—O—(CH₂)₂—[ | | CH₂Ph | ]—(CH₂)₄—[ | | 87 |
| 150 | 1 | 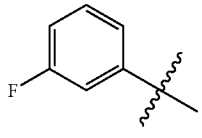 | ]—(CH₂)₂—O—(CH₂)₂—[ | | CH₂Ph | ]—(CH₂)₂—O—(CH₂)₂—[ | | 75 |
| 151 | 1 | 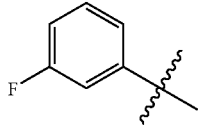 | ]—(CH₂)₂—O—(CH₂)₂—[ | | CH₂Ph | 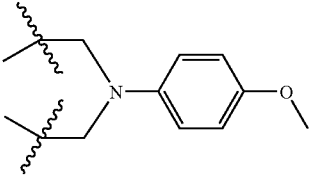 | | 89 |
| 152 | 1 | 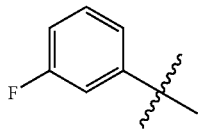 | ]—(CH₂)₂—O—(CH₂)₂—[ | | CH₂Ph | 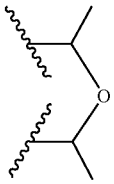 | | 65 |
| 153 | 1 | 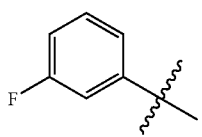 | 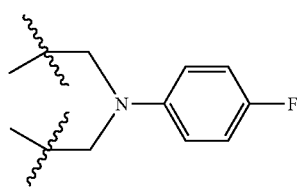 | | CH₂Ph | 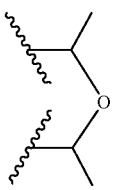 | | 71 |

-continued
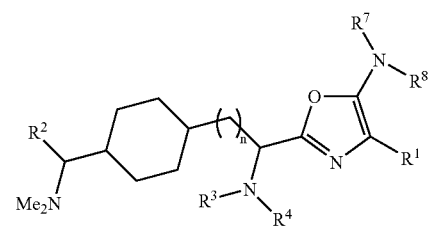
| | n | R² | R³ | R⁴ | R¹ | R⁷ | R⁸ | μ-opioid receptor, % inhibition [1 μM] |
|---|---|---|---|---|---|---|---|---|
| 154 | 1 | 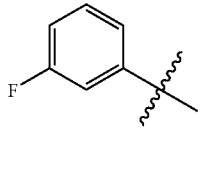 | 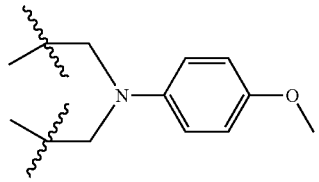 | | CH₂Ph | ]—(CH₂)₂—O—(CH₂)₂—[ | | 86 |
| 155 | 1 | 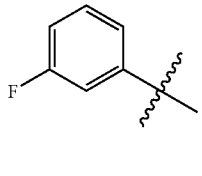 | 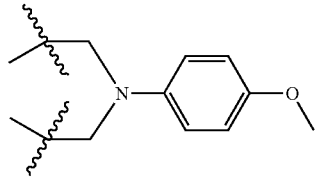 | | CH₂Ph | 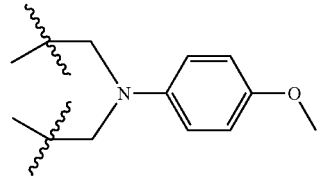 | | 82 |
| 156 | 1 | 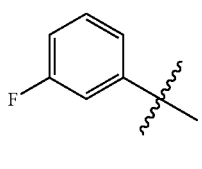 | 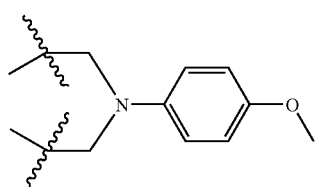 | | CH₂Ph | 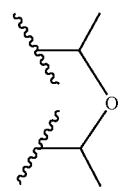 | | 74 |
| 157 | 1 | 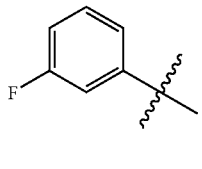 | 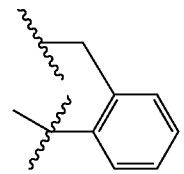 | | CH₂Ph | 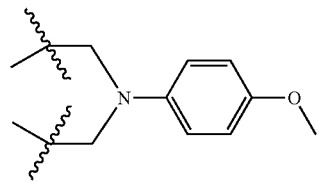 | | 84 |
| 158 | 1 | 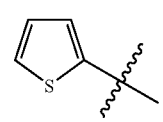 | ]—(CH₂)₂—O—(CH₂)₂—[ | | CH₂Ph | ]—(CH₂)₂—O—(CH₂)₂—[ | | 83 |
| 159 | 1 | 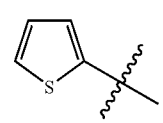 | ]—(CH₂)₂—O—(CH₂)₂—[ | | CH₂Ph | 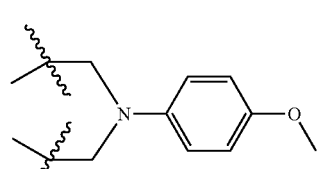 | | 94 |

-continued
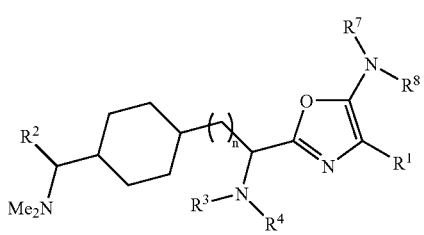
| | n | R² | R³ | R⁴ | R¹ | R⁷ | R⁸ | μ-opioid receptor, % inhibition [1 μM] |
|---|---|---|---|---|---|---|---|---|
| 160 | 1 | 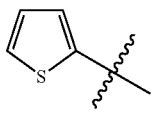 | ]—(CH₂)₂—O—(CH₂)₂—[ | | CH₂Ph | 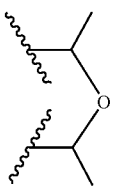 | | 79 |
| 161 | 1 | 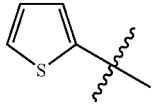 | 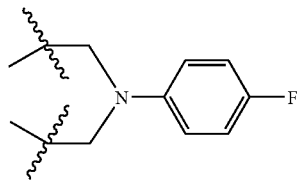 | | CH₂Ph | ]—(CH₂)₂—O—(CH₂)₂—[ | | 87 |
| 162 | 1 | 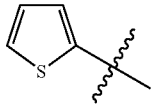 | 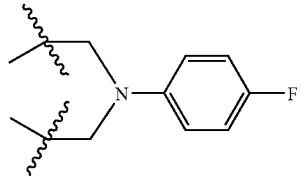 | | CH₂Ph | 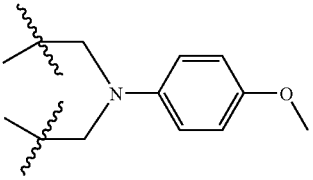 | | 96 |
| 163 | 1 | 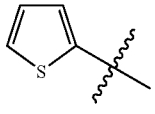 | 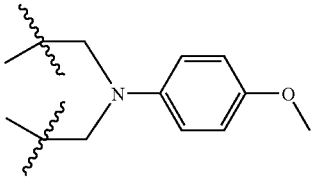 | | CH₂Ph | ]—(CH₂)₄—[ | | 83 |
| 164 | 1 | 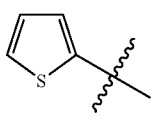 | 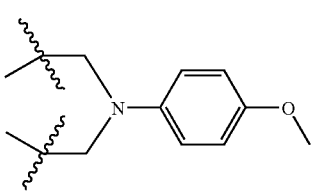 | | CH₂Ph | 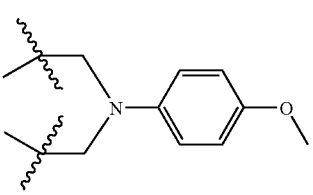 | | 93 |
| 165 | 1 | 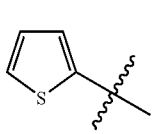 | 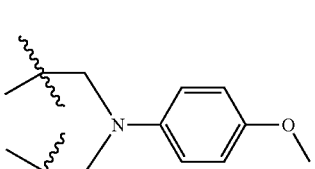 | | CH₂Ph | 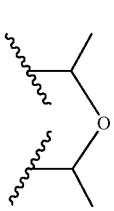 | | 93 |

-continued

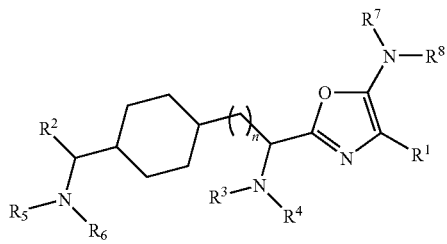

| n | $R^2$ | $R^3$ | $R^4$ | $R^1$ | $R^7$ | $R^8$ | μ-opioid receptor, % inhibition [1 μM] |
|---|---|---|---|---|---|---|---|
| 166 | 1 | (thienyl) | (benzyl) | | $CH_2Ph$ | (N-(4-methoxyphenyl)) | 78 |

The separation of diastereomers and/or enantiomers is carried out by methods known to the person skilled in the art, for example by recrystallisation, chromatography or in particular HPLC chromatography, or crystallisation with an optionally chiral acid or base and separation of the salts, or chiral HPLC chromatography (Fogassy et al., Optical resolution methods, Org. Biomol. Chem 2006, 4, 3011-3030).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted oxazole compound corresponding to Formula I:

I wherein
n is 0, 1 or 2;
$R^1$ denotes optionally mono- or polysubstituted aryl or heteroaryl bonded via a $C_{1-3}$-alkylene chain;
$R^2$ denotes optionally mono- or polysubstituted aryl or heteroaryl, or optionally mono- or polysubstituted aryl bonded via a $C_{1-3}$-alkylene chain;
$R^3$ and $R^4$ independently denote optionally mono- or polysubstituted, saturated or unsaturated, branched or unbranched $C_{1-6}$-alkyl; optionally mono- or polysubstituted aryl; or optionally mono- or polysubstituted aryl bonded via a $C_{1-3}$-alkylene chain; or $R^3$ and $R^4$ together form a saturated or unsaturated 5-, 6- or 7-membered non-aromatic ring optionally containing a further heteroatom selected from the group consisting of S, O or N, said non-aromatic ring being optionally mono- or polysubstituted and optionally condensed to an aromatic ring;

$R^5$ and $R^6$ independently denote H, or saturated or unsaturated, branched or unbranched $C_{1-6}$-alkyl, with the proviso that $R^5$ and $R^6$ are not simultaneously H; or $R^5$ and $R^6$ together denote —$CH_2CH_2OCH_2CH_2$—, or —$(CH_2)_{3-6}$—;

$R^7$ and $R^8$ independently denote optionally mono- or polysubstituted, saturated or unsaturated, branched or unbranched $C_{1-6}$-alkyl; optionally mono- or polysubstituted aryl or heteroaryl bonded via a $C_{1-3}$-alkylene chain; or $R^7$ and $R^8$ together form a saturated or unsaturated 5-, 6- or 7-membered non-aromatic ring optionally containing a further heteroatom selected from the group consisting of S, O and N, said non-aromatic ring being optionally mono- or polysubstituted and optionally condensed to an aromatic ring;

or a salt thereof with a physiologically acceptable acid.

2. A compound as claimed in claim 1, wherein said compound is in the form of an isolated stereoisomer.

3. A compound as claimed in claim 1, wherein said compound is in the form of a mixture of stereoisomers.

4. A compound as claimed in claim 3, wherein said compound is in the form of a racemic mixture.

5. A compound as claimed in claim 1, wherein $R^1$ denotes a phenyl group bonded via a $C_{1-3}$-alkylene chain, wherein said phenyl group is optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

6. A compound as claimed in claim 5, wherein $R^1$ denotes a benzyl group.

7. A compound as claimed in claim 1, wherein $R^2$ denotes phenyl or thienyl optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl; or a phenyl group bonded via a $C_{1-3}$-alkylene chain, wherein said phenyl group is optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl.

8. A compound as claimed in claim 7, wherein $R^2$ denotes phenyl optionally monosubstituted with Cl or F, or denotes thienyl.

9. A compound as claimed in claim 1, wherein:
$R^3$ and $R^4$ independently denote $C_{1-6}$-alkyl optionally mono- or polysubstituted with F, Cl, —CN, SH, S—$C_{1-6}$-alkyl, benzyl, OH, O-benzyl, O—$C_{1-6}$-alkyl, $CO_2H$, or $CO_2$—$C_{1-6}$-alkyl; or phenyl optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl; or
$R^3$ and $R^4$ together denote —$CH_2CH_2OCH_2CH_2$—, —$CH_2CH_2NR^9CH_2CH_2$—, —$(CH_2)_{4-5}$—, or

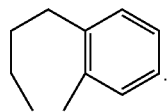

wherein
$R^9$ denotes a $C_{1-6}$-alkyl group or a phenyl group bonded via a $C_{1-3}$-alkylene chain, wherein said phenyl group is optionally mono- or polysubstituted with F, Cl, Br, I, CN, $NH_2$, NH—$C_{1-6}$-alkyl, NH—$C_{1-6}$-alkyl-OH, $N(C_{1-6}\text{-alkyl})_2$, $N(C_{1-6}\text{-alkyl-OH})_2$, $NO_2$, SH, S—$C_{1-6}$-alkyl, OH, O—$C_{1-6}$-alkyl, O—$C_{1-6}$alkyl-OH, C(=O)$C_{1-6}$-alkyl, $CO_2H$, $CO_2$—$C_{1-6}$-alkyl, $CF_3$, or $C_{1-6}$-alkyl.

10. A compound as claimed in claim 1, wherein $R^3$ and $R^4$ independently denote phenyl, ethyl or methyl; or $R^3$ and $R^4$ together denote —$CH_2CH_2OCH_2CH_2$—, —$CH_2CH_2NR^9CH_2CH_2$—, —$(CH_2)_{4-5}$— or

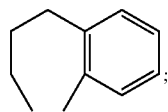

wherein $R^9$ denotes benzyl, 4-F-phenyl or 4-methoxyphenyl.

11. A compound as claimed in claim 1, wherein $R^5$ and $R^6$ each denote $CH_3$.

12. A compound as claimed in claim 1, wherein $R^7$ and $R^8$ independently denote benzyl or phenethyl optionally mono- or polysubstituted with F, Cl, CN, $NO_2$, SH, S—$C_{1-6}$-alkyl, OH, O—$C_{1-6}$-alkyl, $CO_2H$, $CO_2$—$C_{1-6}$-alkyl, $CF_3$, or $C_{1-6}$-alkyl; or
$R^7$ and $R^8$ together denote —$CH_2CH_2SCH_2CH_2$—, —$CH_2CH_2OCH_2CH_2$—, —$(CH_2)_5$— or —$CH_2CH_2NR^{10}CH_2CH_2$—, wherein individual H atoms can be replaced by branched or unbranched $C_{1-4}$-alkyl optionally mono- or polysubstituted with OH, $OCH_3$, CN, F, Cl, SH, $SCH_3$, $CF_3$ or benzyl;
wherein $R^{10}$ denotes phenyl, benzyl or phenethyl optionally mono- or polysubstituted with $CH_3$, $OCH_3$, OH, F, Cl, CN, SH, $SCH_3$ or $CF_3$.

13. A compound as claimed in claim 12, wherein $R^7$ and $R^8$ independently denote methyl, ethyl, benzyl or phenethyl; or $R^7$ and $R^8$ denote —$CH_2CH_2SCH_2CH_2$—, —$CH_2CH_2OCH_2CH_2$—, —$(CH_2)_4$— or —$(CH_2)_5$—, —$CH_2CH_2NR^{10}CH_2CH_2$—, wherein individual H atoms can be replaced by methyl or benzyl, and
$R^{10}$ denotes phenyl, 4-methoxyphenyl or benzyl.

14. A compound as claimed in claim 1, selected from the group consisting of:

17. [{4-[(4-benzyl-5-pyrrolidin-1-yl-oxazol-2-yl)-piperidin-1-yl-methyl]-cyclohexyl}-(4-fluorophenyl)-methyl]-dimethylamine;

18. ((4-benzyl-5-morpholin-4-yl-oxazol-2-yl)-{4-[dimethylamino-(4-fluorophenyl)-methyl]-cyclohexyl}-methyl)-methylphenylamine;

19. ([4-benzyl-5-(4-methylpiperidin-1-yl)-oxazol-2-yl]-{4-[dimethylamino-(4-fluorophenyl)-methyl]-cyclohexyl}-methyl)-methylphenylamine;

20. ([4-benzyl-5-(4-methylpiperidin-1-yl)-oxazol-2-yl]-{4-[(4-chlorophenyl)-dimethylaminomethyl]-cyclohexyl}-methyl)-diethylamine;

21. benzyl-[4-benzyl-2-({4-[(4-chlorophenyl)-dimethylaminomethyl]-cyclohexyl}-diethylaminomethyl)-oxazol-5-yl]-methylamine;

22. benzyl-{4-benzyl-2-[{4-[(4-chlorophenyl)-dimethylaminomethyl]-cyclohexyl}-(methylphenylamine)-methyl]-oxazol-5-yl}-methylamine;

23. [(4-{[4-benzyl-5-(4-benzylpiperidin-1-yl)-oxazol-2-yl]-piperidin-1-yl-methyl}-cyclohexyl)-thiophen-2-yl-methyl]-dimethylamine;

24. [(4-{[4-benzyl-5-(4-methylpiperidin-1-yl)-oxazol-2-yl]-piperidin-1-yl-methyl}-cyclohexyl)-thiophen-2-yl-methyl]-dimethylamine;

25. benzyl-(4-benzyl-2-{[4-(dimethylaminothiophen-2-yl-methyl)-cyclohexyl]-piperidin-1-yl-methyl}-oxazol-5-yl)-methylamine;

26. [(4-{[4-benzyl-5-(4-phenylpiperazin-1-yl)-oxazol-2-yl]-piperidin-1-yl-methyl}-cyclohexyl)-thiophen-2-yl-methyl]-dimethylamine;

27. {[4-benzyl-5-(4-benzylpiperidin-1-yl)-oxazol-2-yl]-[4-(dimethylaminothiophen-2-yl-methyl)-cyclohexyl]-methyl}-diethylamine;

28. {[4-benzyl-5-(4-benzylpiperazin-1-yl)-oxazol-2-yl]-[4-(dimethylaminothiophen-2-yl-methyl)-cyclohexyl]-methyl}-diethylamine;

29. {[4-benzyl-5-(4-methylpiperidin-1-yl)-oxazol-2-yl]-[4-(dimethylaminothiophen-2-yl-methyl)-cyclohexyl]-methyl}-diethylamine;

30. benzyl-(4-benzyl-2-{diethylamino-[4-(dimethylaminothiophen-2-yl-methyl)-cyclohexyl]-methyl}-oxazol-5-yl)-methylamine;

31. {[4-benzyl-5-(4-phenylpiperazin-1-yl)-oxazol-2-yl]-[4-(dimethylaminothiophen-2-yl-methyl)-cyclohexyl]-methyl}-diethylamine;

32. ({4-[[4-benzyl-5-(4-benzylpiperidin-1-yl)-oxazol-2-yl]-(4-benzylpiperazin-1-yl)-methyl]-cyclohexyl}-thiophen-2-yl-methyl)-dimethylamine;

33. [(4-{[4-benzyl-5-(3-methylpiperidin-1-yl)-oxazol-2-yl]-piperidin-1-yl-methyl}-cyclohexyl)-(4-fluorophenyl)-methyl]-dimethylamine;

34. [4-benzyl-2-(diethylamino-{4-[dimethylamino-(4-fluorophenyl)-methyl]-cyclohexyl}-methyl)-oxazol-5-yl]-methylphenethylamine;

35. [4-benzyl-2-(diethylamino-{4-[dimethylamino-(4-fluorophenyl)-methyl]-cyclohexyl}-methyl)-oxazol-5-yl]-methylphenethylamine;

36. ([4-benzyl-5-(3-methylpiperidin-1-yl)-oxazol-2-yl]-{4-[dimethylamino-(4-fluorophenyl)-methyl]-cyclohexyl}-methyl)-diethylamine;

37. ([4-benzyl-5-(3,5-dimethylpiperidin-1-yl)-oxazol-2-yl]-{4-[dimethylamino-(4-fluorophenyl)-methyl]-cyclohexyl}-methyl)-methylphenylamine;
38. {4-benzyl-2-[{4-[dimethylamino-(4-fluorophenyl)-methyl]-cyclohexyl}-(methylphenylamine)-methyl]-oxazol-5-yl}-methylphenethylamine;
39. [4-benzyl-2-({4-[(4-chlorophenyl)-dimethylaminomethyl]-cyclohexyl}-piperidin-1-yl-methyl)-oxazol-5-yl]-diethylamine;
40. [(4-{[4-benzyl-5-(3-methylpiperidin-1-yl)-oxazol-2-yl]-piperidin-1-yl-methyl}-cyclohexyl)-(4-chlorophenyl)-methyl]-dimethylamine;
41. ([4-benzyl-5-(3,5-dimethylpiperidin-1-yl)-oxazol-2-yl]-{4-[(4-chlorophenyl)-dimethylaminomethyl]-cyclohexyl}-methyl)-diethylamine;
42. ([4-benzyl-5-(3,5-dimethylpiperidin-1-yl)-oxazol-2-yl]-{4-[(4-chlorophenyl)-dimethylaminomethyl]-cyclohexyl}-methyl)-methylphenylamine;
43. {4-benzyl-2-[{4-[(4-chlorophenyl)-dimethylaminomethyl]-cyclohexyl}-(methylphenylamine)-methyl]-oxazol-5-yl}-methylphenethylamine;
44. [4-benzyl-2-((4-benzylpiperazin-1-yl)-{4-[(4-chlorophenyl)-dimethylaminomethyl]-cyclohexyl}-methyl)-oxazol-5-yl]-diethylamine;
45. [(4-{[4-benzyl-5-(3,5-dimethylpiperidin-1-yl)-oxazol-2-yl]-piperidin-1-yl-methyl}-cyclohexyl)-thiophen-2-yl-methyl]-dimethylamine;
46. (4-benzyl-2-{[4-(dimethylaminothiophen-2-yl-methyl)-cyclohexyl]-piperidin-1-yl-methyl}-oxazol-5-yl)-methylphenethylamine;
47. (4-benzyl-2-{[4-(dimethylaminothiophen-2-yl-methyl)-cyclohexyl]-piperidin-1-yl-methyl}-oxazol-5-yl)-diethylamine;
48. ({4-[(4-benzyl-5-thiomorpholin-4-yl-oxazol-2-yl)-piperidin-1-yl-methyl]-cyclohexyl}-thiophen-2-yl-methyl)-dimethylamine;
49. (4-benzyl-2-{diethylamino-[4-(dimethylaminothiophen-2-yl-methyl)-cyclohexyl]-methyl}-oxazol-5-yl)-methylphenethylamine;
50. (4-benzyl-2-{diethylamino-[4-(dimethylaminothiophen-2-yl-methyl)-cyclohexyl]-methyl}-oxazol-5-yl)-diethylamine;
51. {[4-benzyl-5-(3-methylpiperidin-1-yl)-oxazol-2-yl]-[4-(dimethylaminothiophen-2-yl-methyl)-cyclohexyl]-methyl}-diethylamine;
52. {(4-benzyl-5-thiomorpholin-4-yl-oxazol-2-yl)-[4-(dimethylaminothiophen-2-yl-methyl)-cyclohexyl]-methyl}-methylphenylamine;
53. ({4-[[4-benzyl-5-(3,5-dimethylpiperidin-1-yl)-oxazol-2-yl]-(4-benzylpiperazin-1-yl)-methyl]-cyclohexyl}-thiophen-2-yl-methyl)-dimethylamine;
54. (4-benzyl-2-{(4-benzylpiperazin-1-yl)-[4-(dimethylaminothiophen-2-yl-methyl)-cyclohexyl]-methyl}-oxazol-5-yl)-methylphenethylamine;
55. ({4-[(4-benzylpiperazin-1-yl)-(4-benzyl-5-thiomorpholin-4-yl-oxazol-2-yl)-methyl]-cyclohexyl}-thiophen-2-yl-methyl)-dimethylamine;
56. [(4-{2-[4-benzyl-5-(4-benzylpiperazin-1-yl)-oxazol-2-yl]-2-piperidin-1-yl-ethyl}-cyclohexyl)-(4-chlorophenyl)-methyl]-dimethylamine;
57. [(4-{2-[4-benzyl-5-(4-methylpiperidin-1-yl)-oxazol-2-yl]-2-piperidin-1-yl-ethyl}-cyclohexyl)-(4-chlorophenyl)-methyl]-dimethylamine;
58. benzyl-[4-benzyl-2-(2-{4-[(4-chlorophenyl)-dimethylaminomethyl]-cyclohexyl}-1-piperidin-1-yl-ethyl)-oxazol-5-yl]-methylamine;
59. (1-[4-benzyl-5-(4-benzylpiperidin-1-yl)-oxazol-2-yl]-2-{4-[(4-chlorophenyl)-dimethylaminomethyl]-cyclohexyl}-ethyl)-diethylamine;
60. (1-[4-benzyl-5-(4-methylpiperidin-1-yl)-oxazol-2-yl]-2-{4-[(4-chlorophenyl)-dimethylaminomethyl]-cyclohexyl}-ethyl)-diethylamine;
61. benzyl-[4-benzyl-2-(2-{4-[(4-chlorophenyl)-dimethylaminomethyl]-cyclohexyl}-1-diethylaminoethyl)-oxazol-5-yl]-methylamine;
62. [{4-[2-[4-benzyl-5-(4-benzylpiperidin-1-yl)-oxazol-2-yl]-2-(4-benzylpiperazin-1-yl)-ethyl]-cyclohexyl}-(4-chlorophenyl)-methyl]-dimethylamine;
63. [{4-[2-[4-benzyl-5-(4-benzylpiperazin-1-yl)-oxazol-2-yl]-2-(4-benzylpiperazin-1-yl)-ethyl]-cyclohexyl}-(4-chlorophenyl)-methyl]-dimethylamine;
64. [{4-[2-[4-benzyl-5-(4-methylpiperidin-1-yl)-oxazol-2-yl]-2-(4-benzyl-piperazin-1-yl)-ethyl]-cyclohexyl}-(4-chlorophenyl)-methyl]-dimethylamine;
65. [(4-{2-[4-benzyl-5-(4-methylpiperidin-1-yl)-oxazol-2-yl]-2-piperidin-1-yl-ethyl}-cyclohexyl)-(4-fluorophenyl)-methyl]-dimethylamine;
66. benzyl-[4-benzyl-2-(2-{4-[dimethylamino-(4-fluorophenyl)-methyl]-cyclohexyl}-1-piperidin-1-yl-ethyl)-oxazol-5-yl]-methylamine;
67. (1-[4-benzyl-5-(4-benzylpiperidin-1-yl)-oxazol-2-yl]-2-{4-[dimethylamino-(4-fluorophenyl)-methyl]-cyclohexyl}-ethyl)-diethylamine;
68. (1-[4-benzyl-5-(4-benzylpiperazin-1-yl)-oxazol-2-yl]-2-{4-[dimethylamino-(4-fluorophenyl)-methyl]-cyclohexyl}-ethyl)-diethylamine;
69. (1-[4-benzyl-5-(4-methylpiperidin-1-yl)-oxazol-2-yl]-2-{4-[dimethylamino-(4-fluorophenyl)-methyl]-cyclohexyl}-ethyl)-diethylamine;
70. benzyl-[4-benzyl-2-(1-diethylamino-2-{4-[dimethylamino-(4-fluorophenyl)-methyl]-cyclohexyl}-ethyl)-oxazol-5-yl]-methylamine;
71. [{4-[2-[4-benzyl-5-(4-methylpiperidin-1-yl)-oxazol-2-yl]-2-(4-benzylpiperazin-1-yl)-ethyl]-cyclohexyl}-(4-fluorophenyl)-methyl]-dimethylamine;
72. [(4-{2-[4-benzyl-5-(4-benzylpiperidin-1-yl)-oxazol-2-yl]-2-piperidin-1-yl-ethyl}-cyclohexyl)-thiophen-2-yl-methyl]-dimethylamine;
73. [(4-{2-[4-benzyl-5-(4-benzylpiperazin-1-yl)-oxazol-2-yl]-2-piperidin-1-yl-ethyl}-cyclohexyl)-thiophen-2-yl-methyl]-dimethylamine;
74. [(4-{2-[4-benzyl-5-(4-methylpiperidin-1-yl)-oxazol-2-yl]-2-piperidin-1-yl-ethyl}-cyclohexyl)-thiophen-2-yl-methyl]-dimethylamine;
75. benzyl-(4-benzyl-2-{2-[4-(dimethylaminothiophen-2-yl-methyl)-cyclohexyl]-1-piperidin-1-yl-ethyl}-oxazol-5-yl)-methylamine;
76. [(4-{2-[4-benzyl-5-(4-phenylpiperazin-1-yl)-oxazol-2-yl]-2-piperidin-1-yl-ethyl}-cyclohexyl)-thiophen-2-yl-methyl]-dimethylamine;
77. {1-[4-benzyl-5-(4-benzylpiperidin-1-yl)-oxazol-2-yl]-2-[4-(dimethylamino-thiophen-2-yl-methyl)-cyclohexyl]-ethyl}-diethylamine;
78. {1-[4-benzyl-5-(4-benzylpiperazin-1-yl)-oxazol-2-yl]-2-[4-(dimethylamino-thiophen-2-yl-methyl)-cyclohexyl]-ethyl}-diethylamine;
79. {1-[4-benzyl-5-(4-methylpiperidin-1-yl)-oxazol-2-yl]-2-[4-(dimethylamino-thiophen-2-yl-methyl)-cyclohexyl]-ethyl}-diethylamine;
80. benzyl-(4-benzyl-2-{1-diethylamino-2-[4-(dimethylaminothiophen-2-yl-methyl)-cyclohexyl]-ethyl}-oxazol-5-yl)-methylamine;

81. ({4-[2-[4-benzyl-5-(4-benzyl-piperidin-1-yl)-oxazol-2-yl]-2-(4-benzylpiperazin-1-yl)-ethyl]-cyclohexyl}-thiophen-2-yl-methyl)-dimethylamine;
82. ({4-[2-[4-benzyl-5-(4-benzylpiperazin-1-yl)-oxazol-2-yl]-2-(4-benzylpiperazin-1-yl)-ethyl]-cyclohexyl}-thiophen-2-yl-methyl)-dimethylamine;
83. ({4-[2-[4-benzyl-5-(4-methylpiperidin-1-yl)-oxazol-2-yl]-2-(4-benzylpiperazin-1-yl)-ethyl]-cyclohexyl}-thiophen-2-yl-methyl)-dimethylamine;
84. benzyl-(4-benzyl-2-{1-(4-benzylpiperazin-1-yl)-2-[4-(dimethylaminothiophen-2-yl-methyl)-cyclohexyl]-ethyl}-oxazol-5-yl)-methylamine;
85. ({4-[2-[4-benzyl-5-(4-phenylpiperazin-1-yl)-oxazol-2-yl]-2-(4-benzylpiperazin-1-yl)-ethyl]-cyclohexyl}-thiophen-2-yl-methyl)-dimethylamine;
86. [4-benzyl-2-(2-{4-[(4-chlorophenyl)-dimethylaminomethyl]-cyclohexyl}-1-piperidin-1-yl-ethyl)-oxazol-5-yl]-methylphenethylamine;
87. [4-benzyl-2-(2-{4-[(4-chlorophenyl)-dimethylaminomethyl]-cyclohexyl}-1-piperidin-1-yl-ethyl)-oxazol-5-yl]-diethylamine;
88. (1-[4-benzyl-5-(3,5-dimethylpiperidin-1-yl)-oxazol-2-yl]-2-{4-[(4-chlorophenyl)-dimethylaminomethyl]-cyclohexyl}-ethyl)-diethylamine;
89. [4-benzyl-2-(2-{4-[(4-chlorophenyl)-dimethylaminomethyl]-cyclohexyl}-1-diethylaminoethyl)-oxazol-5-yl]-methylphenethylamine;
90. [4-benzyl-2-(2-{4-[(4-chlorophenyl)-dimethylaminomethyl]-cyclohexyl}-1-diethylaminoethyl)-oxazol-5-yl]-diethylamine;
91. (1-(4-benzyl-5-thiomorpholin-4-yl-oxazol-2-yl)-2-{4-[(4-chlorophenyl)-dimethylaminomethyl]-cyclohexyl}-ethyl)-diethylamine;
92. (1-(4-benzyl-5-thiomorpholin-4-yl-oxazol-2-yl)-2-{4-[(4-chlorophenyl)-dimethylaminomethyl]-cyclohexyl}-ethyl)-methylphenylamine;
93. [4-benzyl-2-(1-(4-benzylpiperazin-1-yl)-2-{4-[(4-chlorophenyl)-dimethylaminomethyl]-cyclohexyl}-ethyl)-oxazol-5-yl]-methylphenethylamine;
94. [4-benzyl-2-(1-(4-benzylpiperazin-1-yl)-2-{4-[(4-chlorophenyl)-dimethylaminomethyl]-cyclohexyl}-ethyl)-oxazol-5-yl]-diethylamine;
95. [4-benzyl-2-(2-{4-[dimethylamino-(4-fluorophenyl)-methyl]-cyclohexyl}-1-piperidin-1-yl-ethyl)-oxazol-5-yl]-methylphenethylamine;
96. (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-diethylamine;
97. [4-benzyl-2-(1-diethylamino-2-{4-[dimethylamino-(4-fluorophenyl)-methyl]-cyclohexyl}-ethyl)-oxazol-5-yl]-methylphenethylamine;
98. [4-benzyl-2-(1-diethylamino-2-{4-[dimethylamino-(4-fluorophenyl)-methyl]-cyclohexyl}-ethyl)-oxazol-5-yl]-diethylamine;
99. (1-(4-benzyl-5-thiomorpholin-4-yl-oxazol-2-yl)-2-{4-[dimethylamino-(4-fluorophenyl)-methyl]-cyclohexyl}-ethyl)-diethylamine;
100. (1-[4-benzyl-5-(3-methylpiperidin-1-yl)-oxazol-2-yl]-2-{4-[dimethylamino-(4-fluorophenyl)-methyl]-cyclohexyl}-ethyl)-diethylamine;
101. (1-[4-benzyl-5-(3,5-dimethylpiperidin-1-yl)-oxazol-2-yl]-2-{4-[dimethylamino-(4-fluorophenyl)-methyl]-cyclohexyl}-ethyl)-methylphenylamine;
102. {4-benzyl-2-[2-{4-[dimethylamino-(4-fluorophenyl)-methyl]-cyclohexyl}-1-(methylphenylamine)-ethyl]-oxazol-5-yl}-methylphenethylamine;
103. {4-benzyl-2-[2-{4-[dimethylamino-(4-fluorophenyl)-methyl]-cyclohexyl}-1-(methylphenylamine)-ethyl]-oxazol-5-yl}-diethylamine;
104. (1-(4-benzyl-5-thiomorpholin-4-yl-oxazol-2-yl)-2-{4-[dimethylamino-(4-fluorophenyl)-methyl]-cyclohexyl}-ethyl)-methylphenylamine;
105. (1-[4-benzyl-5-(3-methylpiperidin-1-yl)-oxazol-2-yl]-2-{4-[dimethylamino-(4-fluorophenyl)-methyl]-cyclohexyl}-ethyl)-methylphenylamine;
106. [{4-[2-[4-benzyl-5-(3-methyl piperidin-1-yl)-oxazol-2-yl]-2-(4-benzyl piperazin-1-yl)-ethyl]-cyclohexyl}-(4-fluorophenyl)-methyl]-dimethylamine;
107. [(4-{2-[4-benzyl-5-(3,5-dimethylpiperidin-1-yl)-oxazol-2-yl]-2-piperidin-1-yl-ethyl}-cyclohexyl)-thiophen-2-yl-methyl]-dimethylamine;
108. (4-benzyl-2-{2-[4-(dimethylaminothiophen-2-yl-methyl)-cyclohexyl]-1-piperidin-1-yl-ethyl}-oxazol-5-yl)-methylphenethylamine;
109. (4-benzyl-2-{2-[4-(dimethylaminothiophen-2-yl-methyl)-cyclohexyl]-1-piperidin-1-yl-ethyl}-oxazol-5-yl)-dimethylamine;
110. ({4-[2-(4-benzyl-5-thiomorpholin-4-yl-oxazol-2-yl)-2-piperidin-1-yl-ethyl]-cyclohexyl}-thiophen-2-yl-methyl)-dimethylamine;
111. [(4-{2-[4-benzyl-5-(3-methylpiperidin-1-yl)-oxazol-2-yl]-2-piperidin-1-yl-ethyl}-cyclohexyl)-thiophen-2-yl-methyl]-dimethylamine;
112. {1-[4-benzyl-5-(3,5-dimethylpiperidin-1-yl)-oxazol-2-yl]-2-[4-(dimethylamino-thiophen-2-yl-methyl)-cyclohexyl]-ethyl}-diethylamine;
113. (4-benzyl-{1-diethylamino-2-[4-(dimethylaminothiophen-2-yl-methyl)-cyclohexyl]-ethyl}-oxazol-5-yl)-methylphenethylamine;
114. (4-benzyl-2-{1-diethylamino-2-[4-(dimethylaminothiophen-2-yl-methyl)-cyclohexyl]-ethyl}-oxazol-5-yl)-diethylamine;
115. {1-(4-benzyl-5-thiomorpholin-4-yl-oxazol-2-yl)-2-[4-(dimethylaminothiophen-2-yl-methyl)-cyclohexyl]-ethyl}-diethylamine;
116. {1-[4-benzyl-5-(3-methylpiperidin-1-yl)-oxazol-2-yl]-2-[4-(dimethylaminothiophen-2-yl-methyl)-cyclohexyl]-ethyl}-diethylamine;
117. {1-[4-benzyl-5-(3-methylpiperidin-1-yl)-oxazol-2-yl]-2-[4-(dimethylaminothiophen-2-yl-methyl)-cyclohexyl]-ethyl}-methylphenylamine;
118. ({4-[2-(4-benzylpiperazin-1-yl)-2-(4-benzyl-5-thiomorpholin-4-yl-oxazol-2-yl)-ethyl]-cyclohexyl}-thiophen-2-yl-methyl)-dimethylamine;
119. ({4-[2-[4-benzyl-5-(3-methylpiperidin-1-yl)-oxazol-2-yl]-2-(4-benzylpiperazin-1-yl)-ethyl]-cyclohexyl}-thiophen-2-yl-methyl)-dimethylamine;
120. [{4-[(4-benzyl-5-pyrrolidin-1-yl-oxazol-2-yl)-morpholin-4-yl-methyl]-cyclohexyl}-(3-fluorophenyl)-methyl]-dimethylamine;
121. [{4-[(4-benzyl-5-morpholin-4-yl-oxazol-2-yl)-morpholin-4-yl-methyl]-cyclohexyl}-(3-fluorophenyl)-methyl]-dimethylamine;
122. [(4-{(4-benzyl-5-pyrrolidin-1-yl-oxazol-2-yl)-[4-(4-fluorophenyl)-piperazin-1-yl]-methyl}-cyclohexyl)-(3-fluorophenyl)-methyl]-dimethylamine;
123. [(4-{(4-benzyl-5-pyrrolidin-1-yl-oxazol-2-yl)-[4-(4-methoxyphenyl)-piperazin-1-yl]-methyl}-cyclohexyl)-(3-fluorophenyl)-methyl]-dimethylamine;
124. [(4-{(4-benzyl-5-morpholin-4-yl-oxazol-2-yl)-[4-(4-methoxyphenyl)-piperazin-1-yl]-methyl}-cyclohexyl)-(3-fluorophenyl)-methyl]-dimethylamine;

125. [{4-[(4-benzyl-5-pyrrolidin-1-yl-oxazol-2-yl)-(3,4-dihydro-1H-isoquinolin-2-yl)-methyl]-cyclohexyl}-(3-fluorophenyl)-methyl]-dimethylamine;
126. [{4-[(4-benzyl-5-morpholin-4-yl-oxazol-2-yl)-(3,4-dihydro-1H-isoquinolin-2-yl)-methyl]-cyclohexyl}-(3-fluorophenyl)-methyl]-dimethylamine;
127. [{4-[{4-benzyl-5-[4-(4-methoxyphenyl)-piperazin-1-yl]-oxazol-2-yl}-(3,4-dihydro-1H-isoquinolin-2-yl)-methyl]-cyclohexyl}-(3-fluorophenyl)-methyl]-dimethylamine;
128. [{4-[[4-benzyl-5-(2,6-dimethylmorpholin-4-yl)-oxazol-2-yl]-(3,4-dihydro-1H-isoquinolin-2-yl)-methyl]-cyclohexyl}-(3-fluorophenyl)-methyl]-dimethylamine;
129. [{4-[(4-benzyl-5-pyrrolidin-1-yl-oxazol-2-yl)-morpholin-4-yl-methyl]-cyclohexyl}-(4-chlorophenyl)-methyl]-dimethylamine;
130. [{4-[(4-benzyl-5-morpholin-4-yl-oxazol-2-yl)-morpholin-4-yl-methyl]-cyclohexyl}-(4-chlorophenyl)-methyl]-dimethylamine;
131. [[4-({4-benzyl-5-[4-(4-methoxy-phenyl)-piperazin-1-yl]-oxazol-2-yl}-morpholin-4-yl-methyl)-cyclohexyl]-(4-chlorophenyl)-methyl]-dimethylamine;
132. [(4-{[4-benzyl-5-(2,6-dimethylmorpholin-4-yl)-oxazol-2-yl]-morpholin-4-yl-methyl}-cyclohexyl)-(4-chlorophenyl)-methyl]-dimethylamine;
133. [(4-{(4-benzyl-5-pyrrolidin-1-yl-oxazol-2-yl)-[4-(4-fluorophenyl)-piperazin-1-yl]-methyl}-cyclohexyl)-(4-chlorophenyl)-methyl]-dimethylamine;
134. [(4-{(4-benzyl-5-pyrrolidin-1-yl-oxazol-2-yl)-[4-(4-methoxyphenyl)-piperazin-1-yl]-methyl}-cyclohexyl)-(4-chlorophenyl)-methyl]-dimethylamine;
135. [(4-{(4-benzyl-5-morpholin-4-yl-oxazol-2-yl)-[4-(4-methoxyphenyl)-piperazin-1-yl]-methyl}-cyclohexyl)-(4-chlorophenyl)-methyl]-dimethylamine;
136. [(4-{[4-benzyl-5-(2,6-dimethylmorpholin-4-yl)-oxazol-2-yl]-[4-(4-methoxy-phenyl)-piperazin-1-yl]-methyl}-cyclohexyl)-(4-chlorophenyl)-methyl]-dimethylamine;
137. [{4-[(4-benzyl-5-pyrrolidin-1-yl-oxazol-2-yl)-(3,4-dihydro-1H-isoquinolin-2-yl)-methyl]-cyclohexyl}-(4-chlorophenyl)-methyl]-dimethylamine;
138. ({4-[(4-benzyl-5-pyrrolidin-1-yl-oxazol-2-yl)-morpholin-4-yl-methyl]-cyclohexyl}-thiophen-2-yl-methyl)-dimethylamine;
139. ({4-[(4-benzyl-5-morpholin-4-yl-oxazol-2-yl)-morpholin-4-yl-methyl]-cyclohexyl}-thiophen-2-yl-methyl)-dimethylamine;
140. {4-({4-benzyl-5-[4-(4-methoxyphenyl)-piperazin-1-yl]-oxazol-2-yl}-morpholin-4-yl-methyl)-cyclohexyl]-thiophen-2-yl-methyl}-dimethylamine;
141. [(4-{[4-benzyl-5-(2,6-dimethylmorpholin-4-yl)-oxazol-2-yl]-morpholin-4-yl-methyl}-cyclohexyl)-thiophen-2-yl-methyl]-dimethylamine;
142. [(4-{(4-benzyl-5-pyrrolidin-1-yl-oxazol-2-yl)-[4-(4-fluorophenyl)-piperazin-1-yl]-methyl}-cyclohexyl)-thiophen-2-yl-methyl]-dimethylamine
143. [(4-{(4-benzyl-5-pyrrolidin-1-yl-oxazol-2-yl)-[4-(4-methoxyphenyl)-piperazin-1-yl]-methyl}-cyclohexyl)-thiophen-2-yl-methyl]-dimethylamine;
144. [(4-{(4-benzyl-5-morpholin-4-yl-oxazol-2-yl)-[4-(4-methoxyphenyl)-piperazin-1-yl]-methyl}-cyclohexyl)-thiophen-2-yl-methyl]-dimethylamine;
145. [(4-{[4-benzyl-5-(2,6-dimethylmorpholin-4-yl)-oxazol-2-yl]-[4-(4-methoxy-phenyl)-piperazin-1-yl]-methyl}-cyclohexyl)-thiophen-2-yl-methyl]-dimethylamine;
146. ({4-[(4-benzyl-5-pyrrolidin-1-yl-oxazol-2-yl)-(3,4-dihydro-1H-isoquinolin-2-yl)-methyl]-cyclohexyl}-thiophen-2-yl-methyl)-dimethylamine;
147. ({4-[{4-benzyl-5-[4-(4-methoxyphenyl)-piperazin-1-yl]-oxazol-2-yl}-(3,4-dihydro-1H-isoquinolin-2-yl)-methyl]-cyclohexyl}-thiophen-2-yl-methyl)-dimethylamine;
148. ({4-[[4-benzyl-5-(2,6-dimethylmorpholin-4-yl)-oxazol-2-yl]-(3,4-dihydro-1H-isoquinolin-2-yl)-methyl]-cyclohexyl}-thiophen-2-yl-methyl)-dimethylamine;
149. [{4-[2-(4-benzyl-5-pyrrolidin-1-yl-oxazol-2-yl)-2-morpholin-4-yl-ethyl]-cyclohexyl}-(3-fluorophenyl)-methyl]-dimethylamine;
150. [{4-[2-(4-benzyl-5-morpholin-4-yl-oxazol-2-yl)-2-morpholin-4-yl-ethyl]-cyclohexyl}-(3-fluorophenyl)-methyl]-dimethylamine;
151. [[4-(2-{4-benzyl-5-[4-(4-methoxyphenyl)-piperazin-1-yl]-oxazol-2-yl}-2-morpholin-4-yl-ethyl)-cyclohexyl]-(3-fluorophenyl)-methyl]-dimethylamine;
152. [(4-{2-[4-benzyl-5-(2,6-dimethylmorpholin-4-yl)-oxazol-2-yl]-2-morpholin-4-yl-ethyl}-cyclohexyl)-(3-fluorophenyl)-methyl]-dimethylamine;
153. [(4-{2-[4-benzyl-5-(2,6-dimethylmorpholin-4-yl)-oxazol-2-yl]-2-[4-(4-fluorophenyl)-piperazin-1-yl]-ethyl}-cyclohexyl)-(3-fluorophenyl)-methyl]-dimethylamine;
154. [(4-{2-(4-benzyl-5-morpholin-4-yl-oxazol-2-yl)-2-[4-(4-methoxyphenyl)-piperazin-1-yl]-ethyl}-cyclohexyl)-(3-fluorophenyl)-methyl]-dimethylamine;
155. [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-(3-fluorophenyl)-methyl]-dimethylamine;
156. [(4-{2-[4-benzyl-5-(2,6-dimethylmorpholin-4-yl)-oxazol-2-yl]-2-[4-(4-methoxy-phenyl)-piperazin-1-yl]-ethyl}-cyclohexyl)-(3-fluorophenyl)-methyl]-dimethylamine;
157. [{4-[2-{4-benzyl-5-[4-(4-methoxyphenyl)-piperazin-1-yl]-oxazol-2-yl}-2-(3,4-dihydro-1H-isoquinolin-2-yl)-ethyl]-cyclohexyl}-(3-fluorophenyl)-methyl]-dimethylamine;
158. ({4-[2-(4-benzyl-5-morpholin-4-yl-oxazol-2-yl)-2-morpholin-4-yl-ethyl]-cyclohexyl}-thiophen-2-yl-methyl)-dimethylamine;
159. {4-(2-{4-benzyl-5-[4-(4-methoxyphenyl)-piperazin-1-yl]-oxazol-2-yl}-2-morpholin-4-yl-ethyl]-cyclohexyl]-thiophen-2-yl-methyl}-dimethylamine;
160. [(4-{2-[4-benzyl-5-(2,6-dimethylmorpholin-4-yl)-oxazol-2-yl]-2-morpholin-4-yl-ethyl}-cyclohexyl)-thiophen-2-yl-methyl]-dimethylamine;
161. [(4-{2-(4-benzyl-5-morpholin-4-yl-oxazol-2-yl)-2-[4-(4-fluorophenyl)-piperazin-1-yl]-ethyl}-cyclohexyl)-thiophen-2-yl-methyl]-dimethylamine;
162. [(4-{2-{4-benzyl-5-[4-(4-methoxyphenyl)-piperazin-1-yl]-oxazol-2-yl}-2-[4-(4-fluorophenyl)-piperazin-1-yl]-ethyl}-cyclohexyl)-thiophen-2-yl-methyl]-dimethylamine;
163. [(4-{2-(4-benzyl-5-pyrrolidin-1-yl-oxazol-2-yl)-2-[4-(4-methoxyphenyl)-piperazin-1-yl]-ethyl}-cyclohexyl)-thiophen-2-yl-methyl]-dimethylamine;
164. [(4-{2-{4-benzyl-5-[4-(4-methoxyphenyl)-piperazin-1-yl]-oxazol-2-yl}-2-[4-(4-methoxyphenyl)-piperazin-1-yl]-ethyl}-cyclohexyl)-thiophen-2-yl-methyl]-dimethylamine;

165. [(4-{2-[4-benzyl-5-(2,6-dimethylmorpholin-4-yl)-oxazol-2-yl]-2-[4-(4-methoxy-phenyl)-piperazin-1-yl]-ethyl}-cyclohexyl)-thiophen-2-yl-methyl]-dimethylamine; and 166. ({4-[2-{4-benzyl-5-[4-(4-methoxyphenyl)-piperazin-1-yl]-oxazol-2-yl}-2-(3,4-dihydro-1H-isoquinolin-2-yl)-ethyl]-cyclohexyl}-thiophen-2-yl-methyl)-dimethylamine;

or a salt thereof with a physiologically compatible acid.

15. A pharmaceutical composition comprising a compound as claimed in claim 1 and at least one pharmaceutically acceptable carrier or auxiliary substance.

16. A process for preparing a substituted oxazole compound as claimed in claim 1, said process comprising heating an aldehyde of Formula A with an amine of Formula B and an isonitrile amide of Formula C

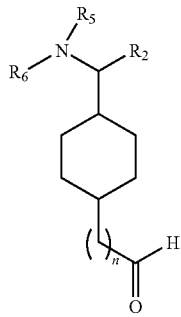

A

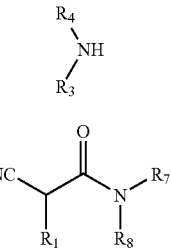

B

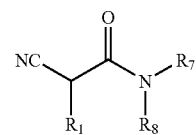

C wherein n and R1 through R8 have the meanings given in claim 1, in an organic solvent for 1-10 hours at a temperature between 30° and 100° C.

17. A process as claimed in claim 16, wherein the solvent is methanol or ethanol, and the heating is effected at a temperature of 40° to 80° C.

18. A method of treating a condition selected from the group consisting of pain, depression, urinary incontinence, diarrhea, pruritus, alcohol and drug misuse, drug dependency, lethargy and anxiety in a subject in need thereof, said method comprising administering to said subject a pharmacologically effective amount of a compound as claimed in claim 1.

19. A method as claimed in claim 18, wherein said condition is pain.

20. A method as claimed in claim 19, wherein said pain comprises acute pain, neuropathic pain or chronic pain.

* * * * *